US011741850B2

(12) United States Patent
Stroup

(10) Patent No.: US 11,741,850 B2
(45) Date of Patent: Aug. 29, 2023

(54) SYSTEM, MEDIA, AND METHOD FOR TRAINING MACHINE LEARNING ALGORITHMS TO IDENTIFY CHARACTERISTICS WITHIN TEST RESPONSES

(71) Applicant: Gened Corp., Austin, TX (US)

(72) Inventor: Walter Stroup, Austin, TX (US)

(73) Assignee: Gened Corp., Austin, TX (US)

( * ) Notice: Subject to any disclaimer, the term of this patent is extended or adjusted under 35 U.S.C. 154(b) by 0 days.

(21) Appl. No.: 17/853,659

(22) Filed: Jun. 29, 2022

(65) Prior Publication Data

US 2022/0351635 A1 Nov. 3, 2022

Related U.S. Application Data

(63) Continuation of application No. PCT/US2020/066795, filed on Dec. 23, 2020.

(60) Provisional application No. 62/955,786, filed on Dec. 31, 2019.

(51) Int. Cl.
*G09B 7/06* (2006.01)
*A61B 5/16* (2006.01)
*G06N 7/01* (2023.01)

(52) U.S. Cl.
CPC .............. *G09B 7/06* (2013.01); *A61B 5/165* (2013.01); *G06N 7/01* (2023.01)

(58) Field of Classification Search
CPC .......... G09B 7/06; A61B 5/165; G06N 7/005; G06N 20/00; G06N 3/0454; G06N 3/0481; G06Q 10/10; G06Q 50/20

USPC ....................................................... 434/167
See application file for complete search history.

(56) References Cited

U.S. PATENT DOCUMENTS

| | | | |
|---|---|---|---|
| 9,443,205 B2* | 9/2016 | Wall | G16H 40/67 |
| 2003/0180698 A1* | 9/2003 | Salerian | G09B 5/00 |
| | | | 434/118 |
| 2004/0014013 A1 | 1/2004 | Diesel et al. | |
| 2006/0194182 A1 | 8/2006 | Anand | |
| 2017/0004731 A1 | 1/2017 | Haruta et al. | |
| 2017/0177565 A1 | 6/2017 | Beason et al. | |
| 2017/0206456 A1* | 7/2017 | Stumbo | G06N 7/005 |
| 2017/0258385 A1* | 9/2017 | Ebrahim | G16H 20/00 |

FOREIGN PATENT DOCUMENTS

WO WO 2017172629 A1 10/2017

OTHER PUBLICATIONS

International Search Report and Written Opinion for PCT/US2020/066795, dated Apr. 22, 2021.

(Continued)

*Primary Examiner* — Peter S Vasat
*Assistant Examiner* — Stephen Alvesteffer
(74) *Attorney, Agent, or Firm* — Terrile, Cannatti & Chambers; Michael Rocco Cannatti

(57) ABSTRACT

Disclosed herein are systems, media, and method for training machine learning algorithms to identify an existence of a characteristic, a probability of the existence of the characteristic, or both for each a plurality of students comprising collecting a first plurality and second plurality of concatenated answers, creating a first training set comprising the collected sets of concatenated answers, and training the machine learning algorithm in a first stage using the first training set.

20 Claims, 64 Drawing Sheets

Information-rich dataset with computationally efficient, unambiguous representation

Machine Learning

Which model types to use is dependent on particular features of dataset

Our data:
• Categorical
• 0's or 1's

Training

Able to assign a class label and evaluate in terms of reliability

Prediction

Able to assign a class label to as-yet-unclassified instance evaluate in terms of accuracy

(56) References Cited

OTHER PUBLICATIONS

Romero, Oscar Yair Ortegon, Analysis and Adaptation of Questionnaires based on item response theory, Jun. 2019, https://www.lume.ufrgs.br/handle/10183/199317, p. 16.

* cited by examiner

This question may have more than one correct answer. Select all correct responses.
1. A group of friends is making cards for a fraction game. The cards need to show equivalent shaded fractions. They start with this card.
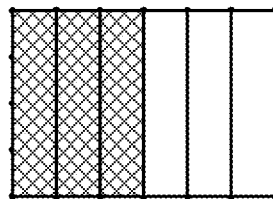
Which of these cards shows a shaded fraction that is equivalent to this card?
A 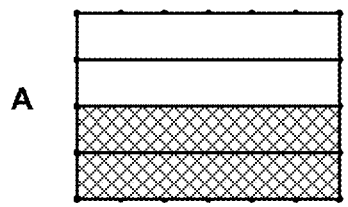
C 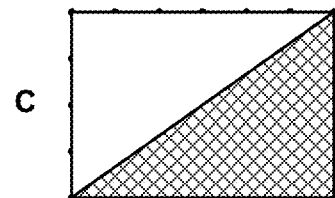
B 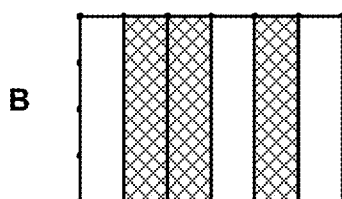
D 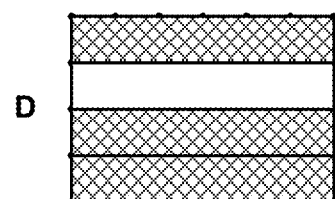
*Figure 3*

Fig. 4

*This question may have more than one correct answer. Select all correct responses.*

2.

There are a total of 36 bicycles in rows. There are the same number of bicycles in each row. Which equation can be used to find the number of bicycles in each row?

*This question may have more than one correct answer. Select all correct responses.*

3.

David's class is working on a project comparing amounts of food. These comparisons are made. Which of these could be correct?

A Gallons of milk are compared to quarts of milk

B Pounds of flour are compared to fluid ounces of milk

C Pounds of flour are compared to pounds of cheese

D Fluid ounces of juice are compared to fluid ounces of juice

Fig. 6

*This question may have more than one correct answer. Select all correct responses.*

4.

This addition problem is missing two numbers. Which numbers placed in the boxes below would make the addition correct?

$$\begin{array}{r} 7\;\square\;2 \\ +\;1\;\square\;3 \\ \hline 9\;4\;5 \end{array}$$

A  3 and 1

B  9 and 5

C  0 and 4

D  6 and 6

This question may have more than one correct answer.
Select all correct responses.

5. Two friends ate lunch together.
Felicia ate 1/3 of her sandwich. Daria ate ¼ of her pie.

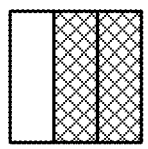 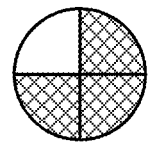

Which of these statements must be true?

A  Felicia ate a greater part of her sandwich than Daria ate of her pie because 1/3 > 1/4

B  Felicia ate more food than Daria ate

C  2/3 of the sandwich was not eaten by Felicia

D  3/3 of the pie was not eaten by Daria

*Figure 7*

This question may have more than one correct answer. Select all correct responses.
1. A group of friends is making cards for a fraction game. The cards need to show equivalent shaded fractions. They start with this card.
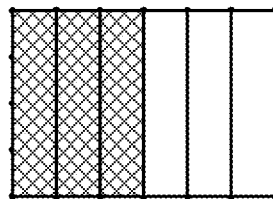
Which of these cards shows a shaded fraction that is equivalent to this card?
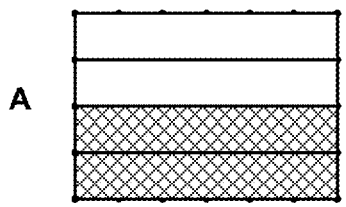
A
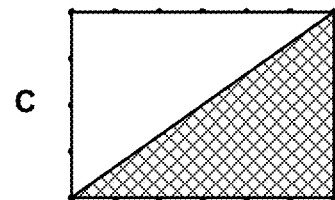
C
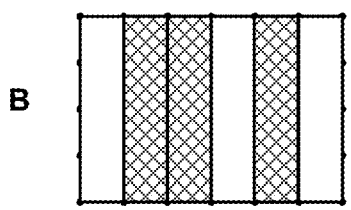
B
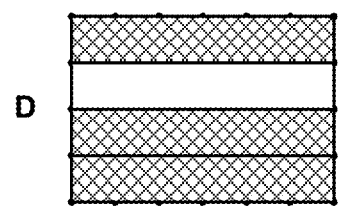
D
*Figure 8*

Fig. 9

*This question may have more than one correct answer. Select all correct responses.*

2. Which of these comparisons is true?

A  $\dfrac{3}{6} < \dfrac{3}{7}$

B  $\dfrac{1}{5} < \dfrac{2}{10}$

C  $\dfrac{2}{5} < \dfrac{3}{5}$

D  $\dfrac{3}{7} < \dfrac{4}{5}$

Fig. 10

*This question may have more than one correct answer. Select all correct responses.*

3.

Mike has 42 baseball cards. Maria starts with twice as many cards as Mike. Maria then gives away 6 cards. Which equation can be used to find $y$, the number of baseball cards Maria has now?

A  $42 - 6 + 42 = y$

B  $2 \times 42 + 6 = y$

C  $84 - 6 = y$

D  $42 \times 2 - 6 = y$

This question may have more than one correct answer.
Select all correct responses.

4. Which of these triangles appears to be obtuse?

This question may have more than one correct answer.
Select all correct responses.

5. Two friends ate lunch together.
Felicia ate 1/3 of her sandwich. Daria ate 1/4 of her pie.

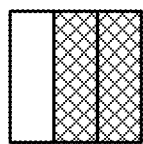 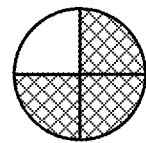

Which of these statements must be true?

A  Felicia ate a greater part of her sandwich than Daria ate of her pie because 1/3 > 1/4

B  Felicia ate more food than Daria ate

C  2/3 of the sandwich was not eaten by Felicia

D  3/3 of the pie was not eaten by Daria

*Figure 12*

This question may have more than one correct answer.
Select all correct responses.
1. A group of friends is making cards for a fraction game. The cards need to show equivalent shaded fractions. They start with this card.
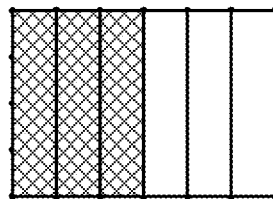
Which of these cards shows a shaded fraction that is equivalent to this card?
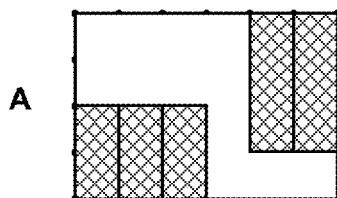
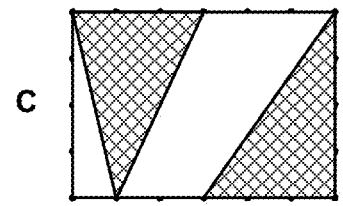
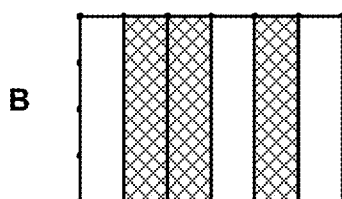
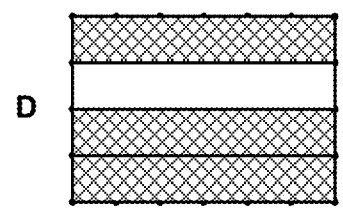
*Figure 13*

Fig. 14

*This question may have more than one correct answer. Select all correct responses.*

2. Which of these is possible?

A  A rhombus with five sides

B  A triangle with two obtuse angles

C  A polygon with fewer than four sides

D  A polygon with only obtuse angles

This question may have more than one correct answer.
Select all correct responses.

3. Which points are within the rectangle shown?

A (2.711, 1.989)
B (2, 2)
C (2, 3)
D (3.181, 3.181)

This question may have more than one correct answer. Select all correct responses.

4. Duane wants to make a box shaped like a rectangular prism with the same volume as the box shown below.

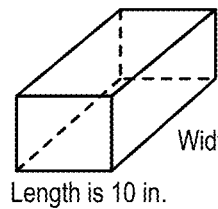

Height is 8 in.
Width is 16 in.
Length is 10 in.

He wants the new box to have a height of 12 inches.

Which of these could be true of the new box?

A  The new box could have a length greater than 10 inches

B  The new box could have a length greater than 10 inches and a width greater than 16 inches C  The width of the new box could be less than 16 inches and the length could be less than 10 inches D  The area of the base for the new box could be greater than the area of the base for the box shown

*Figure 16*

This question may have more than one correct answer.
Select all correct responses.

5. Two friends ate lunch together.
Felicia ate 1/3 of her sandwich. Daria ate 1/4 of her pie.

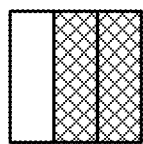 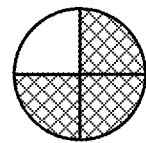

Which of these statements must be true?

A  Felicia ate a greater part of her sandwich than Daria ate of her pie because 1/3 > 1/4

B  Felicia ate more food than Daria ate

C  2/3 of the sandwich was not eaten by Felicia

D  3/3 of the pie was not eaten by Daria

*Figure 17*

This question may have more than one correct answer.
Select all correct responses.
1. A group of friends is making cards for a fraction game. The cards need to show equivalent shaded fractions. They start with this card.
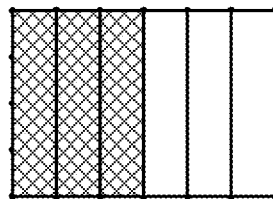
Which of these cards shows a shaded fraction that is equivalent to this card?
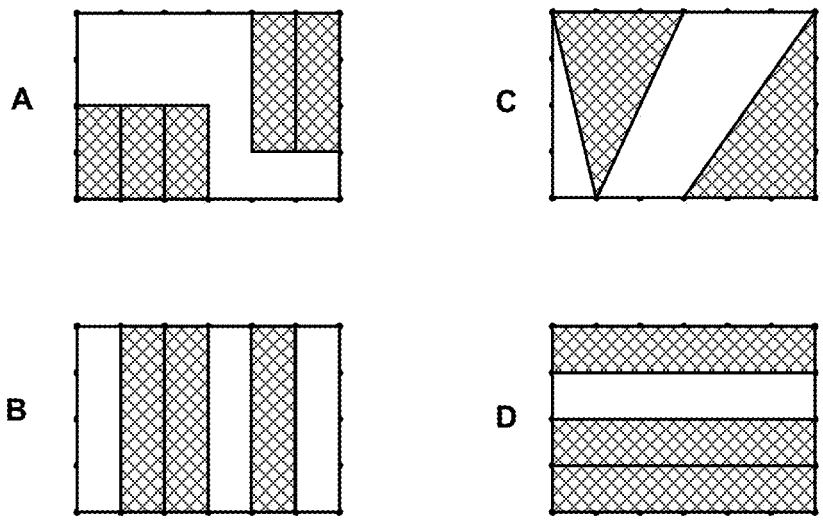
*Figure 18*

This question may have more than one correct answer. Select all correct responses.

2. Duane wants to make a box shaped like a rectangular prism with the same volume as the box shown below.

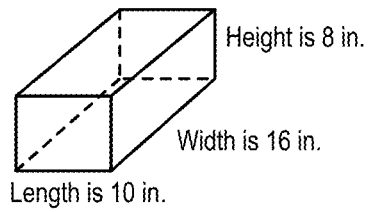

Height is 8 in.
Width is 16 in.
Length is 10 in.

He wants the new box to have a height of 12 inches.

Which of these could be true of the new box?

A  The new box could have a length greater than 10 inches

B  The new box could have a length greater than 10 inches and a width greater than 16 inches C  The width of the new box could be less than 16 inches and the length could be less than 10 inches D  The area of the base for the new box could be greater than the area of the base for the box shown

*Figure 19*

This question may have more than one correct answer.
Select all correct responses.

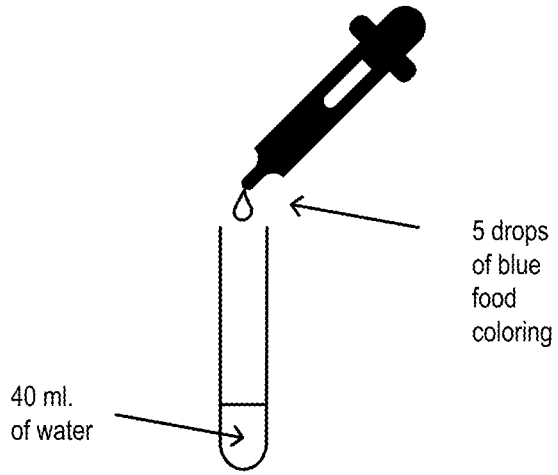

5. 5 drops of blue food coloring are mixed with 40 milliliters of water to produce a blue solution. Which of the following mixtures would produce a solution with same ratio of drops of food coloring to milliliters of water?

A  15 drops in 50 milliliters of water
    B  10 drops in 80 milliliters of water
    C  0.2 drops in 1.6 milliliters of water
    D  6 drops in 48 milliliters of water

*Figure 21*

This question may have more than one correct answer.
Select all correct responses.

6. Each point on this graph represents the height and arm span for a student in a math class. One more data point is to be added for Mary. Which of the following points for Mary is *unlikely?*

A (180, 180)
B (167, 170)
C (150, 190)
D (180, 160)

This question may have more than one correct answer.
Select all correct responses.
1. A group of friends is making cards for a fraction game. The cards need to show equivalent shaded fractions. They start with this card.
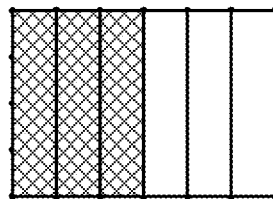
Which of these cards shows a shaded fraction that is equivalent to this card?
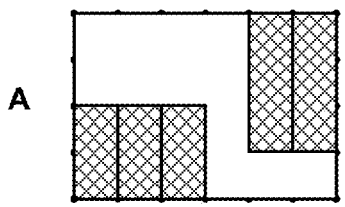
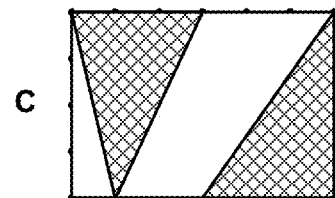
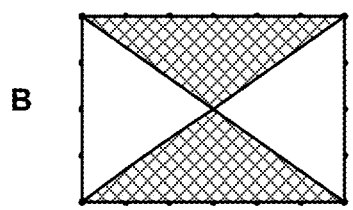
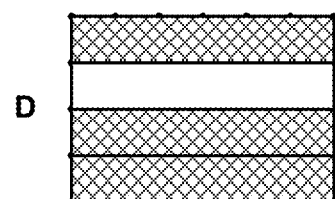
*Figure 23*

This question may have more than one correct answer. Select all correct responses.

2. Duane wants to make a box shaped like a rectangular prism with the same volume as the box shown below.

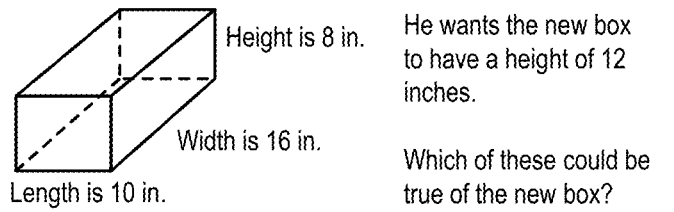

He wants the new box to have a height of 12 inches.

Which of these could be true of the new box?

A  The new box could have a length greater than 10 inches

B  The new box could have a length greater than 10 inches and a width greater than 16 inches C  The width of the new box could be less than 16 inches and the length could be less than 10 inches D  The area of the base for the new box could be greater than the area of the base for the box shown

4. *This question may have more than one correct answer. Select all correct responses.*

Which of these is a rational number?

A    −2

B    $\dfrac{1}{3}$

C    $1\dfrac{1}{2}$

D    0.6789992

This question may have more than one correct answer.
Select all correct responses.

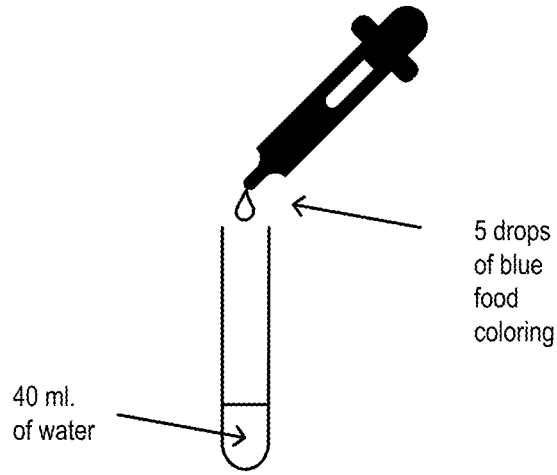

40 ml. of water 5 drops of blue food coloring

5. 5 drops of blue food coloring are mixed with 40 milliliters of water to produce a blue solution. Which of the following mixtures would produce a solution with same ratio of drops of food coloring to milliliters of water?

A  15 drops in 50 milliliters of water
B  10 drops in 80 milliliters of water
C  0.2 drops in 1.6 milliliters of water
D  6 drops in 48 milliliters of water

*Figure 27*

This question may have more than one correct answer.
Select all correct responses.

6. Each point on this graph represents the height and arm span for a student in a math class. One more data point is to be added for Mary. Which of the following points for Mary is *unlikely?*

A (180, 180)
B (167, 170)
C (150, 190)
D (180, 160)

This question may have more than one correct answer.
Select all correct responses.
1. A group of friends is making cards for a fraction game. The cards need to show equivalent shaded fractions. They start with this card.
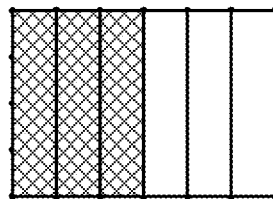
Which of these cards shows a shaded fraction that is equivalent to this card?
A 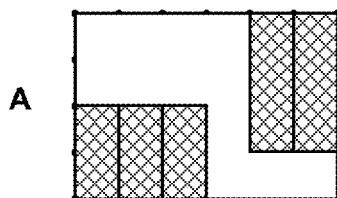
C 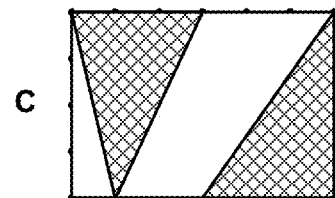
B 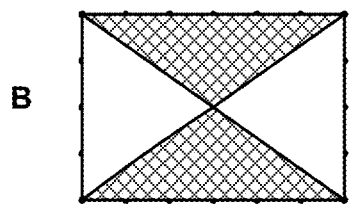
D 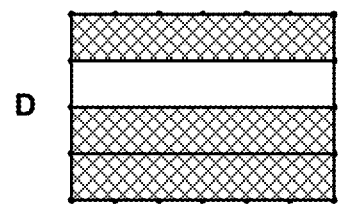
*Figure 29*

This question may have more than one correct answer.
Select all correct responses.

2. Duane wants to make a box shaped like a rectangular prism with the same volume as the box shown below.

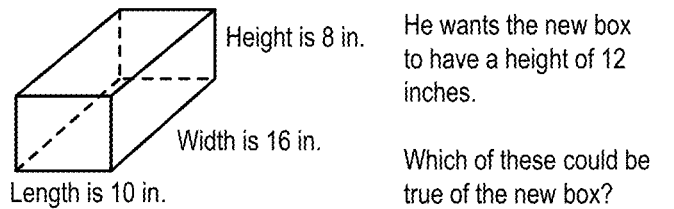

He wants the new box to have a height of 12 inches.

Which of these could be true of the new box?

A  The new box could have a length greater than 10 inches

B  The new box could have a length greater than 10 inches and a width greater than 16 inches C  The width of the new box could be less than 16 inches and the length could be less than 10 inches D  The area of the base for the new box could be greater than the area of the base for the box shown

*This question may have more than one correct answer. Select all correct responses.*

3.

Which of these is a rational number?

A    $-2$

B    $\dfrac{1}{3}$

C    $1\dfrac{1}{2}$

D    $0.6789992$

This question may have more than one correct answer.
Select all correct responses.

6. Each point on this graph represents the height and arm span for a student in a math class. One more data point is to be added for Mary. Which of the following points for Mary is *unlikely?*

A (180, 180)
B (167, 170)
C (150, 190)
D (180, 160)

This question may have more than one correct answer.
Select all correct responses.

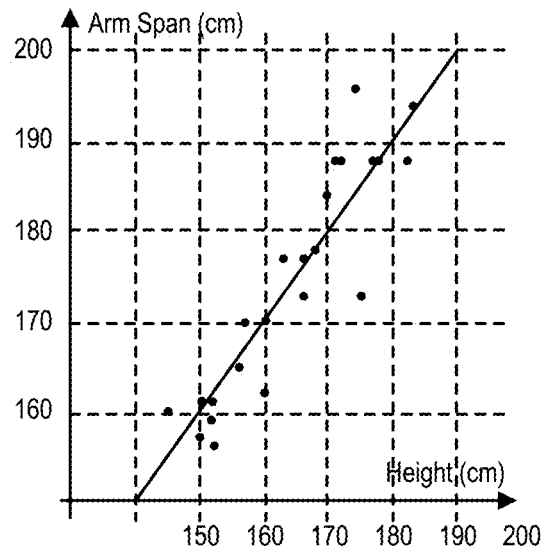

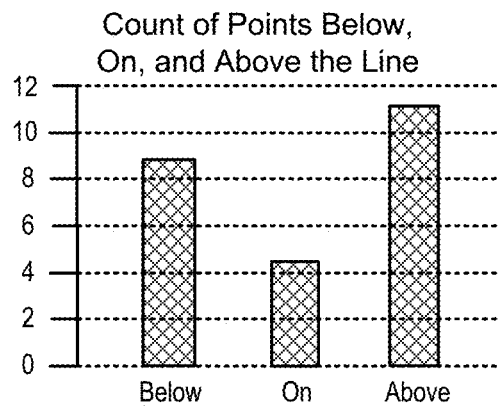

6. A student sees a *pattern* in the graph of height and arm span data for her class. She says, "Our arm spans are the same as our heights," and she draws the line for arm span being equal to height on the graph.

To investigate this idea, the class counts the number of students below, on, and above this line and represents this data with a bar graph. Which of the following can be concluded?

A The bar graph shows the pattern is unlikely to be valid

B The line graph shows the pattern is likely to be valid

C In this class there are more students who have arm spans greater than their heights

D In this class there are more students who have heights greater than their arm spans

*Figure 33*

This question may have more than one correct answer.
Select all correct responses.

6. Lines *j* and *k* are parallel. Which of the shown movements of only one point could keep the area of triangle ABC constant?

Q i

R ii

S iii

T iv

This question may have more than one correct answer.
Select all correct responses.

7. Given only the following, which of these could be used in the transformation of A to A'?

A Rotation

B Two Horizontal Reflections

C Translation

D 1: Dilation

Fig. 36

*This question may have more than one correct answer. Select all correct responses.*

8.

A student is given the equation $$2x + 4 = 6x + 2$$

and is asked to solve for x. Which of the following could be used in solving for x?

A As a first step, divide both sides of the equation by 2

B As a first step, subtract 2x from both sides of the equation

C As a first step, subtract 2 from *only* the right side of the equation.

D As a first step, subtract 2 from both sides of the equation

Fig. 42

|  |  |  |  |  | Score |
|---|---|---|---|---|---|
| Student 1 | A |  |  |  | 0 |
| Student 2 |  |  | C |  | 0 |
| Student 3 |  | B |  |  | 1 |
| Student 4 |  |  |  | D | 0 |
| Student 5 |  |  |  |  | 0 |

Fig. 45A

|  |  |  |  |  | Stored |
|---|---|---|---|---|---|
| Student 1 | A | B | C |  | A,B,C |
| Student 2 |  | B | C |  | B,C |
| Student 3 | A |  |  | D | A,D |
| Student 4 |  |  |  |  |  |
| Student 5 |  |  | C | D | C,D |

Fig. 45B

|  |  |  |  |  | Score |
|---|---|---|---|---|---|
| Student 1 | A | B | C |  | 0 |
| Student 2 |  | B | C |  | 1 |
| Student 3 | A |  |  | D | 0 |
| Student 4 |  |  |  |  | 0 |
| Student 5 |  |  | C | D | 0 |

Fig. 48

| Item 1 | Item 2 |
|---|---|
| A, B | No response |
| First Concatenated Response ||
| A, B ||
| Item 1 | Item 2 |
| No response | A,B |
| Second Concatenated Response ||
| A, B ||

Fig. 49A

| Item 1 | Item 2 |
|---|---|
| ABC | D |
| Concatenated Response ||
| ABCD ||
| 01100001011000100110001101100100 ||

Fig. 49B

| Item 1 | Item 2 |
|---|---|
| A, D | B, C |
| Concatenated Response ||
| A,DB,C ||
| 01100001001011000110001001100011000110010110001100100 ||

Fig. 49C

| Item 1 | Item 2 | Item 3 |
|---|---|---|
| A,D | - | B,C |
| Concatenated Response |||
| A,DB,C |||
| 01100001001011000110001001100011000110010110001100100 |||

Fig. 50

| Question 1 | Question 2 |
|---|---|
| 1101 | 0110 |
| Concatenated Response ||
| 11010110 ||

Fig. 51A

|  |  |  |  |  | Stored |
|---|---|---|---|---|---|
| Item 1 | A | B | C |  | 1110 |
| Item 2 |  | B | C |  | 0110 |
| Item 3 | A |  |  | D | 1001 |
| Item 4 |  |  |  |  | 0000 |
| Item 5 |  |  | C | D | 0011 |
| Concatenated | 11100110100100000011 | | | | |

Fig. 51B

|  |  |  |  |  | Stored |
|---|---|---|---|---|---|
| Student 1 | A | B | C |  | 1110 |
| Student 2 |  | B | C |  | 0110 |
| Student 3 | A |  |  | D | 1001 |
| Student 4 |  |  |  |  | 0000 |
| Student 5 |  |  | C | D | 0011 |
| Concatenated | 11100110100100000011 | | | | |

Fig. 52

| Student 1 | | | | | Stored |
|---|---|---|---|---|---|
| Item 1 | | B | C | | 0110 |
| Item 2 | A | | | D | 1001 |
| Item 3 | | | | | 0000 |
| Student 2 | | | | | |
| Item 1 | | B | C | | 0110 |
| Item 2 | | | | | 0000 |
| Item 3 | A | | | | 1000 |
| Student 3 | | | | | |
| Item 1 | A | B | C | D | 1111 |
| Item 2 | | B | | D | 1001 |
| Item 3 | | B | | | 0100 |
| Concatenated | colspan | | | | 011010010000011000001000111110010100 |

| Concatenated | 01101001000001100000100011110010100 |
|---|---|

Fig. 53

Student 1

"01011111111001110010011101000011000100"

Q1   Q2   Q3   Q4   Q5   Q6   Q7   Q8   Q9   Q10

5301

Student 2

"1011000010001001011011101100011 01101011"

(1) Class Label ("dyscalculia" [1/0] or "ELL" [1/0]) structures patterns in responses)

| Four Responses to Q1 | | | | Four Responses to Q2 | | | | Four Responses to Q3 | | | |

| classif | q01r01 | q01r02 | q01r03 | q01r04 | q02r01 | q02r02 | q02r03 | q02r04 | q03r01 | q04r02 | q04r03 | q04r04 |
|---|---|---|---|---|---|---|---|---|---|---|---|---|
| 0 | 1 | 1 | 0 | 0 | 0 | 1 | 1 | 0 | 1 | 0 | 1 | 1 |
| 0 | 0 | 0 | 1 | 1 | 0 | 0 | 0 | 1 | 0 | 1 | 1 | 2 |
| 0 | 1 | 0 | 0 | 0 | 0 | 1 | 0 | 0 | 1 | 1 | 0 | 0 |
| 1 | 1 | 1 | 1 | 1 | 1 | 1 | 1 | 1 | 0 | 0 | 0 | 0 |
| 0 | 0 | 0 | 0 | 0 | 0 | 1 | 0 | 0 | 1 | 0 | 1 | 1 |
| 0 | 1 | 1 | 0 | 1 | 1 | 0 | 0 | 1 | 0 | 1 | 1 | 1 |
| 0 | 0 | 0 | 1 | 0 | 1 | 1 | 1 | 0 | 1 | 1 | 0 | 2 |
| 0 | 0 | 0 | 0 | 1 | 1 | 0 | 1 | 1 | 0 | 1 | 1 | 1 |
| 1 | 1 | 1 | 1 | 1 | 1 | 1 | 1 | 1 | 0 | 0 | 0 | 0 |

Class Label Relates to Patterns in Selection/Non-Selection of Responses q02r03 = IF($A2=0,IF(RAND()<0.5,1,0),IF(RAND()<0.5,1,0))
q01r04 = IF($A2=0,IF(RAND()<0.3,1,0),IF(RAND()<0.8,1,0))
q03r03 = IF($A6=0,IF(RAND()<0.8,1,0),IF(RAND()<0.3,1,0))

(2) Machine learning can be used to model the patterns in responses

*Figure 54*

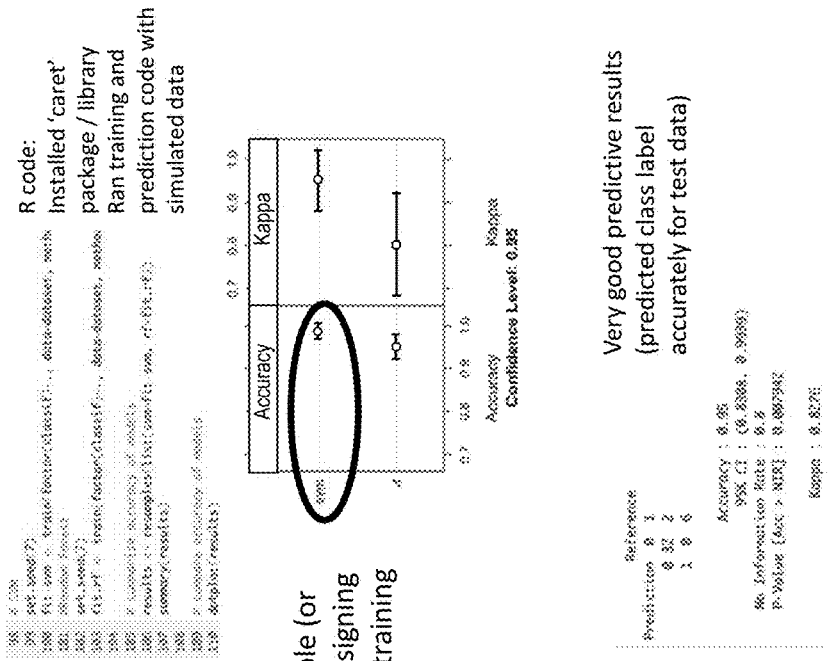
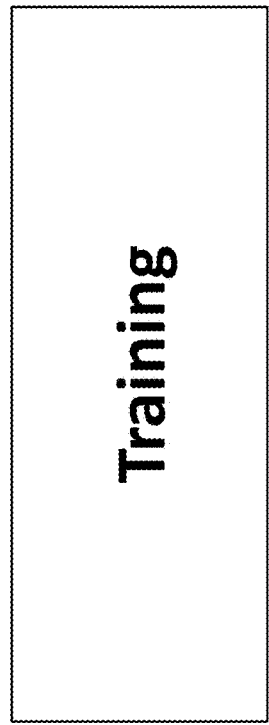
Figure 56

Fig. 60

```
> # summarize accuracy of models
> results <- resamples(list(svm=fit.svm, rf=fit.rf))
> summary(results)

Call:
summary.resamples(object = results)

Models: svm, rf
Number of resamples: 10

Accuracy
      Min. 1st Qu. Median   Mean 3rd Qu. Max. NA's
svm 0.9375  1.0000 1.0000 0.9875 1.000000    1    0
rf  0.8750  0.9375 0.9375 0.9500 0.984375    1    0

Kappa
         Min.   1st Qu.    Median      Mean   3rd Qu. Max. NA's
svm 0.7647059 1.0000000 1.0000000 0.9529412 1.0000000    1    0
rf  0.4482759 0.7647059 0.7647059 0.8036511 0.9411765    1    0
```

Fig. 62

```
# estimate skill of Support Vector Machines (SVM) with a linear
kernel on the validation dataset
predictions <- predict(fit.svm, validation)
confusionMatrix(as.factor(predictions), as.factor(validation$classif))

# estimate skill of Random Forest (RF) on the validation dataset
predictions <- predict(fit.rf, validation)
confusionMatrix(as.factor(predictions), as.factor(validation$classif))
```

Fig. 63

```
> # estimate skill of SVM on the validation dataset
> predictions <- predict(fit.svm, validation)
> confusionMatrix(as.factor(predictions), as.factor(validation$classif))
Confusion Matrix and Statistics Reference
Prediction  0  1
         0 32  0
         1  0  8

Accuracy : 1
                 95% CI : (0.9119, 1)
    No Information Rate : 0.8
    P-Value [Acc > NIR] : 0.0001329

Kappa : 1

Mcnemar's Test P-Value : NA

Sensitivity : 1.0
            Specificity : 1.0
         Pos Pred Value : 1.0
         Neg Pred Value : 1.0
             Prevalence : 0.8
         Detection Rate : 0.8
   Detection Prevalence : 0.8
      Balanced Accuracy : 1.0

'Positive' Class : 0
```

Fig. 64

```
> # estimate skill of Random Forest (RF) on the validation dataset
> predictions <- predict(fit.rf, validation)
> confusionMatrix(as.factor(predictions), as.factor(validation$classif))
Confusion Matrix and Statistics Reference
Prediction  0  1
         0 32  2
         1  0  6

Accuracy : 0.95
                 95% CI : (0.8308, 0.9939)
    No Information Rate : 0.8
    P-Value [Acc > NIR] : 0.007942

Kappa : 0.8276

Mcnemar's Test P-Value : 0.479500

Sensitivity : 1.0000
            Specificity : 0.7500
         Pos Pred Value : 0.9412
         Neg Pred Value : 1.0000
             Prevalence : 0.8000
         Detection Rate : 0.8000
   Detection Prevalence : 0.8500
      Balanced Accuracy : 0.8750

'Positive' Class : 0
```

SYSTEM, MEDIA, AND METHOD FOR TRAINING MACHINE LEARNING ALGORITHMS TO IDENTIFY CHARACTERISTICS WITHIN TEST RESPONSES

CROSS-REFERENCE

This application is a bypass continuation claiming priority to and benefit of International Application No. PCT/US2020/066795, filed on Dec. 23, 2020 and U.S. Provisional Application Ser. No. 62/955,786 filed Dec. 31, 2019, each of which is hereby incorporated by reference in its entirety as if fully set forth herein.

BACKGROUND OF THE INVENTION

In science, technology, engineering and mathematics (STEM) education along with other subject matter or educational topics, dichotomous items are widely used for evaluation and analysis of learning outcomes. Items can be tasks, activities, or assignments to which a user responds for the purposes of assessment. Dichotomous items include standard single-select multiple choice questions where only one of the responses is identified as correct among the choices. A correct response is typically scored as '1'. Selecting any of the other response is incorrect and is typically scored as '0'. Dichotomous items also can include multiple select items where there can be more than one correct response among the choices. If all and only the correct responses are selected, then the item result is coded as correct. All other possible combinations of responses are scored as incorrect. With only two possible states for the coding, multi-select items remains dichotomous (i.e., 0 or 1).

SUMMARY OF THE INVENTION

Traditional items or dichotomous items have only 2 states, correct, or incorrect. A dichotomous item can only have one right answer while a non-dichotomous generative assessment item can have more than one correct answer or response. A non-dichotomous generative assessment item may also provide multiple states between a correct answer and an incorrect answer. A non-dichotomous generative assessment item herein is capable of collecting much more information from a student, thus it advantageous facilitate identification of meaningful patterns in student responses. In some embodiments, non-dichotomous generative assessment items provide the additional benefit of providing for maximizing information density within a shorter amount of time. By way of example, in contrast to administering 5 separate dichotomous items in the form of 5 separate multiple choice questions to students over ten minutes (i.e., two minutes for each dichotomous item), administering a single non-dichotomous generative assessment item in the form of a single multiple choice question to students over 5 minutes may provide the same or greater amount of information to educators over a shorter period of time. The systems and methods herein advantageous provide an opportunity for an educator to characterize issues and opportunities related to instruction. The systems and methods herein also includes other advantages such as enabling assessments of depth of understanding within a grade and across grades, allowing interpretation by educators in ways they recognize as having implications for classroom practices. Further, the systems and methods herein can provide stakeholders in the educational system with a range of information that can be utilized to improve learning outcomes for all students.

Technical challenges exist when storing responses to traditional, dichotomous items. In a traditional dichotomous assessment item, each response within such a traditional item is treated separately and independently and each such separate response are frequently represented with commas or tabs delimiting the responses. For example, a response including multiple selections to a traditional dichotomous assessment item with four options "A," "B," "C," and "D," a student selecting "A," "B," and "D" would be represented in such a traditional system as either "A,B,D" or "A B D" in a string variable. In practice, this requires the computer memory to store a significant amount of data for each of those three separate A, B, and D selections. The letters A, B, and D in ASCII, require 8 bits each for storage. Because the "A,B,D" selections are not as important as the final correct/non-correct score, the "A,B,D" selection is only temporarily stored in a volatile memory. Once the temporarily stored "A,B,D" selection is compared to a single correct combination of selections and the "0" (incorrect) or "1" (correct) score is provided, the "A,B,D" selection is deleted. Only the binary correct/non-correct score is preserved and the specific combination of selections is lost forever. Hence, a technical tool to preserve data provenance while maximizing data storage for student responses is necessary.

Other technical challenges abound if the temporarily stored responses to dichotomous assessment items were to be compared and processed. Because the traditional system treats any selection as independent, any comparison of these independent responses would result in inconsistent and ambiguous processing by the computer.

The increased quantity of storage required by current scoring methods of summing the results from dichotomous or non-dichotomous test questions that are not stored in binary format prevents its use in machine learning pattern detection. However, the efficiently compact cross-item concatenating answer storage methods herein can be used to produce educationally meaningful pattern-based results from information rich datasets (e.g., millions of student responses). Further, the specific machine learning algorithms and methods of training such algorithms provided herein enable the detection of various student characteristic patterns from large student answer datasets.

Described herein are systems, methods, and media that provide in some embodiments a technological tool that, inter alia, preserves data provenance of student responses to non-dichotomous generative assessment items while maximizing data storage. In further embodiments, the claimed systems, methods, and media promote more consistent and reliable computer processing for responses to non-dichotomous generative assessment items. In some embodiments, the claimed systems, methods, and media form the foundation for a student learning data processing pipeline that would facilitate future machine learning algorithm utilization.

One aspect provided herein is a non-transitory computer-readable storage media encoded with a computer program including instructions executable by a processor to create a non-dichotomous answer processing application for e-learning, the application comprising: a prompt module, displaying a non-dichotomous generative assessment item comprising a series of two or more answer choices; a recording module, receiving a student answer to each answer choice in the series, wherein each student answer comprises an answer selection or an answer non-selection; a storage module, storing the received student answer to each answer choice in the series in a binary format, wherein any answer selection is stored as a first binary number and any answer non-selection is stored as a second binary number; and a concatenation module, concatenating every binarily stored student answer in the series to form a concatenated answer, wherein the concatenated answer does not comprise a delimiter.

In some embodiments, the prompt module further displays two or more non-dichotomous generative assessment items; the recording module further receives the student answer to each answer choice for each of the two or more non-dichotomous generative assessment items; the storage module, further stores the received student answer to each answer choice in the series for each of the two or more non-dichotomous generative assessment items, in the binary format; and the concatenation module, further concatenating every concatenated answer for each of the two or more non-dichotomous generative assessment items to form a multiple item concatenated answer. In some embodiments, the prompt module further displays the non-dichotomous generative assessment item to two or more students; the recording module further receives the student answer to each answer choice in the series for each of the two or more students; the storage module, further stores the received student answer to each answer choice for each of the two or more students, in a binary format; and the concatenation module, further concatenating every concatenated answer for each of the two or more students to form a multiple student concatenated answer. In some embodiments, the two or more answer choices comprise 3, 4, 5, 6, 7, 8, 9, 10 or more answer choices. In some embodiments, the two or more non-dichotomous generative assessment items comprise 3, 4, 5, 6, 7, 8, 9, 10 or more non-dichotomous generative assessment items. In some embodiments, the two or more students comprise 3, 4, 5, 6, 7, 8, 9, 10 or more students. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, a size of the multiple student concatenated answer is equal to AC*S bits, and wherein AC equals a number of answer choices, and wherein S equals a number of students. In some embodiments, the application further comprises a conversion module converting the concatenated answer to a vector representation for use of a machine learning process. In some embodiments, the application further comprises a conversion module converting the multiple item concatenated answer to a vector representation for use of a machine learning process. In some embodiments, the application further comprises a conversion module converting the multiple student concatenated answer to a vector representation for use of a machine learning process. In some embodiments, the application further comprises a training module training a machine learning algorithm on the concatenated answer. In some embodiments, the application further comprises a training module training a machine learning algorithm on the multiple item concatenated answer. In some embodiments, the application further comprises a training module training a machine learning algorithm on the multiple student concatenated answer. In some embodiments, the application further comprises a machine learning module performing a machine learning algorithm on the concatenated answer to determine an answer pattern. In some embodiments, the application further comprises a machine learning module performing a machine learning algorithm on the multiple item concatenated answer to determine an answer pattern. In some embodiments, the application further comprises a machine learning module performing a machine learning algorithm on the multiple student concatenated answer to determine an answer pattern. In some embodiments, the concatenated answer is not ambiguous. In some embodiments, the multiple item concatenated answer is not ambiguous. In some embodiments, the multiple student concatenated answer is not ambiguous. In some embodiments, the application further comprises a blockchain module, storing the concatenated answer in an immutable data storage. In some embodiments, the application further comprises a blockchain module, storing the multiple question concatenated answer in an immutable data storage. In some embodiments, the application further comprises a blockchain module, storing the multiple student concatenated answer in an immutable data storage. In some embodiments, the application further comprises a histogram module forming a histogram from the concatenated answer. In some embodiments, the application further comprises a histogram module forming a histogram from the multiple item concatenated answer. In some embodiments, the application further comprises a histogram module forming a histogram from the multiple student concatenated answer. In some embodiments, the histogram comprises a histogram of the possible combinations of answer choices. In some embodiments, the first binary number is 1 and the second binary number is 0. In some embodiments, the first binary number is 0 and the second binary number is 1. In some embodiments, each of the two or more answer choices is not independent from each other. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices.

Another aspect provided herein is a computer-implemented method for an e-learning non-dichotomous answer processing, the method comprising: displaying, by the computer, a non-dichotomous generative assessment item comprising a series of two or more answer choices; receiving, by the computer, a student answer to each answer choice in the series, wherein each student answer comprises an answer selection or an answer non-selection; storing, by the computer, the received student answer to each answer choice in the series in a binary format, wherein any answer selection is stored as a first binary number and any answer non-selection is stored as a second binary number; and concatenating, by the computer, every binarily stored student answer in the series to form a concatenated answer, wherein the concatenated answer does not comprise a delimiter.

In some embodiments: the prompt module further displays two or more non-dichotomous generative assessment items; the recording module further receives the student answer to each answer choice for each of the two or more non-dichotomous generative assessment items; the storage module, further stores the received student answer to each answer choice in the series for each of the two or more non-dichotomous generative assessment items, in the binary format; and the concatenation module, further concatenating every concatenated answer for each of the two or more non-dichotomous generative assessment items to form a multiple item concatenated answer. In some embodiments, the prompt module further displays the non-dichotomous generative assessment item to two or more students; the recording module further receives the student answer to each answer choice in the series for each of the two or more students; the storage module, further stores the received student answer to each answer choice for each of the two or more students, in a binary format; and the concatenation module, further concatenating every concatenated answer for each of the two or more students to form a multiple student concatenated answer. In some embodiments, the two or more answer choices comprise 3, 4, 5, 6, 7, 8, 9, 10 or more answer choices. In some embodiments, the two or more non-dichotomous generative assessment items comprise 3, 4, 5, 6, 7, 8, 9, 10 or more non-dichotomous generative assessment items. In some embodiments, the two or more students comprise 3, 4, 5, 6, 7, 8, 9, 10 or more students. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, a size of the multiple student concatenated answer is equal to AC*S bits, and wherein AC equals a number of answer choices, and wherein S equals a number of students. In some embodiments, the method further comprises converting, by a conversion module, the concatenated answer to a vector representation for use of a machine learning process. In some embodiments, the method further comprises converting, by a conversion module, the multiple item concatenated answer to a vector representation for use of a machine learning process. In some embodiments, the method further comprises converting, by a conversion module, the multiple student concatenated answer to a vector representation for use of a machine learning process. In some embodiments, the method further comprises training, by a training module, a machine learning algorithm on the concatenated answer. In some embodiments, the method further comprises training, by a training module, a machine learning algorithm on the multiple item concatenated answer. In some embodiments, the method further comprises training, by a training module, a machine learning algorithm on the multiple student concatenated answer. In some embodiments, the method further comprises performing, by a machine learning module, a machine learning algorithm on the concatenated answer to determine an answer pattern. In some embodiments, the method further comprises performing by a machine learning module, a machine learning algorithm on the multiple item concatenated answer to determine an answer pattern. In some embodiments, the method further comprises performing by a machine learning module, a machine learning algorithm on the multiple student concatenated answer to determine an answer pattern. In some embodiments, the concatenated answer is not ambiguous. In some embodiments, the multiple item concatenated answer is not ambiguous. In some embodiments, the multiple student concatenated answer is not ambiguous. In some embodiments, the method further comprises storing, by a blockchain module, the concatenated answer in an immutable data storage. In some embodiments, the method further comprises storing, by a blockchain module, the multiple question concatenated answer in an immutable data storage. In some embodiments, the method further comprises storing, by a blockchain module, the multiple student concatenated answer in an immutable data storage. In some embodiments, the method further comprises forming, by a histogram module, a histogram from the concatenated answer. In some embodiments, the method further comprises forming, by a histogram module, a histogram from the multiple item concatenated answer. In some embodiments, the method further comprises forming, by a histogram module, a histogram from the multiple student concatenated answer. In some embodiments, the histogram comprises a histogram of the possible combinations of answer choices. In some embodiments, the first binary number is 1 and the second binary number is 0. In some embodiments, the first binary number is 0 and the second binary number is 1. In some embodiments, each of the two or more answer choices is not independent from each other. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices.

Another aspect provided herein is a computer-implemented system comprising: a digital processing device comprising: at least one processor, an operating system configured to perform executable instructions, a memory, and a computer program including instructions executable by the digital processing device to create a non-dichotomous answer processing application for e-learning, the application comprising: a prompt module, displaying a non-dichotomous generative assessment item comprising a series of two or more answer choices; a recording module, receiving a student answer to each answer choice in the series, wherein each student answer comprises an answer selection or an answer non-selection; a storage module, storing the received student answer to each answer choice in the series in a binary format, wherein any answer selection is stored as a first binary number and any answer non-selection is stored as a second binary number; and a concatenation module, concatenating every binarily stored student answer in the series to form a concatenated answer, wherein the concatenated answer does not comprise a delimiter. In some embodiments: the prompt module further displays two or more non-dichotomous generative assessment items; the recording module further receives the student answer to each answer choice for each of the two or more non-dichotomous generative assessment items; the storage module, further stores the received student answer to each answer choice in the series for each of the two or more non-dichotomous generative assessment items, in the binary format; and the concatenation module, further concatenating every concatenated answer for each of the two or more non-dichotomous generative assessment items to form a multiple item concatenated answer. In some embodiments, the prompt module further displays the non-dichotomous generative assessment item to two or more students; the recording module further receives the student answer to each answer choice in the series for each of the two or more students; the storage module, further stores the received student answer to each answer choice for each of the two or more students, in a binary format; and the concatenation module, further concatenating every concatenated answer for each of the two or more students to form a multiple student concatenated answer. In some embodiments, the two or more answer choices comprise 3, 4, 5, 6, 7, 8, 9, 10 or more answer choices. In some embodiments, the two or more non-dichotomous generative assessment items comprise 3, 4, 5, 6, 7, 8, 9, 10 or more non-dichotomous generative assessment items. In some embodiments, the two or more students comprise 3, 4, 5, 6, 7, 8, 9, 10 or more students. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, a size of the multiple student concatenated answer is equal to AC*S bits, and wherein AC equals a number of answer choices, and wherein S equals a number of students. In some embodiments, the application further comprises a conversion module converting the concatenated answer to a vector representation for use of a machine learning process. In some embodiments, the application further comprises a conversion module converting the multiple item concatenated answer to a vector representation for use of a machine learning process. In some embodiments, the application further comprises a conversion module converting the multiple student concatenated answer to a vector representation for use of a machine learning process. In some embodiments, the application further comprises a training module training a machine learning algorithm on the concatenated answer. In some embodiments, the application further comprises a training module training a machine learning algorithm on the multiple item concatenated answer. In some embodiments, the application further comprises a training module training a machine learning algorithm on the multiple student concatenated answer. In some embodiments, the application further comprises a machine learning module performing a machine learning algorithm on the concatenated answer to determine an answer pattern. In some embodiments, the application further comprises a machine learning module performing a machine learning algorithm on the multiple item concatenated answer to determine an answer pattern. In some embodiments, the application further comprises a machine learning module performing a machine learning algorithm on the multiple student concatenated answer to determine an answer pattern. In some embodiments, the concatenated answer is not ambiguous. In some embodiments, the multiple item concatenated answer is not ambiguous. In some embodiments, the multiple student concatenated answer is not ambiguous. In some embodiments, the application further comprises a blockchain module, storing the concatenated answer in an immutable data storage. In some embodiments, the application further comprises a blockchain module, storing the multiple question concatenated answer in an immutable data storage. In some embodiments, the application further comprises a blockchain module, storing the multiple student concatenated answer in an immutable data storage. In some embodiments, the application further comprises a histogram module forming a histogram from the concatenated answer. In some embodiments, the application further comprises a histogram module forming a histogram from the multiple item concatenated answer. In some embodiments, the application further comprises a histogram module forming a histogram from the multiple student concatenated answer. In some embodiments, the histogram comprises a histogram of the possible combinations of answer choices. In some embodiments, the first binary number is 1 and the second binary number is 0. In some embodiments, the first binary number is 0 and the second binary number is 1. In some embodiments, each of the two or more answer choices is not independent from each other. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices.

In another aspect disclosed herein are computer-implemented methods for generative assessment item development, the method comprising: obtaining a released assessment item, wherein the released assessment item comprising a correct answer or a combination of correction answers; generating a question for the generative assessment item, wherein the question comprises information in the correct answer or the combination correction of answers of the released assessment item; and generating a plurality of responses to the question for the generative assessment item, wherein the plurality of responses comprises at least two responses that are not independent, and wherein the plurality of responses are non-dichotomous.

In another aspect, disclosed herein are computer-implemented methods for generative assessment item analysis, the method comprising: generating, by a computer, a plurality of responses to a question of the generative assessment item, wherein the plurality of responses comprises at least two responses that are not independent, and wherein the plurality of responses are non-dichotomous; and developing a set of rules for encoding the plurality of responses, wherein encoding of the plurality of responses generates a plurality of patterns, each pattern uniquely represent a response of the plurality of responses, wherein the plurality of patterns comprising: one or more first patterns representing baseline understanding of the question; one or more second patterns representing accurate understanding of the question; and one or more third patterns representing intermediate understanding of the question.

In yet another aspect, disclosed herein are computer-implemented methods for generative assessment item analysis, the method comprising: receiving, by a computer, a response to the generative assessment item from a user, wherein the response is selected by the user among a plurality of responses; encoding, by the computer, the response with a pre-determined set of rules thereby generating an encoded response, the encoded response comprising a pattern, wherein the pattern uniquely represents the response; and analyzing, by the computer, the pattern and a plurality of patterns, the plurality of patterns corresponding to at least a portion of the plurality of responses to the generative assessment item.

In some embodiments, the method further comprises receiving the response to the generative assessment item from the user in a group-based cloud computing system. In some embodiments, the generative assessment item is one or more of: a task, an assignment, an activity, a multiple choice question, and an order list question. In some embodiments, the generative assessment item is a non-dichotomous item. In some embodiments, when scored non-dichotomously, the plurality of responses contains at least 2×, 4×, 8×, or 16× information than scoring the plurality of responses dichotomously. In some embodiments, the method herein further comprises providing a generative assessment item to a user. In some embodiments, providing a generative assessment item to a user comprises presenting a generative assessment item in a group-based cloud computing system. In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, at least one of the numbers of virtual classrooms is author-able at a group activity level and at a learner level. In some embodiments, the method further comprises allowing the user to: create a coded object or behavior, post an image with embedded code in a gallery, select an object from the gallery to be added to the user's work space, or a combination thereof. In some embodiments, the method further comprises allowing the user or an activity author to select when and to whom a student space or a group-shared space is available. In some embodiments, the method further comprises allowing the user to turn on or off updates in the student space or the group-shared space. In some embodiments, the student space or the group-shared space is virtual space accessible by the user via a user interface. In some embodiments, the method further comprises allowing the user to code using one or more agent-based modeling languages. In some embodiments, the method further comprises combining an additional encoding with the encoded response to generate a second encoded response.

In some embodiments, the additional encoding is based on information of the user. In some embodiments, the information of the user comprises demographical information. In some embodiments, the encoded response may include one or more number, letter, symbol, or a combination thereof. In some embodiments, analyzing the pattern and a plurality of patterns comprises generating a histogram of the pattern and the plurality of patterns. In some embodiments, the histogram indicates a frequency of occurrence of one or more responses among the plurality of responses based on the pattern and the plurality of patterns. In some embodiments, each of the plurality of responses is uniquely associated with a pre-determined pattern. In some embodiments, at least two among the response and the plurality of responses are not independent. In some embodiments, the pre-determined set of rules comprises one or more of: base-2 numbering rules, base-10 numbering rules, base-8 numbering rules, and base-16 numbering rules. In some embodiments, the generative assessment item is related to science, technology, engineering, and mathematics (STEM).

In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level. In some embodiments, the generative assessment item is related to preparation for or taking a standardized test including the Wechsler Individual Achievement Test (WIAT), Kaufman Test of Educational Achievement (KTEA), Woodcock-Johnson Tests of Achievement (WJ), Peabody Individual Achievement Test (PIAT-R), National Assessment of Educational Progress (NAEP), General Educational Development (GED), Iowa Test of Basic Skills (ITBS), Scholastic Aptitude Test (SAT), Classic Learning Test (CLT), Former English Language Proficiency Test (ELPT), Preliminary SAT/National Merit Scholarship Qualifying Test (PSAT/NMSQT), Independent School Entrance Examination (ISEE), Secondary School Admission Test (SSAT), High School Placement Test (HSPT), Cooperative admissions examination program (COOP), Specialized High School Admissions Test (SHSAT), Scholastic Aptitude Test (SAT), English Language Proficiency Test (ELPT), American College Test (ACT), Classic Learning Test (CLT), Allied Health Professions Admission Test (AHPAT), Dental Admission Test (DAT), Graduate Management Admission Test (GMAT), Graduate Record Examination (GRE), Law School Admission Test (LSAT), Miller Analogies Test (MAT), Medical College Admission Test (MCAT), Optometry Admission Test (OAT), Pharmacy College Admission Test (PCAT), Veterinary College Admission Test (VCAT), Wiesen Test of Mechanical Aptitude (WTMA), Test of English for International Communication (TOEIC), Test of English as a Foreign Language (TOEFL), International English Language Testing System (IELTS), Certified Public Accountant (CPA), Examination for Professional Practice in Psychology (EPPP), Fundamentals of Engineering (FE), Multistate Bar Examination (MBE), Multistate Pharmacy Jurisprudence Examination (MPJE), Multistate Professional Responsibility Examination (MPRE), North American Pharmacist Licensure Examination (NAPLEX), National Council Licensure Examination for Practical Nurses (NCLEX-PN), National Council Licensure Examination for Registered Nurses (NCLEX-RN), Physician Assistant National Certifying Exam for physician assistants (PA), Principles and Practice of Engineering Exam, Uniform Certified Public Accountant Examination, Uniform Combined State Law Examination, Uniform Securities Agent State Law Examination, United States Medical Licensing Examination, USPTO registration examination, or any combination thereof.

In yet another aspect, disclose herein are computer-implemented systems for generative assessment item development, the system comprising: a digital processing device comprising: at least one processor, an operating system configured to perform executable instructions, a memory, and a computer program including instructions executable by the digital processing device to create an application comprising: a software module obtaining a released assessment item, wherein the released assessment item comprising a correct answer or a combination of correction answers; a software module generating a question for the generative assessment item, wherein the question comprises information in the correct answer or the combination correction of answers; and a software module generating a plurality of responses to the question for the generative assessment item, wherein the plurality of responses comprises at least two responses that are not independent, and wherein the plurality of responses are non-dichotomous.

In yet another aspect, disclose herein are computer-implemented systems for generative assessment item development, the system comprising: a digital processing device comprising: at least one processor, an operating system configured to perform executable instructions, a memory, and a computer program including instructions executable by the digital processing device to create an application comprising: a software module generating a plurality of responses to a question of the generative assessment item, wherein the plurality of responses comprises at least two responses that are not independent, and wherein the plurality of responses are non-dichotomous; and a software module developing a set of rules for encoding the plurality of responses, wherein encoding of the plurality of responses generates a plurality of patterns, each pattern uniquely represent a response of the plurality of responses, wherein the plurality of patterns comprising: one or more first patterns representing baseline understanding of the question; one or more second patterns representing accurate understanding of the question; and one or more third patterns representing intermediate understanding of the question.

In yet another aspect, disclose herein are computer-implemented systems for generative assessment item development, the system comprising: a digital processing device comprising: at least one processor, an operating system configured to perform executable instructions, a memory, and a computer program including instructions executable by the digital processing device to create an application comprising: a software module receiving a response to the generative assessment item from a user, wherein the response is selected by the user among a plurality of responses; a software module encoding the response with a pre-determined set of rules thereby generating an encoded response, the encoded response comprising a pattern, wherein the pattern uniquely represents the response; and a software module analyzing the pattern and a plurality of patterns, the plurality of patterns corresponding to at least a portion of the plurality of responses to the generative assessment item.

In some embodiments, the generative assessment item is one or more of: a task, an assignment, an activity, a multiple choice question, and an order list question. In some embodiments, the generative assessment item is a non-dichotomous item. In some embodiments, when scored non-dichotomously, the plurality of responses contains at least 2×, 4×, 8×, or 16× information than scoring the plurality of responses dichotomously. In some embodiments, the system herein further comprises a software module providing a generative assessment item to a user. In some embodiments, providing a generative assessment item to a user comprises presenting a generative assessment item in a group-based cloud computing system. In some embodiments, the system further comprises a software module receiving the response to the generative assessment item from the user in a group-based cloud computing system. In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, at least one of the number of virtual classrooms are author-able at a group activity level and at a learner level. In some embodiments, the system further comprises allowing the user to: create a coded object or behavior, post an image with embedded code in a gallery, select an object from the gallery to be added to the user's work space, or a combination thereof. In some embodiments, further comprises allowing the user or an activity author to select when and to whom a student space or a group-shared space is available. In some embodiments, the system further comprises allowing the user to turn on or off updates in the student space or the group-shared space. In some embodiments, the student space or the group-shared space is virtual space accessible by the user via a user interface. In some embodiments, the system further comprises allowing the user to code using one or more agent-based modeling languages. In some embodiments, the system further comprises a software module combining an additional encoding with the encoded response to generate a second encoded response. In some embodiments, the additional encoding is based on information of the user. In some embodiments, the information of the user comprises demographical information. In some embodiments, the encoded response may include one or more number, letter, symbol, or a combination thereof. In some embodiments, analyzing the pattern and a plurality of patterns comprises generating a histogram of the pattern and the plurality of patterns. In some embodiments, the histogram indicates a frequency of occurrence of one or more responses among the plurality of responses based on the pattern and the plurality of patterns. In some embodiments, each of the plurality of responses is uniquely associated with a pre-determined pattern. In some embodiments, at least two among the response and the plurality of responses are not independent. In some embodiments, the pre-determined set of rules comprises one or more of: base-2 numbering rules, base-10 numbering rules, base-8 numbering rules, and base-16 numbering rules. In some embodiments, the generative assessment item is related to science, technology, engineering, and mathematics (STEM). In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level.

In yet another aspect, disclosed herein are non-transitory computer-readable storage media encoded with a computer program including instructions executable by a processor to create an application comprising: a software module obtaining a released assessment item, wherein the released assessment item comprising a correct answer or a combination of correction answers; a software module generating a question for the generative assessment item, wherein the question comprises information in the correct answer or the combination correction of answers; and a software module generating a plurality of responses to the question for the generative assessment item, wherein the plurality of responses comprises at least two responses that are not independent, and wherein the plurality of responses are non-dichotomous.

In yet another aspect, disclosed herein are non-transitory computer-readable storage media encoded with a computer program including instructions executable by a processor to create an application comprising: a software module generating a plurality of responses to a question of the generative assessment item, wherein the plurality of responses comprises at least two responses that are not independent, and wherein the plurality of responses are non-dichotomous; and a software module developing a set of rules for encoding the plurality of responses, wherein encoding of the plurality of responses generates a plurality of patterns, each pattern uniquely represent a response of the plurality of responses, wherein the plurality of patterns comprising: one or more first patterns representing baseline understanding of the question; one or more second patterns representing accurate understanding of the question; and one or more third patterns representing intermediate understanding of the question.

In yet another aspect, disclosed herein are non-transitory computer-readable storage media encoded with a computer program including instructions executable by a processor to create an application comprising: a software module receiving a response to the generative assessment item from a user, wherein the response is selected by the user among a plurality of responses; a software module encoding the response with a pre-determined set of rules thereby generating an encoded response, the encoded response comprising a pattern, wherein the pattern uniquely represents the response; and a software module analyzing the pattern and a plurality of patterns, the plurality of patterns corresponding to at least a portion of the plurality of responses to the generative assessment item.

In some embodiments, the generative assessment item is one or more of: a task, an assignment, an activity, a multiple choice question, and an order list question. In some embodiments, the generative assessment item is a non-dichotomous item. In some embodiments, when scored non-dichotomously, the plurality of responses contains at least 2×, 4×, 8×, or 16× information than scoring the plurality of responses dichotomously. In some embodiments, the media further comprises a software module providing a generative assessment item to a user. In some embodiments, a software module providing a generative assessment item to a user comprises presenting a generative assessment item in a group-based cloud computing system. In some embodiments, the media further comprises a software module receiving the response to the generative assessment item from the user in a group-based cloud computing system. In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, at least one of the number of virtual classrooms are author-able at a group activity level and at a learner level. In some embodiments, the media further comprises allowing the user to: create a coded object or behavior, post an image with embedded code in a gallery, select an object from the gallery to be added to the user's work space, or a combination thereof. In some embodiments, the media further comprises allowing the user or an activity author to select when and to whom a student space or a group-shared space is available. In some embodiments, the media further comprises allowing the user to turn on or off updates in the student space or the group-shared space. In some embodiments, the student space or the group-shared space is virtual space accessible by the user via a user interface. In some embodiments, the media further comprising allowing the user to code using one or more agent-based modeling languages. In some embodiments, the additional encoding is based on information of the user. In some embodiments, the information of the user comprises demographic information. In some embodiments, the encoded response may include one or more number, letter, symbol, or a combination thereof. In some embodiments, analyzing the pattern and a plurality of patterns comprises generating a histogram of the pattern and the plurality of patterns. In some embodiments, the histogram indicates a frequency of occurrence of one or more responses among the plurality of responses based on the pattern and the plurality of patterns. In some embodiments, each of the plurality of responses is uniquely associated with a pre-determined pattern. In some embodiments, at least two among the response and the plurality of responses are not independent. In some embodiments, the pre-determined set of rules comprises one or more of: base-2 numbering rules, base-10 numbering rules, base-8 numbering rules, and base-16 numbering rules. In some embodiments, the generative assessment item is related to science, technology, engineering, and mathematics (STEM). In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level.

Another aspect provided herein is a computer-implemented method of training one or more machine learning algorithms to identify an existence of a characteristic, a probability of the existence of the characteristic, or both for each a plurality of students comprising: collecting a first plurality and a second plurality of sets of concatenated answers wherein each of the first plurality of sets of concatenated answers is associated with one of the plurality of students having the characteristic, and wherein each of the second plurality of sets of concatenated answers is associated with one of the plurality of students lacking the characteristic; creating a first training set comprising the collected sets of concatenated answers; training the machine learning algorithm in a first stage using the first training set; creating a second training set for a second stage of training comprising the first training set and the sets of concatenated answers associated with students lacking the characteristic that are incorrectly detected as having the characteristic after the first stage of training; and training the machine learning algorithm in a second stage using the second training set.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, the set of concatenated answers comprises a series of two or more answer choices to each of a plurality of non-dichotomous generative assessment items. In some embodiments, each answer choice is in a binary format, wherein an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a computer-implemented system for training one or more machine learning algorithms to identify a presence of a characteristic, a probability of the presence of the characteristic, or both for each a plurality of students, the system comprising: a computer-readable storage device coupled to at least one processor and having instructions stored thereon which, when executed by the at least one processor, causes the at least one processor to perform at least the following: collecting a first plurality and a second plurality of sets of concatenated answers wherein each of the first plurality of sets of concatenated answers is associated with one of the plurality of students having the characteristic, and wherein each of the second plurality of sets of concatenated answers is associated with one of the plurality of students lacking the characteristic; creating a first training set comprising the collected sets of concatenated answers; training the machine learning algorithm in a first stage using the first training set; creating a second training set for a second stage of training comprising the first training set and the sets of concatenated answers associated with students lacking the characteristic that are incorrectly detected as having the characteristic after the first stage of training; and training the machine learning algorithm in a second stage using the second training set.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, the set of concatenated answers comprises a series of two or more answer choices to each of a plurality of non-dichotomous generative assessment items. In some embodiments, each answer choice is in a binary format, wherein an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a non-transitory computer-readable storage media encoded with a computer program including instructions executable by a processor to create an application to train one or more machine learning algorithms to identify a presence of a characteristic, a probability of the presence of the characteristic, or both for each a plurality of students, the application performing at least the following: collecting a first plurality and a second plurality of sets of concatenated answers wherein each of the first plurality of sets of concatenated answers is associated with one of the plurality of students having the characteristic, and wherein each of the second plurality of sets of concatenated answers is associated with one of the plurality of students lacking the characteristic; creating a first training set comprising the collected sets of concatenated answers; training the machine learning algorithm in a first stage using the first training set; creating a second training set for a second stage of training comprising the first training set and the sets of concatenated answers associated with students lacking the characteristic that are incorrectly detected as having the characteristic after the first stage of training; and training the machine learning algorithm in a second stage using the second training set.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, the set of concatenated answers comprises a series of two or more answer choices to each of a plurality of non-dichotomous generative assessment items. In some embodiments, each answer choice is in a binary format, wherein an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a computer-implemented method of training one or more machine learning algorithms to identify a presence of a characteristic, a probability of the presence of the characteristic, or both for each a plurality of students comprising: receiving two or more answer selections for each of a plurality of non-dichotomous generative assessment items for each of the plurality of students; concatenating the answer selections for each of the plurality of non-dichotomous generative assessment item and for each of the plurality of students to form a set of concatenated answers; creating a first training set comprising the set of concatenated answers, a first portion of the set of concatenated answers associated with students having the characteristic, and a second portion of the set of concatenated answers associated with students lacking the characteristic; training the machine learning algorithm in a first stage using the first training set; creating a second training set for a second stage of training comprising the first training set and the sets of concatenated answers associated with students lacking the characteristic that are incorrectly detected as having the characteristic after the first stage of training; and training the machine learning algorithm in a second stage using the second training set.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a computer-implemented system for training one or more machine learning algorithms to identify a presence of a characteristic, a probability of the presence of the characteristic, or both for each a plurality of students, the system comprising: a computer-readable storage device coupled to at least one processor and having instructions stored thereon which, when executed by the at least one processor, causes the at least one processor to perform at least the following: receiving two or more answer selections for each of a plurality of non-dichotomous generative assessment items for each of the plurality of students; concatenating the answer selections for each of the plurality of non-dichotomous generative assessment item and for each of the plurality of students to form a set of concatenated answers; creating a first training set comprising the set of concatenated answers, a first portion of the set of concatenated answers associated with students having the characteristic, and a second portion of the set of concatenated answers associated with students lacking the characteristic; training the machine learning algorithm in a first stage using the first training set; creating a second training set for a second stage of training comprising the first training set and the sets of concatenated answers associated with students lacking the characteristic that are incorrectly detected as having the characteristic after the first stage of training; and training the machine learning algorithm in a second stage using the second training set.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter.

In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a non-transitory computer-readable storage media encoded with a computer program including instructions executable by a processor to create an application to train one or more machine learning algorithms to identify a presence of a characteristic, a probability of the presence of the characteristic, or both for each a plurality of students, the application performing at least the following: receiving two or more answer selections for each of a plurality of non-dichotomous generative assessment items for each of the plurality of students; concatenating the answer selections for each of the plurality of non-dichotomous generative assessment item and for each of the plurality of students to form a set of concatenated answers; creating a first training set comprising the set of concatenated answers, a first portion of the set of concatenated answers associated with students having the characteristic, and a second portion of the set of concatenated answers associated with students lacking the characteristic; training the machine learning algorithm in a first stage using the first training set; creating a second training set for a second stage of training comprising the first training set and the sets of concatenated answers associated with students lacking the characteristic that are incorrectly detected as having the characteristic after the first stage of training; and training the machine learning algorithm in a second stage using the second training set.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a computer-implemented method of identifying a presence of a characteristic, a probability of the presence of the characteristic, or both for each a plurality of students comprising: receiving two or more answer selections for each of a plurality of non-dichotomous generative assessment items for each of the plurality of students; concatenating the answer selections for each of the plurality of non-dichotomous generative assessment item and for each of the plurality of students to form a set of concatenated answers; and running a machine algorithm on the plurality of sets of concatenated answers to identify the presence of a characteristic, a probability of the presence of the characteristic, or both for each a plurality of students.

In some embodiments, the machine algorithm is trained by the method, system, or media of any previous claim. In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a computer-implemented system for identifying a presence of a characteristic, a probability of the presence of the characteristic, or both for each a plurality of students comprising, the system comprising: a computer-readable storage device coupled to at least one processor and having instructions stored thereon which, when executed by the at least one processor, causes the at least one processor to perform at least the following: receiving two or more answer selections for each of a plurality of non-dichotomous generative assessment items for each of the plurality of students; concatenating the answer selections for each of the plurality of non-dichotomous generative assessment item and for each of the plurality of students to form a set of concatenated answers; and running a machine algorithm on the plurality of sets of concatenated answers to identify the presence of a characteristic, a probability of the presence of the characteristic, or both for each a plurality of students.

In some embodiments, the machine algorithm is trained by the method, system, or media of any previous claim. In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

Another aspect provided herein is a non-transitory computer-readable storage media encoded with a computer program including instructions executable by a processor to create an application to identifying a presence of a characteristic, a probability of the presence of the characteristic, or both for each a plurality of students, the application performing at least the following: receiving two or more answer selections for each of a plurality of non-dichotomous generative assessment items for each of the plurality of students; concatenating the answer selections for each of the plurality of non-dichotomous generative assessment item and for each of the plurality of students to form a set of concatenated answers; and running a machine algorithm on the plurality of sets of concatenated answers to identify the presence of a characteristic, a probability of the presence of the characteristic, or both for each a plurality of students.

In some embodiments, the machine algorithm is trained by the method, system, or media of any previous claim. In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof. In some embodiments, an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

BRIEF DESCRIPTION OF THE DRAWINGS

A better understanding of the features and advantages of the present subject matter will be obtained by reference to the following detailed description that sets forth illustrative embodiments and the accompanying drawings of which:

FIG. 3 shows a first non-limiting examples of a generative assessment item;

FIG. 4 shows a second non-limiting examples of a generative assessment item;

FIG. 5 shows a third non-limiting examples of a generative assessment item;

FIG. 6 shows a fourth non-limiting examples of a generative assessment item;

FIG. 7 shows a fifth non-limiting examples of a generative assessment item;

FIG. 8 shows a sixth non-limiting examples of a generative assessment item;

FIG. 9 shows a seventh non-limiting examples of a generative assessment item;

FIG. 10 shows an eighth non-limiting examples of a generative assessment item;

FIG. 12 shows a tenth non-limiting examples of a generative assessment item;

FIG. 13 shows an eleventh non-limiting examples of a generative assessment item;

FIG. 14 shows a twelfth non-limiting examples of a generative assessment item;

FIG. 16 shows a fourteenth non-limiting examples of a generative assessment item;

FIG. 17 shows a fifteenth non-limiting examples of a generative assessment item;

FIG. 18 shows a sixteenth non-limiting examples of a generative assessment item;

FIG. 19 shows a seventeenth non-limiting examples of a generative assessment item;

FIG. 21 shows a nineteenth non-limiting examples of a generative assessment item;

FIG. 23 shows a twenty-first non-limiting examples of a generative assessment item;

FIG. 24 shows a twenty-second non-limiting examples of a generative assessment item;

FIG. 26 shows a twenty-fourth non-limiting examples of a generative assessment item;

FIG. 27 shows a twenty-fifth non-limiting examples of a generative assessment item;

FIG. 29 shows a twenty-seventh non-limiting examples of a generative assessment item;

FIG. 30 shows a twenty-eighth non-limiting examples of a generative assessment item;

FIG. 31 shows a twenty-ninth non-limiting examples of a generative assessment item;

FIG. 33 shows a thirty-first non-limiting examples of a generative assessment item;

FIG. 36 shows a thirty-fourth non-limiting examples of a generative assessment item;

FIG. 42 shows a non-limiting table of a current single select multiple choice test across students;

FIG. 45A shows a first non-limiting table displaying the scoring of a first single select multiple choice test across students;

FIG. 45B shows a second non-limiting table displaying the scoring of a first single select multiple choice test across students;

FIG. 48 shows a first non-limiting table displaying a plurality of concatenated responses;

FIG. 49A shows a second non-limiting table displaying a plurality of concatenated responses;

FIG. 49B shows a third non-limiting table displaying a plurality of concatenated responses;

FIG. 49C shows a fourth non-limiting table displaying a plurality of concatenated responses;

FIG. 50 shows a non-limiting table displaying a concatenated scoring of a pattern-based test across two questions;

FIG. 51A shows a non-limiting table displaying the scoring of a pattern-based test across a plurality of non-dichotomous generative assessment items;

FIG. 51B shows a non-limiting table displaying the scoring of a pattern-based test across a plurality of students;

FIG. 52 shows a non-limiting table displaying the scoring of a pattern-based test across a plurality of non-dichotomous generative assessment items and a plurality of students;

FIG. 53 shows a non-limiting table displaying student responses associated with a class label attribute;

FIG. 54 shows a non-limiting table displaying the detection of patterns in student responses associated with a class label attribute;

FIG. 56 shows a non-limiting diagram of a method of training, performing, and comparing a plurality of machine learning algorithms to identify an existence of a characteristic, a probability of the existence of the characteristic, or both for each a plurality of students;

FIG. 60 shows an exemplary algorithm for machine learning reliability testing;

FIG. 62 shows an exemplary algorithm for performing SVM and RF machine learning algorithms;

FIG. 63 shows the accuracy statistics for an exemplary SVM machine learning algorithm; and FIG. 64 shows the accuracy statistics for an exemplary RF machine learning algorithm.

DETAILED DESCRIPTION OF THE INVENTION

In some embodiments, the non-dichotomous generative assessment items herein enable the collection and storage of more information regarding a student answer, in a format that is compact and easy to process, to enable identification of meaningful patterns in student responses. In some embodiments, the non-dichotomous generative assessment items herein enable analysis of frequency or relative presence and allow for the conveyance of partial credit. In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level.

Provided herein are non-dichotomous answer processing media, system, and methods for e-learning applications comprising: a prompt module, a recording module, a storage module, and a concatenation module. In some embodiments, the prompt module displays a non-dichotomous generative assessment item. In some embodiments, the non-dichotomous generative assessment item comprises a series of two or more answer choices. In some embodiments, the recording module receives a student answer to each answer choice in the series. In some embodiments, each student answer comprises an answer selection or an answer non-selection. In some embodiments, the storage module stores the received student answer to each answer choice. In some embodiments, the storage module stores the received student answer to each answer choice in the series in a binary format. In some embodiments, any answer selection is stored as a first binary number and any answer non-selection is stored as a second binary number. In some embodiments, the concatenation module concatenates every binarily stored student answer in the series. In some embodiments, the concatenation module concatenates every binarily stored student answer in the series to form a concatenated answer. In some embodiments, the concatenated answer does not comprise a delimiter. In some embodiments, the two or more answer choices comprise 3, 4, 5, 6, 7, 8, 9, 10 or more answer choices.

Figure 40:
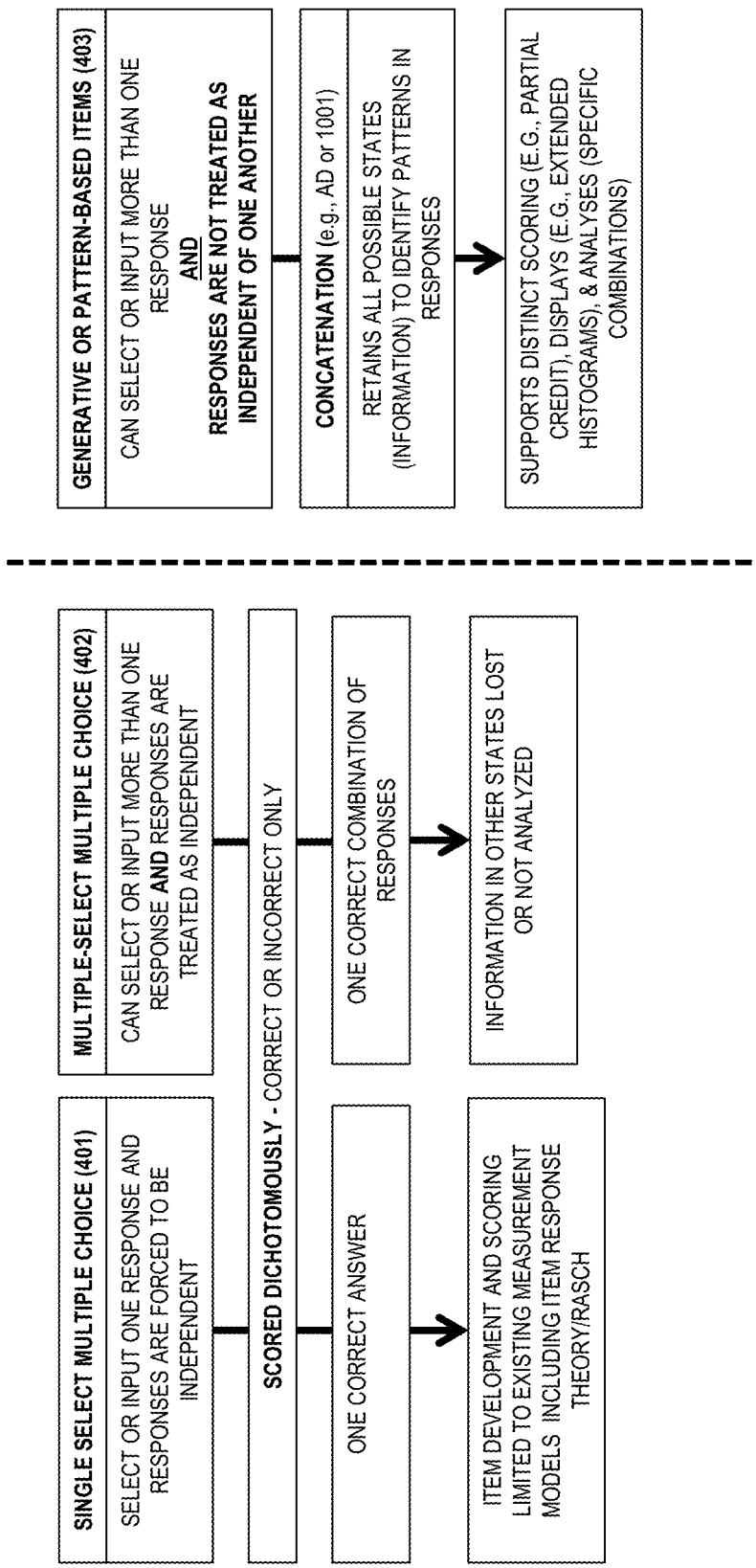
FIG. 40 shows a first non-limiting schematic diagram of dichotomous and non-dichotomous generative or pattern-based systems.
Figure 41:
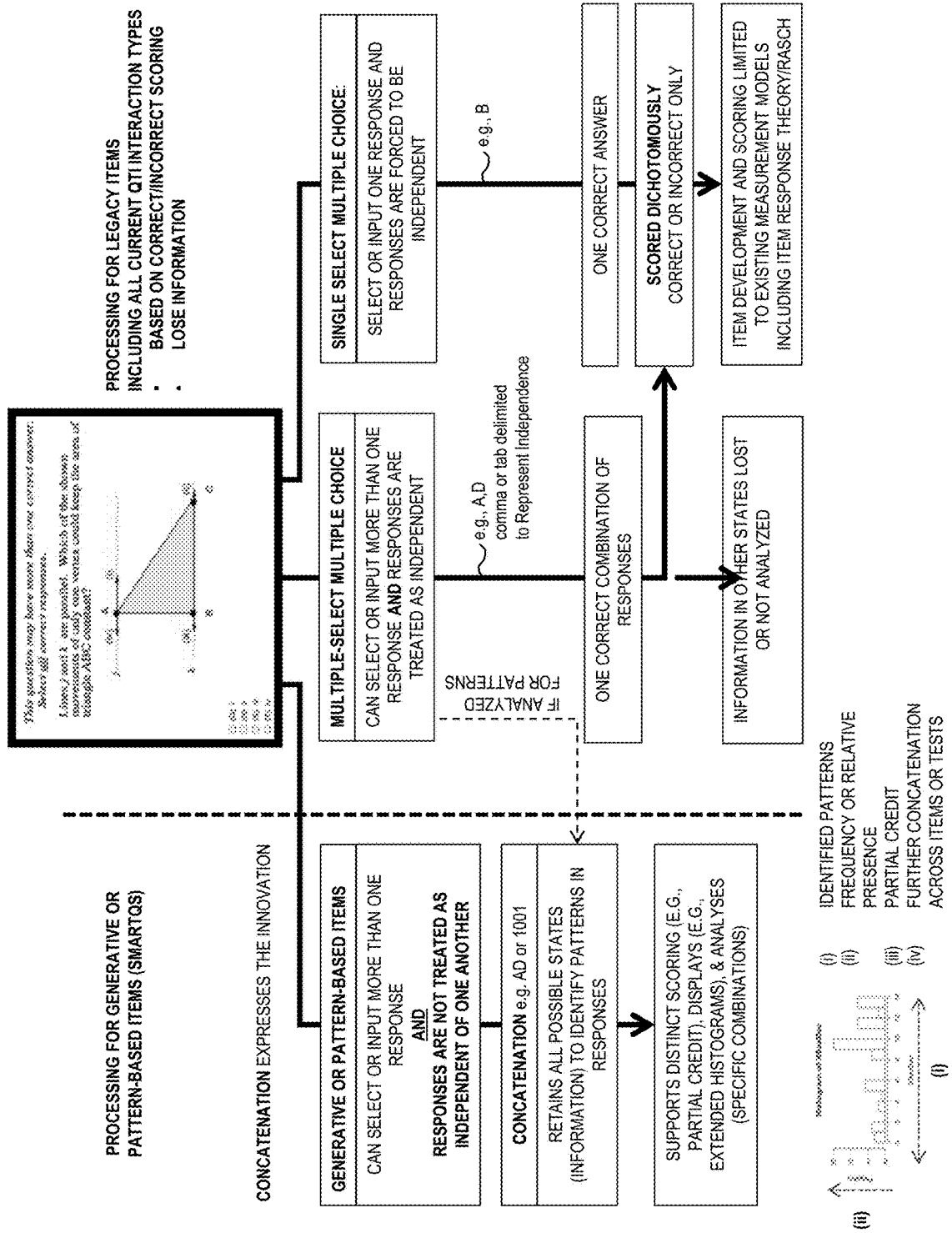
FIG. 41 shows a second non-limiting schematic diagram of dichotomous and non-dichotomous generative or pattern-based systems.

As seen in FIG. 40, current single select multiple choice 401 and multiple-select multiple choice tests 402 scored dichotomously, whereas only a correct or incorrect indication is stored. For the current single select multiple choice tests 401 the item comprises a series of two or more answer choices, wherein each answer choice is independent, and wherein only one student answer is able to be submitted and recorded by the test. As such, the current single select multiple choice tests 401 compare the answer choice to one correct response to determine whether or not the answer choice is correct. However, for the current single select multiple choice tests 401 item development and scoring is limited to existing measurement models such as item response theory. An exemplary scoring for the current single select multiple choice tests is shown in FIG. 42, wherein a single dichotomous item comprises four answer choices, and wherein each of the five students select only one student answer. As student 3 is the only student to select the correct answer of "B" they are the only person to receive a score for their answer.

Figure 43:
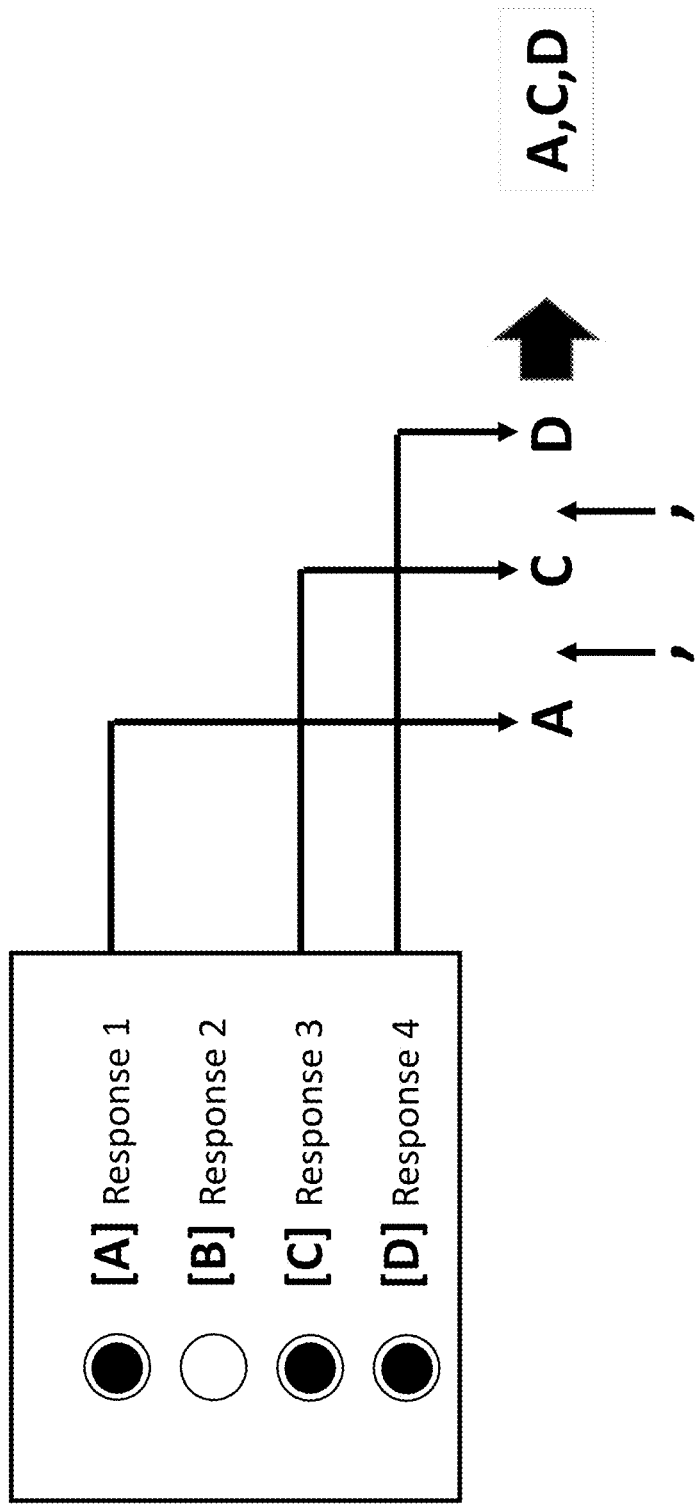
FIG. 43 shows a non-limiting first schematic diagram of a first current multiple-select multiple choice test.
Figure 44:
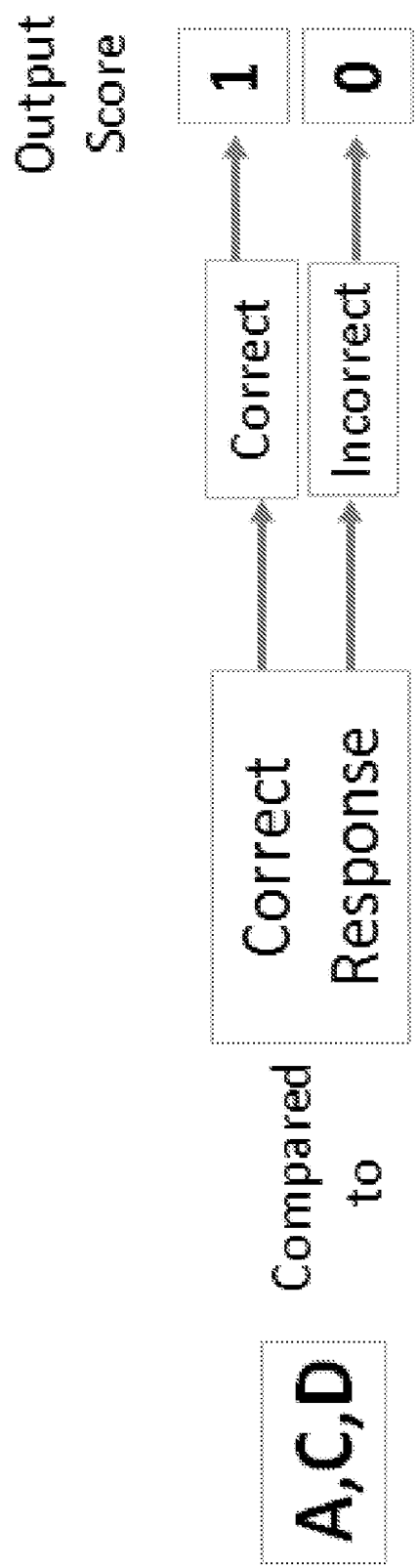
FIG. 44 shows a non-limiting second schematic diagram of a first current multiple-select multiple choice test.

For multiple-select multiple choice tests 402, a dichotomous item comprises a series of two or more answer choices, wherein one or more student answer are able to be submitted and recorded by the test, and wherein each answer choice is independent. As such, after being scored dichotomously, the current multiple select multiple choice tests 402 compare the answer choice or choices to one correct response to determine whether or not the answer choice or choices are correct. Thereafter, the answer choice or choices, the determination, or both are stored for each dichotomous item. However, for the current multiple select multiple choice tests 402 information in other states lost or not analyzed. An exemplary schematic diagram for a first current multiple select multiple choice tests is shown in FIG. 43, wherein a single dichotomous item comprises four answer choices, wherein the current multiple select multiple choice test 402 receives one student answer to each answer choice, and wherein each student answer comprises an answer selection. In the exemplary first schematic, student answers are stored regarding answer choices A, C, and D. As such, the current multiple select multiple choice test 402 adds a delimiter between each student answer and stores the response as "A, C, D." Per FIG. 44 the current multiple select multiple choice test 402 then compares the student answer to the correct response and assigns an output score depending on whether or not the student answers are correct. The current multiple select multiple choice test 402 then stores only the output scores and discards the original student answer(s).

FIG. 45A shows exemplary responses by 5 students test, whereas student answers for student 1 are temporarily stored regarding answer choices A, B, and C, whereas student answers for student 2 are temporarily stored regarding answer choices B and C, whereas student answers for student 3 are temporarily stored regarding answer choices A and D, whereas no student answers for student 4 are stored, and whereas student answers for student 5 are temporarily stored regarding answer choices C and D. As such, the answers are temporarily stored for students 1-5 as "A, B, C" "B, C" "A, D" " " and "C, D" respectfully with delimiters and immediately deleted after scoring. Per FIG. 45B each of the students are assigned a score whereas only student 2 receives a score of one for correctly submitting answer choices B and C. As shown, student 1's score does not represent that student 1 correctly selected answer choices B and C. In the case shown therein, with four answer choices there are 16 possible combinations of student answers and 16 possible bits of information, whereas only one bit of data regarding the student answers is stored. Such a loss of information prevents future analysis, correlations, and student answer recreation.

Figure 46:
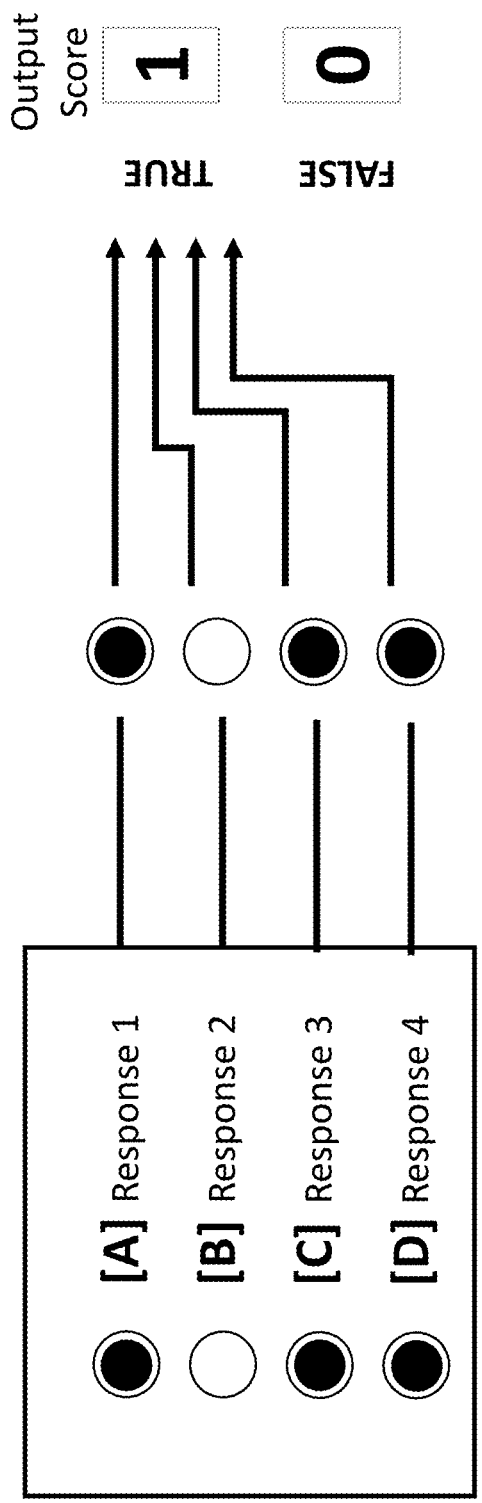
FIG. 46 shows a non-limiting schematic diagram of a second current multiple-select multiple choice test.

An exemplary schematic diagram for a second current multiple select multiple choice test is shown in FIG. 46, wherein a single dichotomous item comprises four answer choices, wherein the current multiple select multiple choice test 402 receives one student answer to each answer choice, and wherein the second current multiple select multiple choice test determines whether the student answer to each of the four answer choices is correct or not correct. The second current multiple select multiple choice test individual student answers are directly compared to a correct selection. The second current multiple select multiple choice test does not store the student answers, wherein such information is lost. In the case shown therein, with four answer choices there are 16 possible combinations of student answers and 16 possible bits of information, whereas only one bit of data regarding the student answers is stored. Such a loss of information prevents future analysis, correlations, and student answer recreation.

Figure 47:
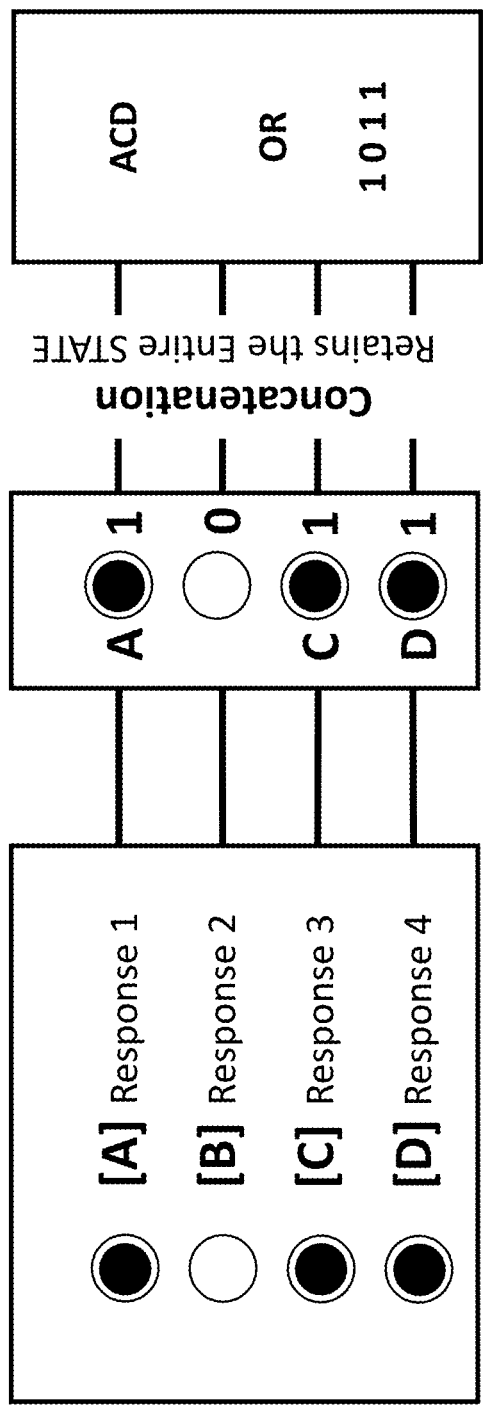
FIG. 47 shows a non-limiting schematic diagram of a non-dichotomous generative assessment system.

By contrast, per the pattern-based tests of FIG. 47 as disclosed herein, a non-limiting example of a non-dichotomous generative assessment item is provided. Here, the non-dichotomous generative assessment item comprises a series of two or more answer choices, wherein zero, one, or more student answer may be submitted and recorded by the test, and wherein each answer choice is not independent. In this particular example, 16 possible states exist (see, e.g., Table 1). As shown therein, answer choices of A, C, and D are represented as 1011. As such, after concatenation of the answer choices, the multiple select multiple choice test retains all possible states (information) to identify patterns in responses and supports distinct scoring (e.g., partial credit), enables the formation and display of answer choice histograms, and enables analyses of answer choice response combinations. In some embodiments, the pattern-based test does not use a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices.

In one aspect, disclosed herein are computer-implemented methods for generative assessment item development, the method comprising: obtaining a released assessment item, wherein the released assessment item comprising a correct answer or a combination of correction answers; generating a question for the generative assessment item, wherein the question comprises information in the correct answer or the combination correction of answers of the released assessment item; and generating a plurality of responses to the question for the generative assessment item, wherein the plurality of responses comprises at least two responses that are not independent, and wherein the plurality of responses are non-dichotomous.

In another aspect, disclosed herein are computer-implemented methods for generative assessment item analysis, the method comprising: generating, by a computer, a plurality of responses to a question of the generative assessment item, wherein the plurality of responses comprises at least two responses that are not independent, and wherein the plurality of responses are non-dichotomous; and developing a set of rules for encoding the plurality of responses, wherein encoding of the plurality of responses generates a plurality of patterns, each pattern uniquely represent a response of the plurality of responses, wherein the plurality of patterns comprising: one or more first patterns representing baseline understanding of the question; one or more second patterns representing accurate understanding of the question; and one or more third patterns representing intermediate understanding of the question.

In yet another aspect, disclosed herein are computer-implemented methods for generative assessment item analysis, the method comprising: receiving, by a computer, a response to the generative assessment item from a user, wherein the response is selected by the user among a plurality of responses; encoding, by the computer, the response with a pre-determined set of rules thereby generating an encoded response, the encoded response comprising a pattern, wherein the pattern uniquely represents the response; and analyzing, by the computer, the pattern and a plurality of patterns, the plurality of patterns corresponding to at least a portion of the plurality of responses to the generative assessment item.

In some embodiments, the method further comprises receiving the response to the generative assessment item from the user in a group-based cloud computing system. In some embodiments, the generative assessment item is one or more of: a task, an assignment, an activity, a multiple choice question, and an order list question. In some embodiments, the generative assessment item is a non-dichotomous item. In some embodiments, when scored non-dichotomously, the plurality of responses contains at least 2×, 4×, 8×, or 16× information than scoring the plurality of responses dichotomously. In some embodiments, the method herein further comprises providing a generative assessment item to a user. In some embodiments, providing a generative assessment item to a user comprises presenting a generative assessment item in a group-based cloud computing system. In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, at least one of the numbers of virtual classrooms is author-able at a group activity level and at a learner level. In some embodiments, the method further comprises allowing the user to: create a coded object or behavior, post an image with embedded code in a gallery, select an object from the gallery to be added to the user's work space, or a combination thereof. In some embodiments, the method further comprises allowing the user or an activity author to select when and to whom a student space or a group-shared space is available. In some embodiments, the method further comprises allowing the user to turn on or off updates in the student space or the group-shared space. In some embodiments, the student space or the group-shared space is virtual space accessible by the user via a user interface. In some embodiments, the method further comprises allowing the user to code using one or more agent-based modeling languages. In some embodiments, the method further comprises combining an additional encoding with the encoded response to generate a second encoded response. In some embodiments, the additional encoding is based on information of the user. In some embodiments, the information of the user comprises demographical information. In some embodiments, the encoded response may include one or more number, letter, symbol, or a combination thereof. In some embodiments, analyzing the pattern and a plurality of patterns comprises generating a histogram of the pattern and the plurality of patterns. In some embodiments, the histogram indicates a frequency of occurrence of one or more responses among the plurality of responses based on the pattern and the plurality of patterns. In some embodiments, each of the plurality of responses is uniquely associated with a pre-determined pattern. In some embodiments, at least two among the response and the plurality of responses are not independent. In some embodiments, the pre-determined set of rules comprises one or more of: base-2 numbering rules, base-10 numbering rules, base-8 numbering rules, and base-16 numbering rules. In some embodiments, the generative assessment item is related to science, technology, engineering, and mathematics (STEM). In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level.

In yet another aspect, disclose herein are computer-implemented systems for generative assessment item development, the system comprising: a digital processing device comprising: at least one processor, an operating system configured to perform executable instructions, a memory, and a computer program including instructions executable by the digital processing device to create an application comprising: a software module obtaining a released assessment item, wherein the released assessment item comprising a correct answer or a combination of correction answers; a software module generating a question for the generative assessment item, wherein the question comprises information in the correct answer or the combination correction of answers; and a software module generating a plurality of responses to the question for the generative assessment item, wherein the plurality of responses comprises at least two responses that are not independent, and wherein the plurality of responses are non-dichotomous.

In yet another aspect, disclose herein are computer-implemented systems for generative assessment item development, the system comprising: a digital processing device comprising: at least one processor, an operating system configured to perform executable instructions, a memory, and a computer program including instructions executable by the digital processing device to create an application comprising: a software module generating a plurality of responses to a question of the generative assessment item, wherein the plurality of responses comprises at least two responses that are not independent, and wherein the plurality of responses are non-dichotomous; and a software module developing a set of rules for encoding the plurality of responses, wherein encoding of the plurality of responses generates a plurality of patterns, each pattern uniquely represent a response of the plurality of responses, wherein the plurality of patterns comprising: one or more first patterns representing baseline understanding of the question; one or more second patterns representing accurate understanding of the question; and one or more third patterns representing intermediate understanding of the question.

In yet another aspect, disclose herein are computer-implemented systems for generative assessment item development, the system comprising: a digital processing device comprising: at least one processor, an operating system configured to perform executable instructions, a memory, and a computer program including instructions executable by the digital processing device to create an application comprising: a software module receiving a response to the generative assessment item from a user, wherein the response is selected by the user among a plurality of responses; a software module encoding the response with a pre-determined set of rules thereby generating an encoded response, the encoded response comprising a pattern, wherein the pattern uniquely represents the response; and a software module analyzing the pattern and a plurality of patterns, the plurality of patterns corresponding to at least a portion of the plurality of responses to the generative assessment item.

In some embodiments, the generative assessment item is one or more of: a task, an assignment, an activity, a multiple choice question, and an order list question. In some embodiments, the generative assessment item is a non-dichotomous item. In some embodiments, when scored non-dichotomously, the plurality of responses contains at least $2\times$, $4\times$, $8\times$, or $16\times$ information than scoring the plurality of responses dichotomously. In some embodiments, the system herein further comprises a software module providing a generative assessment item to a user. In some embodiments, providing a generative assessment item to a user comprises presenting a generative assessment item in a group-based cloud computing system. In some embodiments, the system further comprises a software module receiving the response to the generative assessment item from the user in a group-based cloud computing system. In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, at least one of the number of virtual classrooms are author-able at a group activity level and at a learner level. In some embodiments, the system further comprises allowing the user to: create a coded object or behavior, post an image with embedded code in a gallery, select an object from the gallery to be added to the user's work space, or a combination thereof. In some embodiments, further comprises allowing the user or an activity author to select when and to whom a student space or a group-shared space is available. In some embodiments, the system further comprises allowing the user to turn on or off updates in the student space or the group-shared space. In some embodiments, the student space or the group-shared space is virtual space accessible by the user via a user interface. In some embodiments, the system further comprises allowing the user to code using one or more agent-based modeling languages. In some embodiments, the system further comprises a software module combining an additional encoding with the encoded response to generate a second encoded response. In some embodiments, the additional encoding is based on information of the user. In some embodiments, the information of the user comprises demographical information. In some embodiments, the encoded response may include one or more number, letter, symbol, or a combination thereof. In some embodiments, analyzing the pattern and a plurality of patterns comprises generating a histogram of the pattern and the plurality of patterns. In some embodiments, the histogram indicates a frequency of occurrence of one or more responses among the plurality of responses based on the pattern and the plurality of patterns. In some embodiments, each of the plurality of responses is uniquely associated with a pre-determined pattern. In some embodiments, at least two among the response and the plurality of responses are not independent. In some embodiments, the pre-determined set of rules comprises one or more of: base-2 numbering rules, base-10 numbering rules, base-8 numbering rules, and base-16 numbering rules. In some embodiments, the generative assessment item is related to science, technology, engineering, and mathematics (STEM). In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level.

In yet another aspect, disclosed herein are non-transitory computer-readable storage media encoded with a computer program including instructions executable by a processor to create an application comprising: a software module obtaining a released assessment item, wherein the released assessment item comprising a correct answer or a combination of correction answers; a software module generating a question for the generative assessment item, wherein the question comprises information in the correct answer or the combination correction of answers; and a software module generating a plurality of responses to the question for the generative assessment item, wherein the plurality of responses comprises at least two responses that are not independent, and wherein the plurality of responses are non-dichotomous.

In yet another aspect, disclosed herein are non-transitory computer-readable storage media encoded with a computer program including instructions executable by a processor to create an application comprising: a software module generating a plurality of responses to a question of the generative assessment item, wherein the plurality of responses comprises at least two responses that are not independent, and wherein the plurality of responses are non-dichotomous; and a software module developing a set of rules for encoding the plurality of responses, wherein encoding of the plurality of responses generates a plurality of patterns, each pattern uniquely represent a response of the plurality of responses, wherein the plurality of patterns comprising: one or more first patterns representing baseline understanding of the question; one or more second patterns representing accurate understanding of the question; and one or more third patterns representing intermediate understanding of the question.

In yet another aspect, disclosed herein are non-transitory computer-readable storage media encoded with a computer program including instructions executable by a processor to create an application comprising: a software module receiving a response to the generative assessment item from a user, wherein the response is selected by the user among a plurality of responses; a software module encoding the response with a pre-determined set of rules thereby generating an encoded response, the encoded response comprising a pattern, wherein the pattern uniquely represents the response; and a software module analyzing the pattern and a plurality of patterns, the plurality of patterns corresponding to at least a portion of the plurality of responses to the generative assessment item.

In some embodiments, the generative assessment item is one or more of: a task, an assignment, an activity, a multiple choice question, and an order list question. In some embodiments, the generative assessment item is a non-dichotomous item. In some embodiments, when scored non-dichotomously, the plurality of responses contains at least 2×, 4×, 8×, or 16× information than scoring the plurality of responses dichotomously. In some embodiments, the media further comprises a software module providing a generative assessment item to a user. In some embodiments, a software module providing a generative assessment item to a user comprises presenting a generative assessment item in a group-based cloud computing system. In some embodiments, the media further comprises a software module receiving the response to the generative assessment item from the user in a group-based cloud computing system. In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, at least one of the number of virtual classrooms are author-able at a group activity level and at a learner level. In some embodiments, the media further comprises allowing the user to: create a coded object or behavior, post an image with embedded code in a gallery, select an object from the gallery to be added to the user's work space, or a combination thereof. In some embodiments, the media further comprises allowing the user or an activity author to select when and to whom a student space or a group-shared space is available. In some embodiments, the media further comprises allowing the user to turn on or off updates in the student space or the group-shared space. In some embodiments, the student space or the group-shared space is virtual space accessible by the user via a user interface. In some embodiments, the media further comprising allowing the user to code using one or more agent-based modeling languages. In some embodiments, the additional encoding is based on information of the user. In some embodiments, the information of the user comprises demographical information. In some embodiments, the encoded response may include one or more number, letter, symbol, or a combination thereof. In some embodiments, analyzing the pattern and a plurality of patterns comprises generating a histogram of the pattern and the plurality of patterns. In some embodiments, the histogram indicates a frequency of occurrence of one or more responses among the plurality of responses based on the pattern and the plurality of patterns. In some embodiments, each of the plurality of responses is uniquely associated with a pre-determined pattern. In some embodiments, at least two among the response and the plurality of responses are not independent. In some embodiments, the pre-determined set of rules comprises one or more of: base-2 numbering rules, base-10 numbering rules, base-8 numbering rules, and base-16 numbering rules. In some embodiments, the generative assessment item is related to science, technology, engineering, and mathematics (STEM). In some embodiments, the generative assessment item is related to one or more of algebra, physics, geometry, pre-calculus, calculus, statistics, biology, chemistry, civil engineering, electronics, and architecture. In some embodiments, the generative assessment item is related to math, writing, history, reading, literature, science, art, music, foreign language, and social studies. In some embodiments, the generative assessment item is related to a level of learning for a kindergartener level, a first grade level, a second grade level, a third grade level, a fourth grade level, a fifth grade level, a sixth grade level, a seventh grade level, an eighth grade level, a ninth grade level, a tenth grade level, an eleventh grade level, a twelfth grade level, a college level, or post-graduate level.

Generative Assessment Items

Disclosed herein are items for education purposes. In some embodiments, items are tasks, activities, or assignments to which a user responds for the purposes of assessment. Items can include tasks, activities or assignments where users selects from among a given set of responses (e.g., a multiple choice question, or an order list question), where users generate a response or collection of responses that can be directly encoded or categorized, where users respond with gestures or sequences of gestures that can be encoded or categorized and/or where the users responses or set of responses need to be parsed or otherwise analyzed prior to being encoded or categorized (e.g., graph sketched by a user is first parsed into piecewise elements based on curvature prior to being further encoded and analyzed; or text parsed in terms of active and passive verb tenses or use of specific vocabulary). In some embodiments, the response of a user to a generative assessment item may include one or more alternatives provided as solutions to the stem of the item. For example, a user may provide a response of (a) and (c) to a multiple choice question, while another user may provide (b) to the same multiple choice question.

In some embodiments, the systems, methods, and items described herein is implemented or made accessible in online open source platforms or environment. In some embodiments, the systems, methods, and items disclosed herein are compatible with the IMS Question & Test Interoperability (QTI®) specification, thus enabling the exchange of items, test contents, and/or results data between the systems and methods herein with authoring tools, item banks, test construction tools, learning platforms, assessment delivery systems, and scoring/analytics engines.

In some embodiments, items herein include one or more of questions based on one or more QTI interaction types. In some embodiments, the items herein includes a set of interactions (possibly empty) collected together with any supporting material and an optional set of rules for converting the user's response(s) into assessment outcomes. In some embodiments, the set of interactions includes one or more QTI interactions. Nonlimiting examples of QTI interactions include: ChoiceInteraction, OrderInteraction, ExtendedTextInteraction, TextEntryInteraction, GraphicGapMatchInteraction, GapMatchInteraction, HottextInteraction, InlineChoiceInteraction, MatchInteraction, OrderInteraction, TextEntryInteraction, and HotspotInteraction. As an example, an item herein can be a multiple choice question that includes at least one type of QTI interaction, i.e., ChoiceInteraction. As another example, an item can be an order list which includes at least one other type of QTI interaction, i.e., OrderInteraction. Nonlimiting examples of items include: a multiple choice question, an order list question (e.g., order the events, chronologically earliest to latest, list: Russian Revolution, Discovery of the Americas, and Storming of the Bastille), a long text question (e.g., write about their hobbies in no more than 400 words), a close association question (e.g., choose the correct response for each blank.).

Disclosed herein, in some embodiments are generative assessment items. In some embodiments, generative assessment items are non-dichotomously coded items where each of the responses or combinations of responses, encodings, or categorizations represents a unique state, with possibly unique significance and interpretation. Rather than being limited to two only two states, as is the case with dichotomously coded items, a generative assessment item with same number of multiple choice alternatives, e.g., (a)-(d), can have, in some examples, sixteen coded states, or eight times as much information as a dichotomously coded item. In some embodiments, the individual responses or combination of responses within a generative assessment item are no longer treated as independent (e.g., as simple, separate, true/false-like sub-items). In some embodiments, this indicate that for a given non-dichotomously coded multiple choice item the selection of response "b" might tell an educator or a teach something different when paired with "c" than it does when paired with "d". In some embodiments, an item coded in a way that renders the multiple possible states, or treats the individual responses or combinations of responses as not independent, is a generative assessment item.

Encoding

In some embodiments, a set of rules may be utilized to generate encoded responses from one or more responses. In some embodiments, the encoded response comprises a pattern which can uniquely represent the response. In some embodiments, each of the plurality of responses is uniquely associated with a pre-determined pattern. In some embodiments, the encoded response may include one or more number, letter, symbol, or a combination thereof. In some embodiments, one or more patterns represent baseline understanding of the question; one or more other patterns represent accurate understanding of the question; and one or more patterns represent intermediate understanding of the question in between the baseline and the accurate understanding.

In some embodiments, when a response from a user is received, the response and many other responses from other user may be analyzed together. In some embodiments, an encoded response may include an additional encoding based on information of the user. In some embodiments, the information of the user comprises demographical information.

A non-limiting exemplary way of encoding and representing the multiple states or responses of a generative assessment item can include, but not be limited to, representing each of the responses selected with 1 and each of the responses not selected with a 0. For example, for a multiple choice question with 4 different choices, the selection of letters (a), (c) and (d), but not (b), can be represented by 1, 0, 1, 1. This sequence of 1's and 0's can be concatenated to create a binary number 1011. In this way, each of the 16 possible responses or states (of a typical multiple choice) can be represented by a unique four digit binary number. For example:

TABLE 1

| Response | Binary |
|---|---|
| — | 0000 |
| A | 1000 |
| B | 0100 |
| C | 0010 |
| D | 0001 |
| AB | 1100 |
| AC | 1010 |
| AD | 1001 |
| BC | 0110 |
| BD | 0101 |
| CD | 0011 |
| ABC | 1110 |
| ABD | 1101 |
| ACD | 1011 |
| BCD | 0111 |
| ABCD | 1111 |

In some embodiments, a set of rules, such as binary representations can be converted to other base systems, including base sixteen (hexadecimal) or base ten (decimal) representations (e.g., 1011 [binary], B [hexadecimal], or 11 [decimal]). As another example, for an order list question, four elements to order can have 24 response states. The 24 responses may be represented using a sequence of 1's and 0's to create a binary number that can analyzed for patterns. Alternatively, the 24 responses may be represented using histograms. In some embodiments, the first binary number is 1 and the second binary number is 0. In some embodiments, the first binary number is 0 and the second binary number is 1. In some embodiments, each of the two or more answer choices is not independent from each other.

In some embodiments, patterns of response can be analyzed. In some embodiments, analysis of the pattern and a plurality of other patterns comprise generating a histogram of the pattern and the plurality of patterns. Such histogram can indicate a frequency of occurrence of one or more patterns corresponding to responses.

Figure 1:
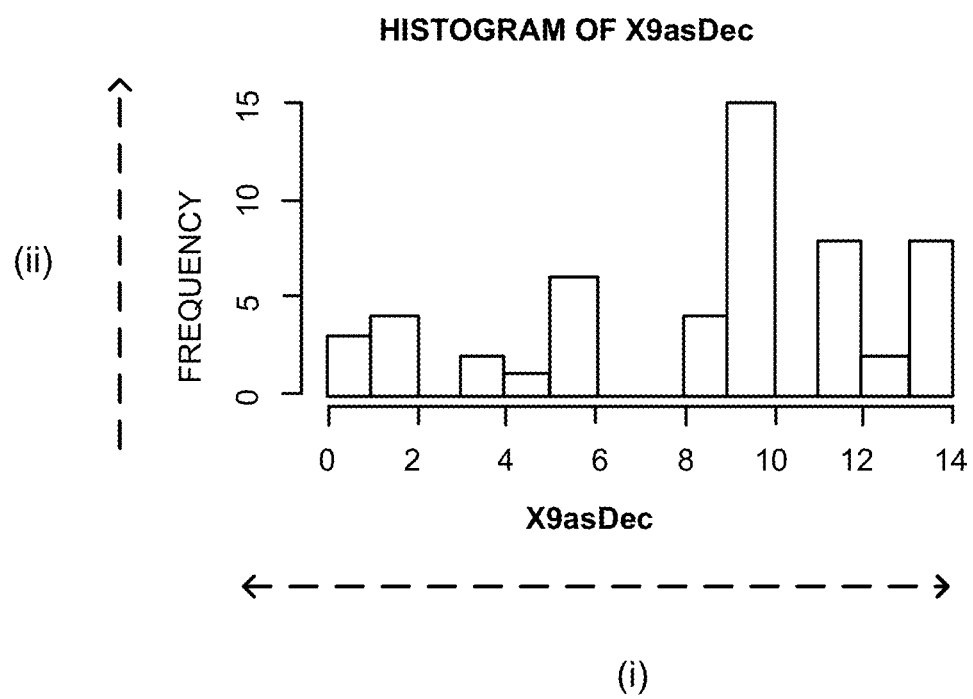
FIG. 1 shows a non-limiting exemplary histogram of frequency of responses for patterns for a given generative assessment item.
Figure 2:
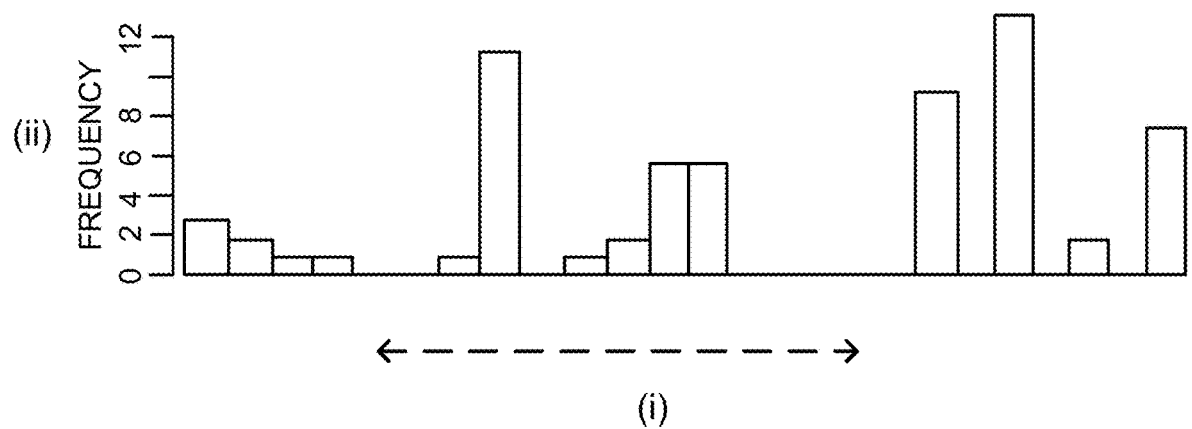
FIG. 2 shows a non-limiting exemplary histogram of frequency of responses for patterns across multiple generative assessment items.

As illustrated in FIG. 1, for a multiple choice, a histogram can be used to display the relative frequencies along axis (ii) of the respective patterns, which is on axis (i). FIG. 2 shows a different histogram that can be used visualize relative frequency (axis (ii)) of the patterns (axis (i)) across multiple generative assessment items. In these two particular embodiments, of particular importance in terms of their value for educational purposes are the patterns, or responses, that occur most frequently (or the most significant modes) both within a given item (FIG. 1) or across items (FIG. 2). In some embodiments, encoding responses into unique patterns may facilitate identification of patterns, thus response, capable of informing education related activities including instructional responses. In some embodiments, analysis tools such as histograms can facilitate identification of patterns that are informative for educational purposes.

In some embodiments, the encoded responses or patterns are compatible with the current state of art. In some embodiments, systems and methods herein allow the encoded responses or patterns to be analyzed as traditional dichotomous items to provide additional information.

Concatenation

FIG. 48 shows a non-limiting table displaying two examples of current scoring concatenation. In the first example as shown, a student answer is provided to a first non-dichotomous generative assessment item, and not a second non-dichotomous generative assessment item. In the second example as shown, a student answer is provided to a second non-dichotomous generative assessment item, and not a first non-dichotomous generative assessment item. As shown the first concatenated response is stored as "A, B" and the second concatenated response is also stored as "A, B." As such, current scoring concatenation methods are ambiguous, whereas data regarding which student answers were provided to which non-dichotomous generative assessment item is not recorded and/or lost. While current scoring concatenation methods can further include additional delimiters, or other identification characters, such means only increase the amount of memory required to store the student answers.

Further examples of the ambiguity inherent to exemplary current scoring concatenations are shown in FIGS. 49A-C. Per FIG. 49A a student answer of (ABC) to a first non-dichotomous generative assessment item and a student answer of (D) are concatenated as "ABCD." The concatenation therein is ambiguous as "ABCD" can represent student answers to 1, 2, 3 4, or more non-dichotomous generative assessment items. For example, "ABCD" represent a single student answer of "ABCD" to a single item. Alternatively, "ABCD" can represent student answers (ABC)-(D), (AB)-(CD), or (A)-(BCD) to two items. Further "ABCD" can represent student answers (A)-(BC)-(D), (A)-(B)-(CD), or (AB)-(C)-(D) to three items. In addition, "ABCD" can represent student answer (A)-(B)-(C)-(D) to four items. Such ambiguity reduces the ability of the student answers to be used towards machine learning and machine learning training. Although some current scoring concatenations per FIGS. 49B-C employ delimiters between each student answer, the added delimiters increase the amount of bits required to store the student answers, and are further ambiguous regarding how many items are represented by the student answers. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. Moreover, delimiter placement may lend itself to computer processing error.

By contrast, the exemplary student answer scoring concatenation as provided herein, per FIG. 50, represents student answers to a first non-dichotomous generative assessment item having four answer choices as a first four digit binary number and represents student answers to a second non-dichotomous generative assessment item having four answer choices as a second four digit binary number. As such, concatenating the student answers to the first and second non-dichotomous generative assessment items yields a concatenated answer that is 8 binary digits long and which is not ambiguous. In some embodiments, a size of the concatenated answer is equal to AC bits, wherein AC equals the number of answer choices. In some embodiments, the concatenated answer is not ambiguous.

In some embodiments, the prompt module further displays two or more non-dichotomous generative assessment items, wherein the recording module further receives the student answer to each answer choice for each of the two or more non-dichotomous generative assessment items. In some embodiments, the storage module further stores the received student answer to each answer choice in the series for each of the two or more non-dichotomous generative assessment items, in the binary format, wherein the concatenation module, further concatenating every concatenated answer for each of the two or more non-dichotomous generative assessment items to form a multiple item concatenated answer. As such, per FIG. 51A the exemplary student answer scoring concatenation concatenates student answers to each of five non-dichotomous generative assessment items to form a multiple item concatenated answer. In some embodiments, the two or more non-dichotomous generative assessment items comprise 3, 4, 5, 6, 7, 8, 9, 10, 20, 30, 40, 50, 60 or more non-dichotomous generative assessment items. In some embodiments, a size of the multiple item concatenated answer is equal to AC*Q bits, and wherein AC equals a number of answer choices, and wherein Q equals a number of non-dichotomous generative assessment items. In some embodiments, the multiple item concatenated answer is not ambiguous. In some embodiments, the plurality of non-dichotomous generative assessment items is disposed sequentially in a student test. In some embodiments, the plurality of non-dichotomous generative assessment items is disposed randomly throughout a student test in a non-sequential manner. The plurality of non-dichotomous generative assessment items is disposed sequentially in a student test. In some embodiments, the plurality of non-dichotomous generative assessment items is disposed across multiple exams (e.g., first non-dichotomous generative assessment item provided as Question No. 1 for Student 1 on Jan. 1, 2019 and the second non-generative assessment item provided as Question No. 1 for Student 1 on Jul. 1, 2019).

In some embodiments, the prompt module further displays the non-dichotomous generative assessment item to two or more students; the recording module further receives the student answer to each answer choice in the series for each of the two or more students; the storage module, further stores the received student answer to each answer choice for each of the two or more students, in a binary format; and the concatenation module, further concatenating every concatenated answer for each of the two or more students to form a multiple student concatenated answer. Per FIG. 51B the exemplary student answer scoring concatenation concatenates student answers to a single non-dichotomous generative assessment item from multiple students to form a multiple student concatenated answer. In some embodiments, the two or more students comprise 3, 4, 5, 6, 7, 8, 9, 10, 20, 30, 40, 50, 60 or more students. In some embodiments, a size of the multiple student concatenated answer is equal to AC*S bits, and wherein AC equals a number of answer choices, and wherein S equals a number of students. In some embodiments, the multiple student concatenated answer is not ambiguous. In some embodiments, student answers to non-dichotomous generative assessment items are received at different times wherein, for example, a first student answer is received on a first day to non-dichotomous generative assessment item proctored on the first day, and wherein a second student answer is received on a second day to non-dichotomous generative assessment item proctored on the second day.

Finally, per FIG. 52 the exemplary student answer scoring concatenation concatenates student answers to three non-dichotomous generative assessment item from three students to form a multiple student multiple item concatenated answer.

Generative Assessment Item Development

Disclosed herein includes systems and methods for generative assessment item development comprising one or more of: obtaining a released assessment item which comprises correct answer(s); generating a question for the generative assessment item using information from the correct answer(s) of the released assessment item; and generating a plurality of responses to the question for the generative assessment item, wherein the plurality of responses comprises at least two responses that are not independent, and wherein the plurality of responses are non-dichotomous. In some embodiments, the released assessment item is a non-dichotomous or dichotomous item.

In some embodiments, for generation of an assessment item for a grade level, the indicated grade-level Texas Essential Knowledge and Skills (TEKS) may be considered.

In some embodiments, the connections to the core mathematical ideas and standards for the released item are identified. In some embodiments, such identification is performed automatically by a computer. In some embodiments, computer software, algorithm, or the like is used for such identification. In further embodiments, a machine learning algorithm, artificial intelligence algorithm, a regression model, a classifier, a deep learning algorithm or a combination is used.

In some embodiments, a generative assessment item is generated based on release items, the released items being dichotomous items, generative assessment items, or a combination thereof. In some embodiments, a generative assessment item is generated automatically by a computer. In some embodiments, computer software, algorithm, or the like is used for such generation of generative assessment items. In further embodiments, a machine learning algorithm, artificial intelligence algorithm, a regression model, a classifier, a deep learning algorithm or a combination is used.

In some embodiments, the concatenated answer is converted to a vector format. In some embodiments, the concatenated answer is converted to a vector format by the following algorithm:

Code and Vector Results:
    foo1←function(str 1){as.integer(unlist(strsplit(str 1, " ")))}
    res←foo1("1110001")
    res #[1] 1 1 1 0 0 0 1

In some embodiments, the concatenated answer in the vector format is used directly or indirectly to train a machine learning algorithm. In some embodiments, the concatenated answer in the vector format is used directly or indirectly to perform a machine learning algorithm. In some embodiments, the machine learning algorithm detects a certain class of students according to their answer selections.

In some embodiments, the application further comprises a blockchain module, storing the concatenated answer in an immutable data storage. In some embodiments, the application further comprises a histogram module forming a histogram from the concatenated answer. Exemplary histograms are shown in FIGS. 1 and 2. In some embodiments, the histogram comprises a histogram of the possible combinations of answer choices.

In some embodiments, the development of the item including asking the question "backward" which can include "making the answer to a right/wrong task the question." For example, instead of asking, "What is 2+2?" We can make the answer, '4', into 'the question' by asking students to create expressions that sum to 4. Instances of what students might do or create then become candidates for responses to the item. In this example, 1+3, 0+4 can become candidates in addition to 2+2.

In some embodiments, the possible answers, optionally generated by a computer, or real responses from students can be used to form responses to the item. In some embodiments, the complete set of response includes at least one or more real responses which are the ones that may convey important information about student understanding of the topic. In some embodiments, the possible answers or real answers can include both correct and incorrect responses. In some embodiments, 4, 5, 6, 7, or even more alternatives for a given item are chosen. In the case of 4 alternatives, 16 different and possibly unique responses can be formed.

In some embodiments, an items is designed to have some alternatives that nearly all students are expected to get correct. In some embodiments, these alternatives identify a 'baseline' understanding. In some embodiments, there are alternatives up from this baseline that is expected to be of greater difficulty. The combination of alternatives that is an 'exact match' with the intended combination is often significantly more difficult than the intended baseline responses. In some embodiments, depth of understanding within and across items can be assessed. In some embodiments, with the generative assessment item developed or analyzed using the systems and methods herein, patterns of simply guessing or fragmented understanding can be identified and can serve to identify students for additional support or intervention.

In some embodiments, the items are generated using the specific norms, word choices, fonts and other features of item layout used on released items from which the items are based upon.

Analysis

In some embodiments, the increased information provided by non-dichotomous generative assessment items (multiple choice-multiple answer) disclosed herein advantageously opens up a wide range of possible ways of reporting and scoring results with related tradeoffs in transparency and technical demand.

In some embodiments, one of the analysis or evaluation method disclosed herein include scoring percent correct. For individual items, combinations of items or for tests using at least some non-dichotomous items as a whole, a simple reporting of percent correct relative to the intended responses can be transparent and accessible to users. In some embodiments, such percent correct score can be indicative of how the child/students/school/district does relative to relevant reported averages. In some embodiment, such percent correct is meaningful and useful to nearly all stakeholders in the education system.

In some embodiments, one of the analysis or evaluation method disclosed herein include scaling and equating. Percent correct on anchor items can be used to scale scores. In some embodiments, dichotomous item response theory (IRT)-based methods (of various levels of sophistication) remain available. The IRT based methods may be done in ways consistent with existing industry standards for multiple-select multiple choice items or can be based on innovations related to polytomous analyses.

In some embodiments, one of the analysis or evaluation method disclosed herein include pattern identification. In some embodiments, meaningful patterns in student responses are identified using the methods and systems herein. In some embodiments, the patterns in responses are of great use to professional educators (starting with teachers); helpful in research on learning and teaching, and capable of informing decisions about materials selection and 'best practices' for educating students.

Disclosed herein, in some embodiments, the development of generative assessment items is closely associated with tasks that have been, or could be, used in classrooms. In some embodiments, items are best developed based on experiences from educators who have a sophisticated understanding of the learning and teaching issues and opportunities relative to specific standards and of students at a given grade level.

To the extent that generative assessment items are successful in identifying meaningful patterns in student responses, in some embodiments, they provide a natural connection to professional development in interpreting and acting on assessment results.

Machine Learning

In some embodiments, machine Learning is an automated inductive process resulting in a model that characterize the inherent structure of a dataset based on features of data instances, whereas resultant models are descriptive of the training data, predictive for test data, and have plausible explanatory power. In some embodiments, the model or classifier acquires the classification rules based upon a given set of instances. In some embodiments, the instance is an example in the training data. In some embodiments, the instance is described by a number of attributes (e.g. features in Machine Learning). In some embodiments, the attribute is a well-specified aspect of an instance and can include measured or categorical data. In some embodiments, the attribute is also used a class label. In some embodiments, the class label is an attribute used to define the class of an instance and is required for supervised machine learning. In some embodiments, the class label is associated with the characteristic of the student.

In some embodiments, the sets of concatenated answers each additionally comprise a class label attribute associated with an attribute of its student. In some embodiments, the sets of concatenated answers each additionally comprise two or more class label attributes associated with an attribute of its student. In some embodiments, per FIG. 53, the class label attribute comprises a leading digit 5301 in the set of concatenated answers for each student. As shown therein, the class label attribute is represented binarily, whereas a 0 represents a negative instance of the characteristic and a 1 represents a positive instance of the characteristic. Alternatively, in some embodiments, a 1 represents a negative instance of the characteristic and a 0 represents a positive instance of the characteristic. In some embodiments, the class label attribute is used to train one or more of the machine learning algorithms herein.

In some embodiments, the class label attribute is represented by more than one binary digit. In some embodiments, the more than one binary digit represents at least two severities, or classifications of the instance of the characteristic. In one such example, class label attributes of 00, 01, 10, and 11 represent zero, mild, moderate, and severe autistic characteristics, respectively. In some embodiments, each of the two or more binary digits represents an instance of a separate characteristic. In one such example, class label attributes of 00, 01, 10, and 11 represent the lack of a first and second characteristic, a positive instance of only the second characteristic, a positive instance of only the first characteristic, and positive instances of both the first and second characteristics, respectively.

In some embodiments, the class label attribute is represented non-binarily. In some embodiments, the more than one non-binary digits represent a severity or classification of the characteristic. In one such example, class label attributes of 1, 2, 3, and 4 represent zero, mild, moderate, and severe autistic characteristics, respectively. In some embodiments, the more than one non-binary digits represents a positive or negative instance of more than one characteristic. In one such example, class label attributes of 1, 2, 3, and 4 represent the lack of a first and second characteristic, a positive instance of only the second characteristic, a positive instance of only the first characteristic, and positive instances of both the first and second characteristics, respectively.

In some embodiments, the class label attribute is further or alternatively associated with a biographical indicator. In some embodiments, the biographical indicator is associated with a weight, height, sex, age, ethnicity, social class, immigrant status, or any combination thereof. In one example, the class label attribute is a 0 if the student is female and 1 if the student is male.

In some embodiments, the class label attribute is used to train one or more of the supervised machine learning algorithms herein. In some embodiments, such training algorithms develop classification rules based on commonalities and/or differences found between students having a positive class label attribute, students having a negative class label attribute, and/or students having unclassified class label attributes. In some embodiments, the machine learning algorithms trained thereby assign a class label to an as yet unclassified student based on their answer selections and/or non-selections. In some embodiments, such machine learning algorithms are evaluated in terms of their accuracy in assigning labels to instances.

In some embodiments, a portion of the class labels that are known in advance to train the machine learning algorithms herein to assign a class label to as yet unclassified instances. In some embodiments, the accuracy of a machine learning algorithm is determined by comparing its results to known class labels associated with the input data. However, in some embodiments, data used by the trained machine learning algorithm does not have known associated class labels.

FIG. 54 shows a non-limiting table displaying the detection of patterns in student responses associated with a class label attribute. In this example, each of 11 students (one student per row) are each assigned a single binary class label attribute, wherein a 0 class label attribute is associated with a student lacking dyscalculia, and wherein a 1 class label attribute is associated with a student having dyscalculia. As seen therein each column represents the students answer selection to a single answer choice, whereas the first four columns represent four student answers to a first question, whereas the second group of four columns represent four student answers to a second question, whereas the third group of four columns represent four student answers to a third question. As shown therein, a pattern is detected wherein student answers to answer choices q01r02 (representing question 1 answer choice 2), q01r03, q02r01, q02r02, q02r03, q02r04, and q03r02 represent answer choices having a low correlation with the class label attribute. Further, student answers to answer choices q01r01, and q01r04 represent answer choices having a moderate correlation with the class label attribute, and student answers to answer choices q03r01, q03r03, and q03r04 represent answer choices having a high correlation with the class label attribute. In some embodiments, the distinction between low, moderate, and high correlation can be set by a correlation threshold.

Figure 57:
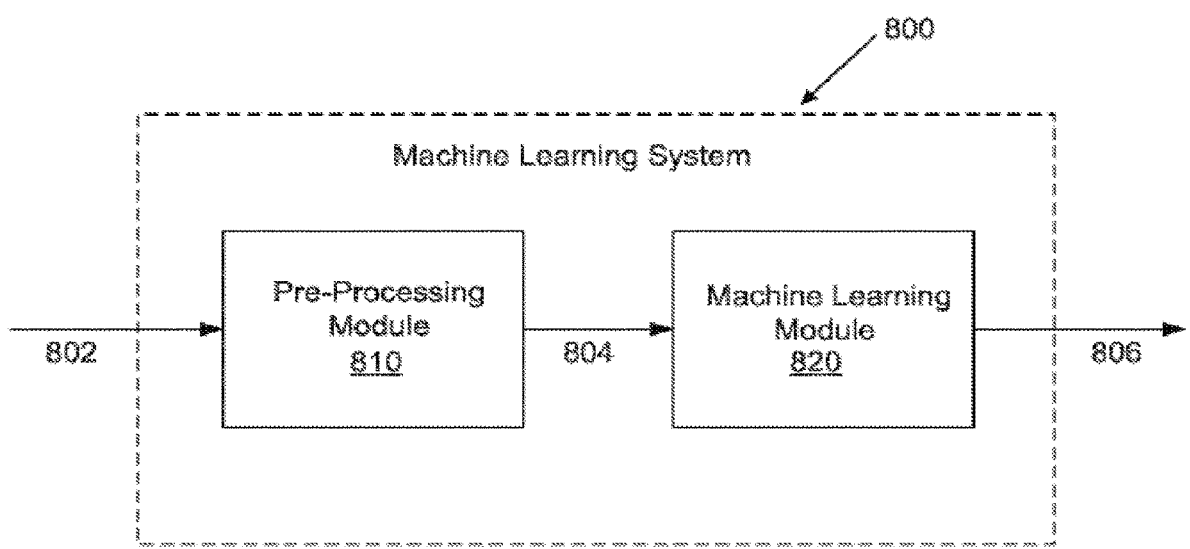
FIG. 57 illustrates a schematic block diagram of a machine learning system comprising a pre-processing module and a machine learning module.

FIG. 57 illustrates a schematic block diagram of a machine learning system comprising a pre-processing module and a machine learning module. The machine learning system 800 may comprise a pre-processing module 810 and a machine learning module (also referred to as an approximator or an approximation module) 820. The components within the machine learning system may be operatively connected to one another via a network or any type of communication link that allows transmission of data from one component to another. The machine learning system may be implemented using software, hardware, or a combination of software and hardware in one or more of the components of the systems and methods described herein.

In some embodiments, the first plurality and the second plurality of the sets of concatenated answers 802 are collected, whereby the pre-processing module 810 subjects the first plurality and the second plurality of sets of concatenated answers 802 to pre-processing. In some embodiments, the machine learning module 820 then process the pre-processed sets of concatenated answers 804 to determine an existence of a characteristic, a probability of the existence of the characteristic, or both for each a plurality of students 806.

Provided herein is a computer-implemented method of identifying a presence of a characteristic, a probability of the presence of the characteristic, or both for each a plurality of students. Also provided herein is a computer-implemented system to identify a presence of a characteristic, a probability of the presence of the characteristic, or both for each a plurality of students. In some embodiments, the system comprises: a computer-readable storage device coupled to at least one processor and having instructions stored thereon. Further provided herein is a non-transitory computer-readable storage media encoded with a computer program including instructions executable by a processor to create an application to identify a presence of a characteristic, a probability of the presence of the characteristic, or both for each a plurality of students.

In some embodiments, the method, processor, application or any combination thereof perform at least the following: receiving two or more answer selections; concatenating the answer selections; and running a machine algorithm on the plurality of sets of concatenated answers to identify the presence of a characteristic, a probability of the presence of the characteristic, or both for each a plurality of students. In some embodiments, the answer selections are in a binary format. In some embodiments, the answer selections are in a binary format for each of a plurality of non-dichotomous generative assessment items. In some embodiments, the answer selections are in a binary format for each of a plurality of non-dichotomous generative assessment items for each of the plurality of students. In some embodiments, concatenating the answer selections comprises concatenating the answer selections for each of the plurality of non-dichotomous generative assessment item. In some embodiments, concatenating the answer selections comprises concatenating the answer selections for each of the plurality of non-dichotomous generative assessment item and for each of the plurality of students to form a set of concatenated answers. In some embodiments, the machine algorithm is trained by the methods, systems, or media provided herein.

In some embodiments, each answer choice is in a binary format, wherein an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof.

In some embodiments, machine learning algorithms are utilized to aid in determining a identify a characteristic of each a plurality of students. In some embodiments, machine learning algorithms are utilized to aid in identifying a presence of a characteristic, a probability of the presence of the characteristic, or both for each a plurality of students. In some embodiments, the presentence of the characteristic is identified when the probability of the presence of the characteristic is beyond a set threshold. In some embodiments, the threshold is about 10%, 20%, 30%, 40%, 50%, 60%, 70%, 80%, 90%, or more including increments therein. In some embodiments, the machine learning algorithms to identify a characteristic of each a plurality of students employs one or more forms of labels including but not limited to human annotated labels and semi-supervised labels. The human annotated labels can be provided by a hand-crafted heuristic. For example, the hand-crafted heuristic can comprise examining differences between two student's answers to the same non-dichotomous generative assessment item. The semi-supervised labels can be determined using a clustering technique to find properties similar to those flagged by previous human annotated labels and previous semi-supervised labels. The semi-supervised labels can employ a XGBoost, a neural network, or both. In some embodiments, the machine learning algorithm comprises an artificial neural network algorithm, a Gaussian process regression algorithm, a logistical model tree algorithm, a random forest algorithm, a fuzzy classifier algorithm, a decision tree algorithm, a hierarchical clustering algorithm, a k-means algorithm, a fuzzy clustering algorithm, a deep Boltzmann machine learning algorithm, a deep convolutional neural network algorithm, a deep recurrent neural network, or any combination thereof.

In some embodiments, machine learning to determine a identify a characteristic of each a plurality of students is trained using a distant supervision method. The distant supervision method can create a large training set seeded by a small hand-annotated training set. The distant supervision method can comprise positive-unlabeled learning with the training set as the 'positive' class. The distant supervision method can employ a logistic regression model, a recurrent neural network, or both. The recurrent neural network can be advantageous for Natural Language Processing (NLP) machine learning.

Examples of machine learning algorithms may include a support vector machine (SVM), a naïve Bayes classification, a random forest, a neural network, deep learning, or other supervised learning algorithm or unsupervised learning algorithm for classification and regression. The machine learning algorithms may be trained using one or more training datasets.

In some embodiments, the machine learning algorithm utilizes regression modeling, wherein relationships between predictor variables and dependent variables are determined and weighted. In one embodiment, for example, the characteristic is a dependent variable and is derived from a pattern of student responses to the same question. In another embodiment, for example, the characteristic is a dependent variable and is derived from a pattern of answer selections to the same question. In another embodiment, for example, the characteristic is a dependent variable and is derived from the plurality of sets of concatenated answers.

In yet another embodiment, the probability that a characteristic is associated with a student is a dependent variable derived from the following predictor variables: the answer selections, the sets of concatenated answers, the concatenated answers, or any combination thereof.

In some embodiments, a machine learning algorithm is used to select catalogue images and recommend project scope. A non-limiting example of a multi-variate linear regression model algorithm is seen below: probability=A0+A1(X1)+A2(X2)+A3(X3)+A4(X4)+A5(X5)+A6(X6)+A7(X7) . . . wherein Ai (A1, A2, A3, A4, A5, A6, A7, . . . ) are "weights" or coefficients found during the regression modeling; and Xi (X1, X2, X3, X4, X5, X6, X7, . . . ) are data collected from the User. Any number of Ai and Xi variable may be included in the model. For example, in a non-limiting example wherein there are 7 Xi terms, X1 is the number of concatenated answers, X2 is the number of students, and X3 is the probability that a student has the characteristic. In some embodiments, the programming language "R" is used to run the model.

Training Machine Learning Algorithms

Another aspect provided herein is a computer-implemented method of training one or more machine learning algorithms to identify an existence of a characteristic, a probability of the existence of the characteristic, or both for each a plurality of students. Also provided herein is a computer-implemented system for training one or more machine learning algorithms to identify a presence of a characteristic, a probability of the presence of the characteristic, or both for each a plurality of students. In some embodiments, the system comprises: a computer-readable storage device coupled to at least one processor and having instructions stored thereon. Further provided herein is a non-transitory computer-readable storage media encoded with a computer program including instructions executable by a processor to create an application to train one or more machine learning algorithms to identify a presence of a characteristic, a probability of the presence of the characteristic, or both for each of a plurality of students.

In some embodiments, the method, processor, application or any combination thereof perform at least the following: collecting a first plurality and a second plurality of sets of concatenated answers; creating a first training set; training the machine learning algorithm in a first stage using the first training set; creating a second training set; and training the machine learning algorithm in a second stage using the second training set.

In some embodiments, the method, processor, application or any combination thereof perform at least the following: receiving two or more answer selections, concatenating the answer selections, creating a first training set, training the machine learning algorithm in a first stage using the first training set; creating a second training set for a second stage of training, and training the machine learning algorithm in a second stage using the second training set.

In some embodiments, each set of concatenated answers is associated with one of the plurality of students. In some embodiments, the set of concatenated answers comprises a series of two or more answer choices to each of a plurality of non-dichotomous generative assessment items. In some embodiments, the two or more answer selections comprises answer selections in a binary format. In some embodiments, the two or more answer selections comprises answer selections in a binary format for each of a plurality of non-dichotomous generative assessment items. In some embodiments, the two or more answer selections comprises answer selections in a binary format for each of a plurality of non-dichotomous generative assessment items for each of the plurality of students. In some embodiments, concatenating the answer selections comprises concatenating the answer selections for each of the plurality of non-dichotomous generative assessment item and for each of the plurality of students to form a set of concatenated answers.

In some embodiments, each of the first plurality of sets of concatenated answers is associated with one of the plurality of students having the characteristic. In some embodiments, each of the second plurality of sets of concatenated answers is associated with one of the plurality of students lacking the characteristic. In some embodiments, the existence of the characteristic comprises an existence of one or more characteristics. In some embodiments, the probability of the existence of the characteristic comprises the probability of the existence of one or more characteristics. In some embodiments, determining the existence of one or more characteristics comprises determining the existence of one or more characteristics in serial or in parallel. In some embodiments, determining the probability of the existence of one or more characteristics comprises determining the probability of the existence of one or more characteristics in serial or in parallel.

In some embodiments, the first training set comprises the collected set of concatenated answers, a first portion of the collected set of concatenated answers associated with students having the characteristic, and a second portion of the collected set of concatenated answers associated with students lacking the characteristic. In some embodiments, the second training set comprises the first training set and the sets of concatenated answers associated with students lacking the characteristic that are incorrectly detected as having the characteristic after the first stage of training. In some embodiments, the second training set comprises the first training set and the sets of concatenated answers associated with students having the characteristic that are incorrectly detected as lacking the characteristic after the first stage of training.

In some embodiments, each answer choice is in a binary format, wherein an answer selection is stored as a first binary number and an answer non-selection is stored as a second binary number. In some embodiments, the first binary number is 1 and the second binary number is 0. In some embodiments, the first binary number is 0 and the second binary number is 1. In some embodiments, the concatenated answers are concatenated without a delimiter. In some embodiments, the delimiter comprises a comma, a semicolon, a colon, a tab, a bracket, a parenthesis, a hashtag, a quotation mark, an asterisk, or any combination thereof. In some embodiments, the delimiter is not located between the two or more answer choices. In some embodiments, the two or more answer choices comprise 3, 4, 5, 6, 7, 8, 9, 10 or more answer choices. In some embodiments, a size of the concatenated answer is equal to AC bits, wherein AC equals the number of answer choices. In some embodiments, a size of the multiple item concatenated answer is equal to AC*Q bits, and wherein AC equals a number of answer choices, and wherein Q equals a number of non-dichotomous generative assessment items. In some embodiments, the concatenated answer is not ambiguous. In some embodiments, each of the two or more answer choices are not independent from each other.

In some embodiments, the characteristic comprises a non-native language, a medical condition, or both. In some embodiments, the medical condition is a mental disorder, genetic disorder, emotional disorder, behavioral disorder, or any combination thereof. In some embodiments, the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof.

In one example the student is diagnosed with dyscalculia, which is an impaired ability to calculate or perform mathematical functions. In another example, the student is identified as a speaker of a non-native language (e.g.: English Language Learner) who come from non-English-speaking homes and backgrounds, are unable to communicate fluently or learn effectively in English, and who typically require specialized or modified instruction in both the English language and in their academic courses.

In some embodiments, training comprises multiple steps. In a first step, an initial model is constructed by assigning probability weights to predictor variables. In a second step, the initial model is used to "recommend" student characteristics. In a third step, the validation module accepts verified data regarding the student characteristics and feeds back the verified data. At least one of the first step, the second step, and the third step can repeat one or more times continuously or at set intervals.

As described herein, in some embodiments the machine learning algorithm(s) employed to identify an existence of a characteristic, a probability of the existence of the characteristic, or both for each a plurality of students comprise a supervised learning algorithm, an unsupervised learning algorithm, a semi-supervised learning algorithm, a reinforcement learning algorithm, a deep learning algorithm, or any combination thereof.

Supervised learning algorithms: In some embodiments, supervised learning algorithms are algorithms that rely on the use of a set of labeled training data to infer the relationship between a set of one or more concatenated answers submitted by a given student and a characteristic of the student according to a specified set of quality criteria. The training data comprises a set of paired training examples, e.g., where each example comprises a set of concatenated answers received for a given student and the characteristics of the given student, or where each example comprises a set of concatenated answers that is associated with a known characteristic.

Unsupervised learning algorithms: In some embodiments, unsupervised learning algorithms are algorithms used to draw inferences from training datasets consisting of student characteristic datasets that are not paired with concatenated answers. The most commonly used unsupervised learning algorithm is cluster analysis, which is often used for exploratory data analysis to find hidden patterns or groupings in process data.

Semi-supervised learning algorithms: In some embodiments, semi-supervised learning algorithms are algorithms that make use of both labeled and unlabeled characteristic for training (typically using a relatively small amount of labeled data with a large amount of unlabeled data).

Deep learning algorithms: In some embodiments, deep learning algorithms are algorithms inspired by the structure and function of the human brain called artificial neural networks (ANNs), and specifically large neural networks comprising many layers, that are used to map student answer selections to characteristic. Artificial neural networks will be discussed in more detail below.

Decision tree-based expert systems: In some embodiments, expert systems are one example of supervised learning algorithms that are designed to determine a student's characteristic by applying a series of if—then rules. Expert systems typically comprise two subsystems: an inference engine and a knowledge base. The knowledge base comprises a set of facts (e.g., a training data set comprising student characteristics for a series of student answer selections) and derived rules (e.g., derived characteristic rules). The inference engine then applies the rules to data for a current student to determine a student's characteristics.

Support vector machines (SVMs): In some embodiments, support vector machines are supervised learning algorithms used for classification and regression analysis of student characteristics. Given a set of training data examples (e.g., student answer choices), each marked as belonging to one or the other of two characteristic determinations (e.g., has or lacks the characteristic), an SVM training algorithm builds a model that assigns new examples (e.g., student answer choices) to one characteristic or the other.

Autoencoders: In some embodiments, an autoencoder (also sometimes referred to as an autoassociator or Diabolo network) is an artificial neural network used for unsupervised, efficient mapping of input data, e.g., student answer choices, to an output value, e.g., the characteristic. Autoencoders are often used for the purpose of dimensionality reduction, i.e., the process of reducing the number of random variables under consideration by deducing a set of principal component variables. Dimensionality reduction may be performed, for example, for the purpose of feature selection (i.e., a subset of the original variables) or feature extraction (i.e., transformation of data in a high-dimensional space to a space of fewer dimensions).

Artificial neural networks (ANNs): In some cases, the machine learning algorithm used may comprise an artificial neural network (ANN), e.g., a deep machine learning algorithm. The automated object classification methods of the present disclosure may, for example, employ an artificial neural network to map student answer choices to student characteristics. In some embodiments, the methods, media, and systems of the present disclosure employ an artificial neural network (ANN) to determine an optimal set or sequence of parameter settings for adaptive control of characteristic detection. The artificial neural network may comprise any type of neural network model, such as a feedforward neural network, radial basis function network, recurrent neural network, or convolutional neural network, and the like. In some embodiments, the methods and systems of the present disclosure may employ a pre-trained ANN architecture.

Figure 55:
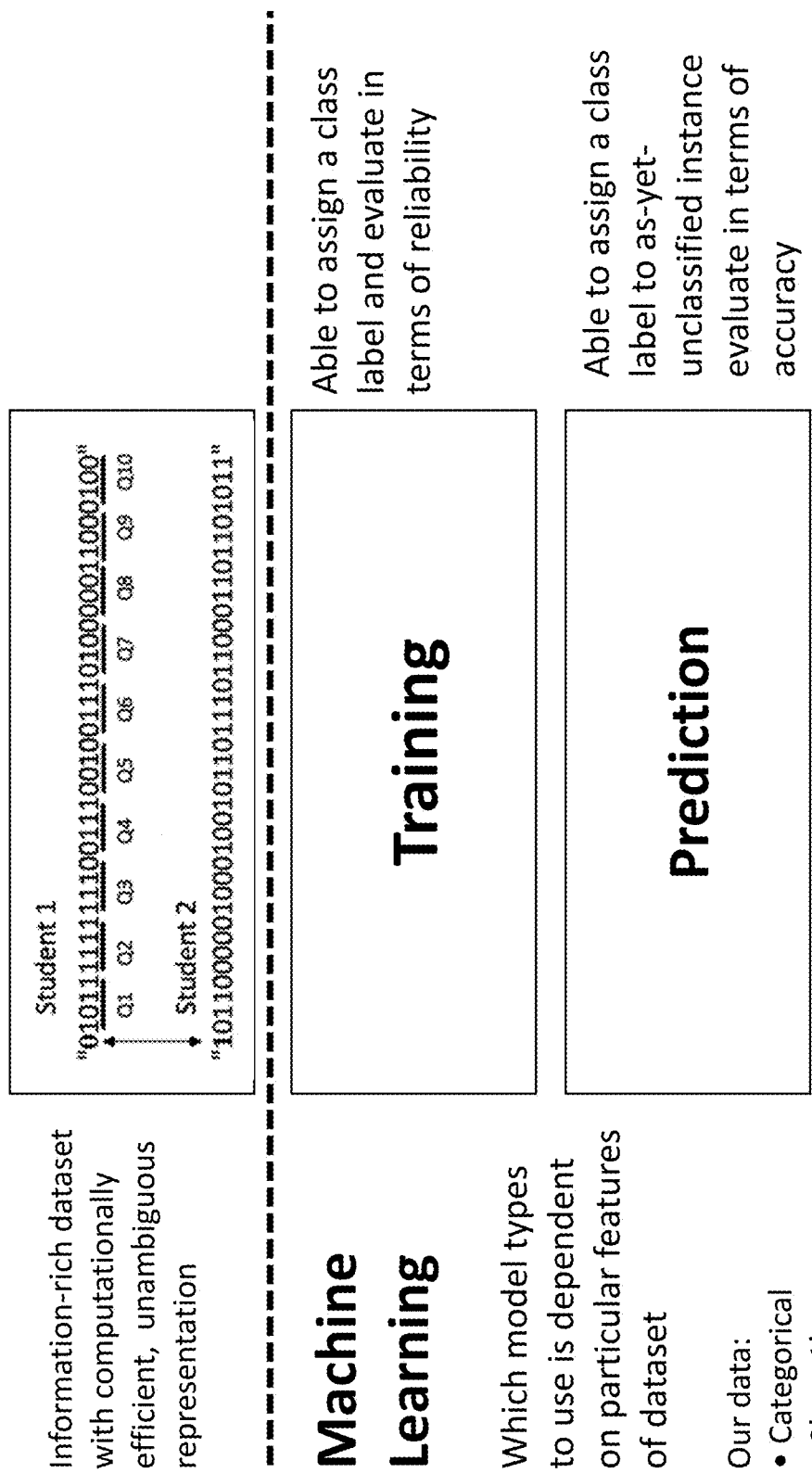
FIG. 55 shows a non-limiting diagram of a method of training and performing a machine learning algorithm to identify an existence of a characteristic, a probability of the existence of the characteristic, or both for each a plurality of students.
Figure 61:
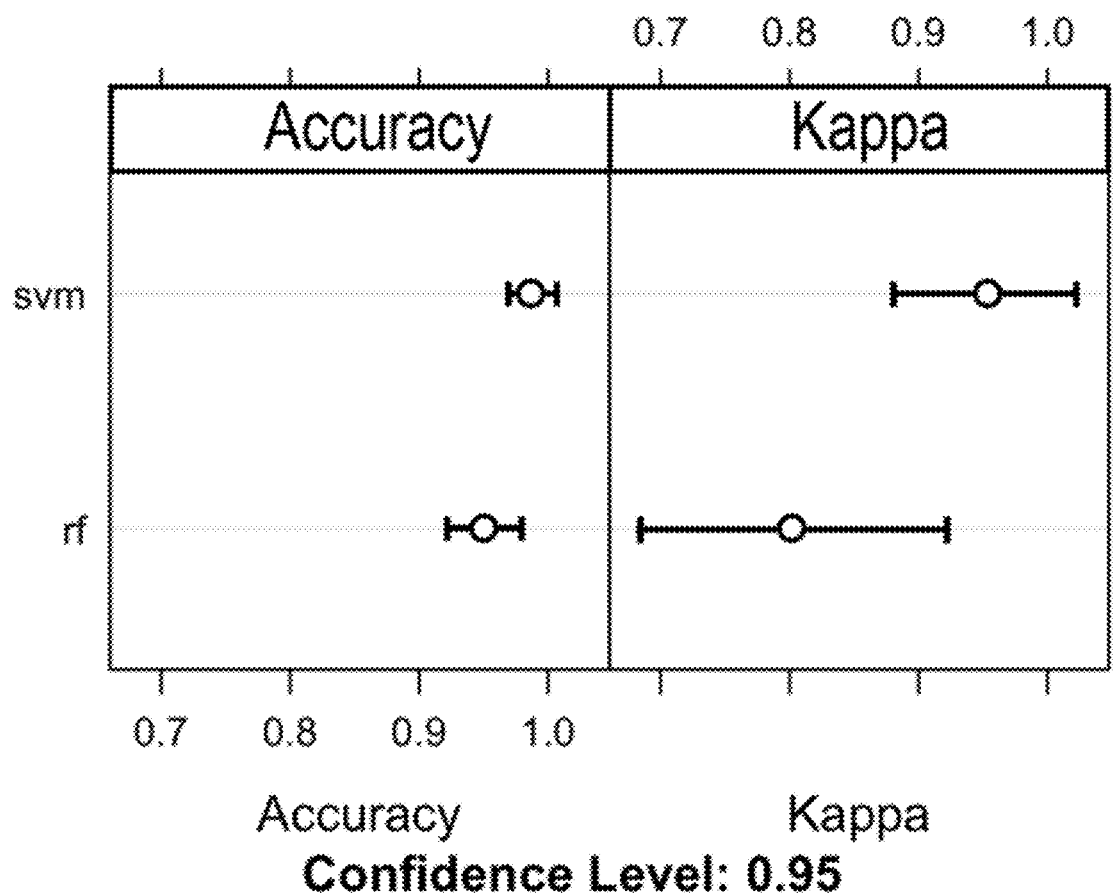
FIG. 61 shows accuracy and Kappa results for exemplary Support Vector Machine (SVM) and exemplary random forest (RF) machine learning algorithms.

FIGS. 55 and 56 shows non-limiting diagrams of a method of training and performing a machine learning algorithms to identify an existence of a characteristic, a probability of the existence of the characteristic, or both for each a plurality of students. As shown therein, an information-rich dataset with computationally efficient, unambiguous representation of concatenated student answers is used to train the machine learning algorithm. Further, the training of the machine learning algorithms assign and determine the reliability of the correlation between the student answers and a class label attribute, and/or assign a class label attribute based on the student answers. Per FIG. 56, Support Vector Machine (SVM) and linear kernel Random Forest (RF) machine algorithms were compared for reliability to correlate and/or assign class label attributes. In some embodiments, the reliability is calculated as number of correctly identified class label attributes compared to the number of assessed students. In some embodiments, the reliability is calculated as number of incorrectly identified class label attributes compared to the number of assessed students. In some embodiments, the reliability is calculated as number of correctly identified class label attributes compared to the number of incorrectly identified class label attributes. In some embodiments, the reliability is calculated as a minimum, a maximum, or an average value between various sets of student answers. FIG. 60 shows an exemplary algorithm for machine learning reliability and accuracy testing. FIG. 61 shows accuracy and Kappa results for Support Vector Machine (SVM) and random forest (RF) machine learning algorithms. FIG. 62 shows an exemplary algorithm for performing SVM and RF machine learning algorithms and FIGS. 63 and 64 show the accuracy statistics for the SVM and RF machine learning algorithms.

Figure 58:
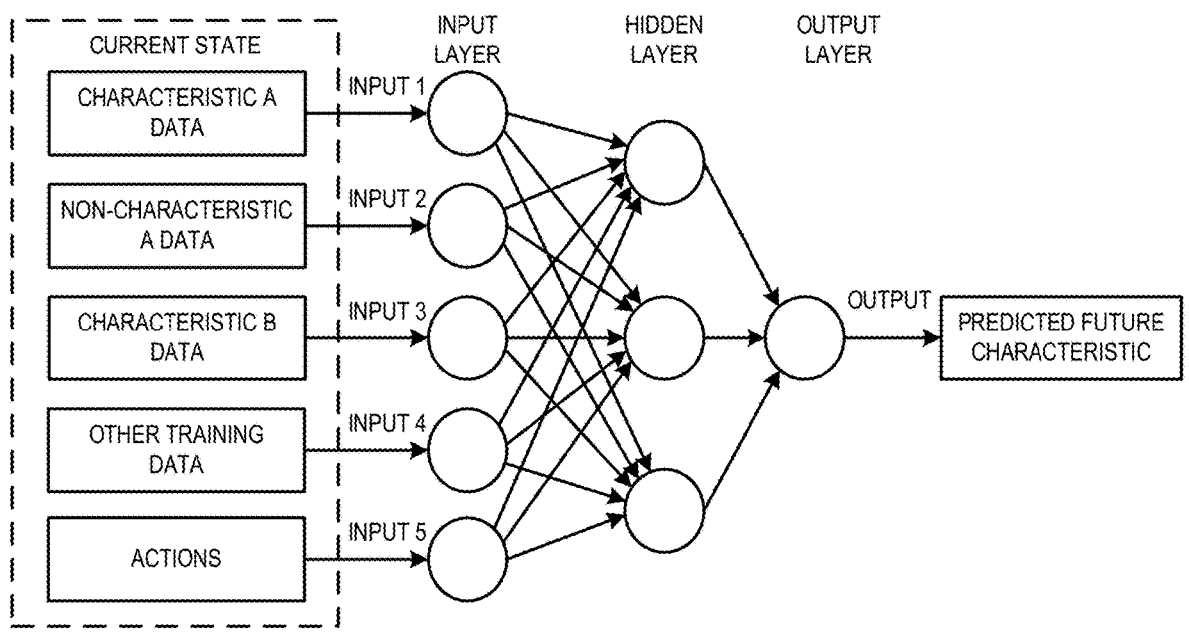
FIG. 58 provides a schematic illustration of an artificial neural network according to some embodiments of the present disclosure, and examples of the input(s) and output(s) of a neural network.

Per FIG. 58, artificial neural networks generally comprise an interconnected group of nodes organized into multiple layers of nodes. For example, the ANN architecture may comprise at least an input layer, one or more hidden layers, and an output layer. The ANN may comprise any total number of layers, and any number of hidden layers, where the hidden layers function as trainable feature extractors that allow mapping of a set of input data to a preferred output value or set of output values. Each layer of the neural network comprises a number of nodes (or neurons). A node receives input that comes either directly from the input data (e.g., student answer selections) or the output of nodes in previous layers, and performs a specific operation, e.g., a summation operation. In some cases, a connection from an input to a node is associated with a weight (or weighting factor).

Figure 11:
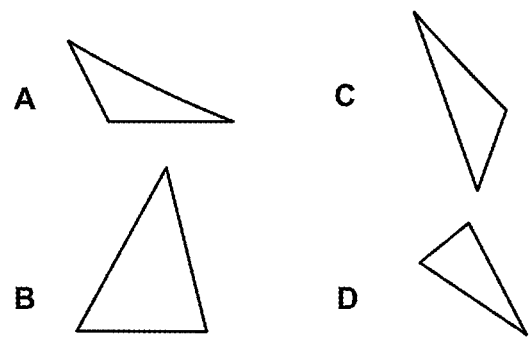
FIG. 11 shows a ninth non-limiting examples of a generative assessment item.
Figure 15:
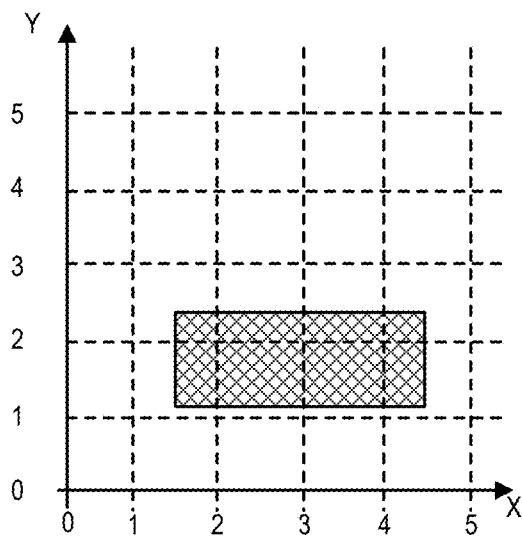
FIG. 15 shows a thirteenth non-limiting examples of a generative assessment item.
Figure 20:
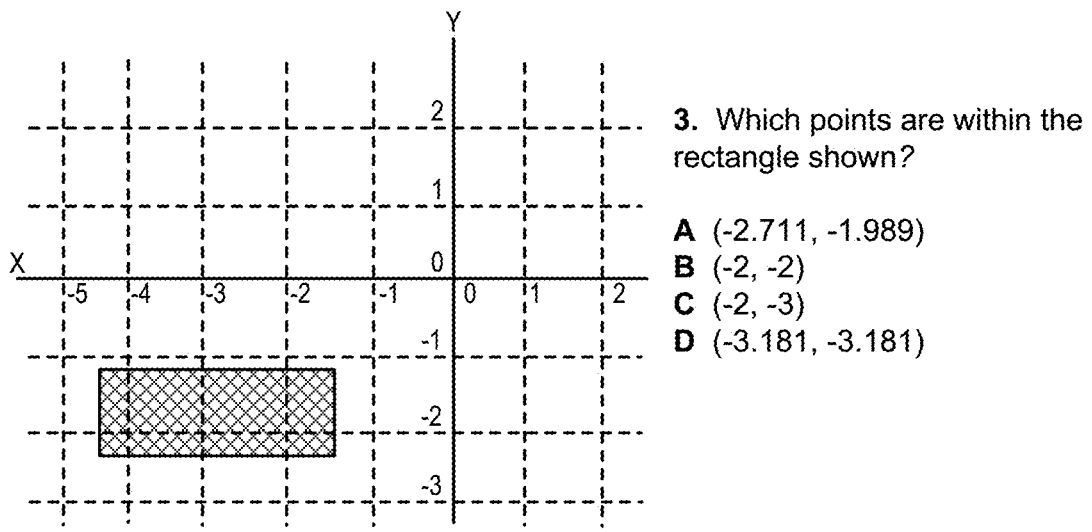
FIG. 20 shows an eighteenth non-limiting examples of a generative assessment item.
Figure 22:
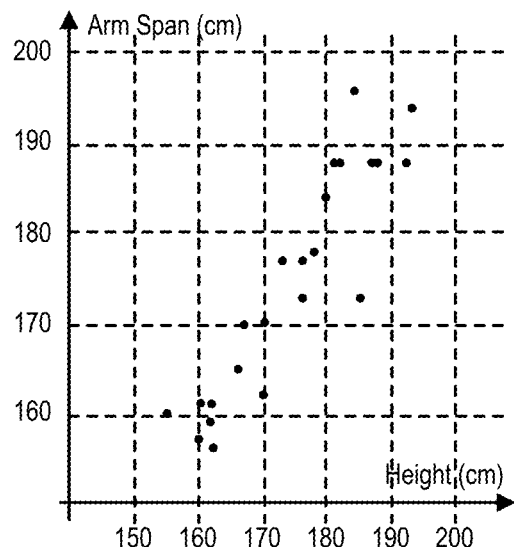
FIG. 22 shows a twentieth non-limiting examples of a generative assessment item.
Figure 25:
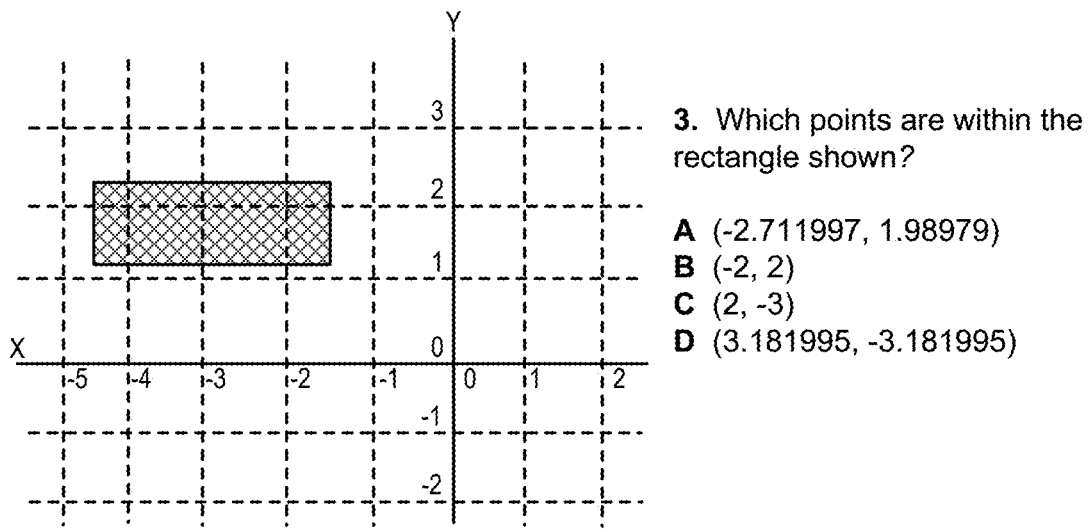
FIG. 25 shows a twenty-third non-limiting examples of a generative assessment item.
Figure 28:
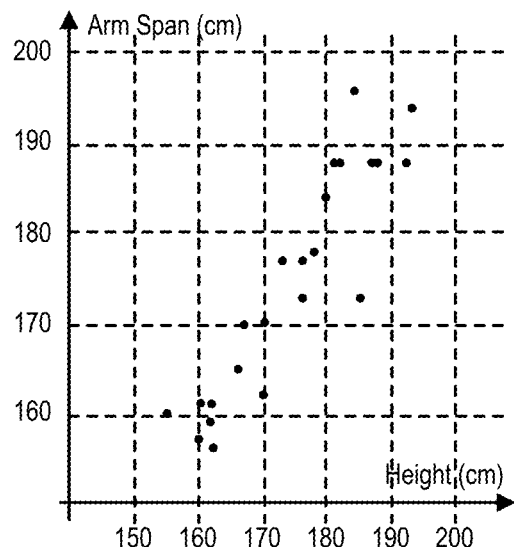
FIG. 28 shows a twenty-sixth non-limiting examples of a generative assessment item.
Figure 32:
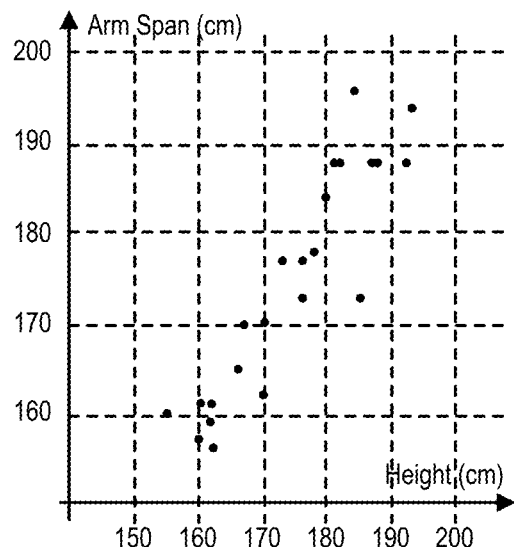
FIG. 32 shows a thirtieth non-limiting examples of a generative assessment item.
Figure 34:
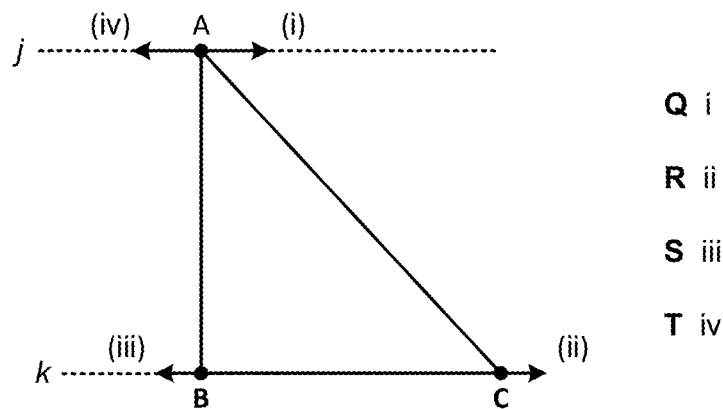
FIG. 34 shows a thirty-second non-limiting examples of a generative assessment item.
Figure 35:
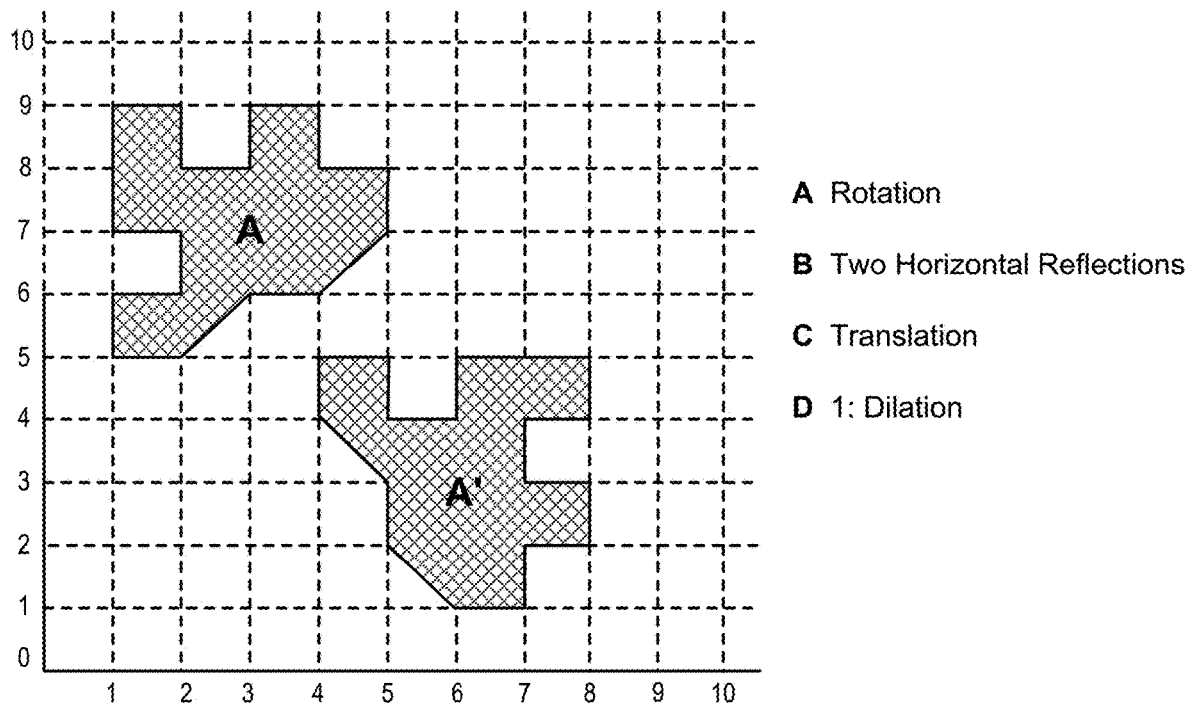
FIG. 35 shows a thirty-third non-limiting examples of a generative assessment item.
Figure 59:
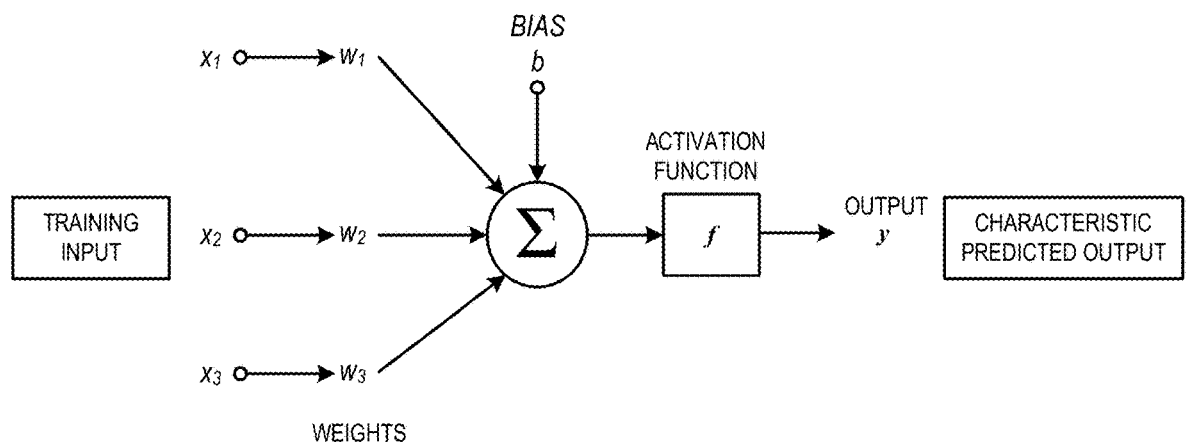
FIG. 59 provides a schematic illustration of the functionality of a node within a layer of an artificial neural network.

In some cases, per FIG. 59, the node sums up the products of all pairs of inputs, xi, and their associated weights, wi. In some cases, the weighted sum is offset with a bias, b, as illustrated in FIG. 11. In some cases, the output of a neuron may be gated using a threshold or activation function, f, which may be a linear or non-linear function. The activation function may be, for example, a rectified linear unit (ReLU) activation function or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

The weighting factors, bias values, and threshold values, or other computational parameters of the neural network, can be "taught" or "learned" in a training phase using one or more sets of training data. For example, the parameters may be trained using the input data from a training data set and a gradient descent or backward propagation method so that the output value(s) that the ANN computes are consistent with the examples included in the training data set.

Other specific types of deep machine learning algorithms, e.g., convolutional neural networks (CNNs) may also be used by the disclosed methods and systems. CNN are commonly composed of layers of different types: convolution, pooling, upscaling, and fully-connected node layers. In some cases, an activation function such as rectified linear unit may be used in some of the layers. In a CNN architecture, there can be one or more layers for each type of operation performed. A CNN architecture may comprise any number of layers in total, and any number of layers for the different types of operations performed. The simplest convolutional neural network architecture starts with an input layer followed by a sequence of convolutional layers and pooling layers, and ends with fully-connected layers. Each convolution layer may comprise a plurality of parameters used for performing the convolution operations. Each convolution layer may also comprise one or more filters, which in turn may comprise one or more weighting factors or other adjustable parameters. In some instances, the parameters may include biases (i.e., parameters that permit the activation function to be shifted). In some cases, the convolutional layers are followed by a layer of ReLU activation function. Other activation functions can also be used, for example the saturating hyperbolic tangent, identity, binary step, logistic, arcTan, softsign, parameteric rectified linear unit, exponential linear unit, softPlus, bent identity, softExponential, Sinusoid, Sinc, Gaussian, the sigmoid function and various others. The convolutional, pooling and ReLU layers may function as learnable features extractors, while the fully connected layers may function as a machine learning classifier.

As with other artificial neural networks, the convolutional layers and fully-connected layers of CNN architectures typically include various computational parameters, e.g., weights, bias values, and threshold values, that are trained in a training phase as described above.

In general, the number of nodes used in the input layer of the ANN (which enable input of data from multiple sensor data streams and/or, for example, sub-sampling of an image frame) may range from about 10 to about 10,000 nodes. In some instances, the number of nodes used in the input layer may be at least 10, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, or at least 10,000. In some instances, the number of node used in the input layer may be at most 10,000, at most 9000, at most 8000, at most 7000, at most 6000, at most 5000, at most 4000, at most 3000, at most 2000, at most 1000, at most 900, at most 800, at most 700, at most 600, at most 500, at most 400, at most 300, at most 200, at most 100, at most 50, or at most 10. Those of skill in the art will recognize that the number of nodes used in the input layer may have any value within this range, for example, about 512 nodes.

In some instance, the total number of layers used in the ANN (including input and output layers) may range from about 3 to about 20. In some instance the total number of layer may be at least 3, at least 4, at least 5, at least 10, at least 15, or at least 20. In some instances, the total number of layers may be at most 20, at most 15, at most 10, at most 5, at most 4, or at most 3. Those of skill in the art will recognize that the total number of layers used in the ANN may have any value within this range, for example, 8 layers.

In some instances, the total number of learnable or trainable parameters, e.g., weighting factors, biases, or threshold values, used in the ANN may range from about 1 to about 10,000. In some instances, the total number of learnable parameters may be at least 1, at least 10, at least 100, at least 500, at least 1,000, at least 2,000, at least 3,000, at least 4,000, at least 5,000, at least 6,000, at least 7,000, at least 8,000, at least 9,000, or at least 10,000. Alternatively, the total number of learnable parameters may be any number less than 100, any number between 100 and 10,000, or a number greater than 10,000. In some instances, the total number of learnable parameters may be at most 10,000, at most 9,000, at most 8,000, at most 7,000, at most 6,000, at most 5,000, at most 4,000, at most 3,000, at most 2,000, at most 1,000, at most 500, at most 100 at most 10, or at most 1. Those of skill in the art will recognize that the total number of learnable parameters used may have any value within this range, for example, about 2,200 parameters.

Group-Based Cloud Computing

Disclosed herein, in certain embodiments, are group-based cloud computing (GBCC) systems. In some embodiments, a generative assessment item is provided to a user in a group-based cloud computing system. In some embodiments, the systems and methods herein includes receiving the response to the generative assessment item from the user in a group-based cloud computing system.

In some embodiments, the group-based cloud computing system comprises: (a) a set of communications elements configured to provide a cloud network infrastructure; (b) an integrated array of representation tools; and (c) a plurality of collaborative activities deploying the set of communications elements and the integrated array of representation tools. In some embodiments, the group-based cloud computing system comprises a number of virtual classrooms, the number of virtual classrooms configured to work simultaneously and independently. In some embodiments, one or more of the virtual classrooms are author-able at a group activity level and at a learner level.

In some embodiments, the group-based cloud computing system herein allows the user to: create a coded object or behavior, post an image with embedded code in a gallery, select an object from the gallery to be added to the user's work space, or a combination thereof.

In some embodiments, the group-based cloud computing system herein allows the user or an activity author to select when and to whom a student space or a group-shared space is available.

In some embodiments, the group-based cloud computing system herein allows the user to turn on or off updates in the student space or the group-shared space, wherein the student space or the group-shared space is virtual space accessible by the user via a user interface.

In some embodiments, the group-based cloud computing system herein allows the user to code using one or more agent-based modeling languages.

Digital Processing Device

In some embodiments, the systems, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeB SD, OpenB SD, NetB SD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 37:
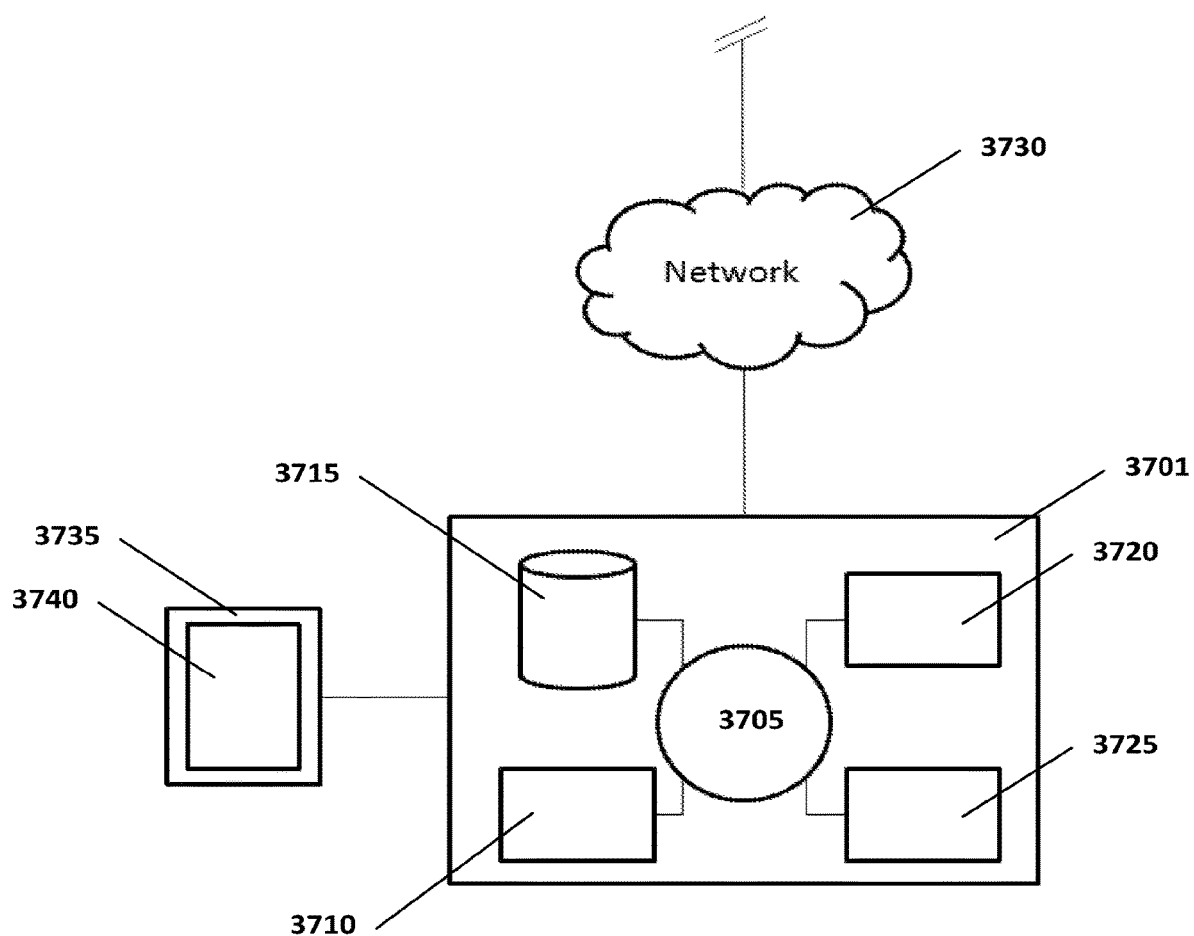
FIG. 37 shows a non-limiting schematic diagram of a digital processing device; in this case, a device with one or more CPUs, a memory, a communication interface, and a display.

Referring to FIG. 37, in a particular embodiment, an exemplary digital processing device 3701. The device 3701 can regulate various aspects of the present disclosure, such as, for example, generative item development, analysis, encoding, and pattern recognition. In this embodiment, the digital processing device 3701 includes a central processing unit (CPU, also "processor" and "computer processor" herein) 3705, which can be a single core or multi core processor, or a plurality of processors for parallel processing. The digital processing device 3701 also includes memory or memory location 3710 (e.g., random-access memory, read-only memory, flash memory), electronic storage unit 3715 (e.g., hard disk), communication interface 3720 (e.g., network adapter) for communicating with one or more other systems, and peripheral devices 3725, such as cache, other memory, data storage and/or electronic display adapters. The memory 3710, storage unit 3715, interface 3720 and peripheral devices 3725 are in communication with the CPU 3705 through a communication bus (solid lines), such as a motherboard. The storage unit 3715 can be a data storage unit (or data repository) for storing data. The digital processing device 3701 can be operatively coupled to a computer network ("network") 3730 with the aid of the communication interface 3720. The network 3730 can be the Internet, an internet and/or extranet, or an intranet and/or extranet that is in communication with the Internet. The network 3730 in some cases is a telecommunication and/or data network. The network 3730 can include one or more computer servers, which can enable distributed computing, such as cloud computing. The network 3730, in some cases with the aid of the device 3701, can implement a peer-to-peer network, which may enable devices coupled to the device 3701 to behave as a client or a server.

Continuing to refer to FIG. 37, the CPU 3705 can execute a sequence of machine-readable instructions, which can be embodied in a program or software. The instructions may be stored in a memory location, such as the memory 3710. The instructions can be directed to the CPU 3705, which can subsequently program or otherwise configure the CPU 3705 to implement methods of the present disclosure. Examples of operations performed by the CPU 3705 can include fetch, decode, execute, and write back. The CPU 3705 can be part of a circuit, such as an integrated circuit. One or more other components of the device 3701 can be included in the circuit. In some cases, the circuit is an application specific integrated circuit (ASIC) or a field programmable gate array (FPGA).

Continuing to refer to FIG. 37, the storage unit 3715 can store files, such as drivers, libraries and saved programs. The storage unit 3715 can store user data, e.g., user preferences and user programs. The digital processing device 3701 in some cases can include one or more additional data storage units that are external, such as located on a remote server that is in communication through an intranet or the Internet.

Continuing to refer to FIG. 37, the digital processing device 3701 can communicate with one or more remote computer systems through the network 3730. For instance, the device 3701 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 3701, such as, for example, on the memory 3710 or electronic storage unit 3715. The machine executable or machine readable code can be provided in the form of software. During use, the code can be executed by the processor 3705. In some cases, the code can be retrieved from the storage unit 3715 and stored on the memory 3710 for ready access by the processor 3705. In some situations, the electronic storage unit 3715 can be precluded, and machine-executable instructions are stored on memory 3710.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe Flash HTML 5, Apple® QuickTime®, Microsoft® Silverlight®, Java™, and Unity®.

Figure 38:
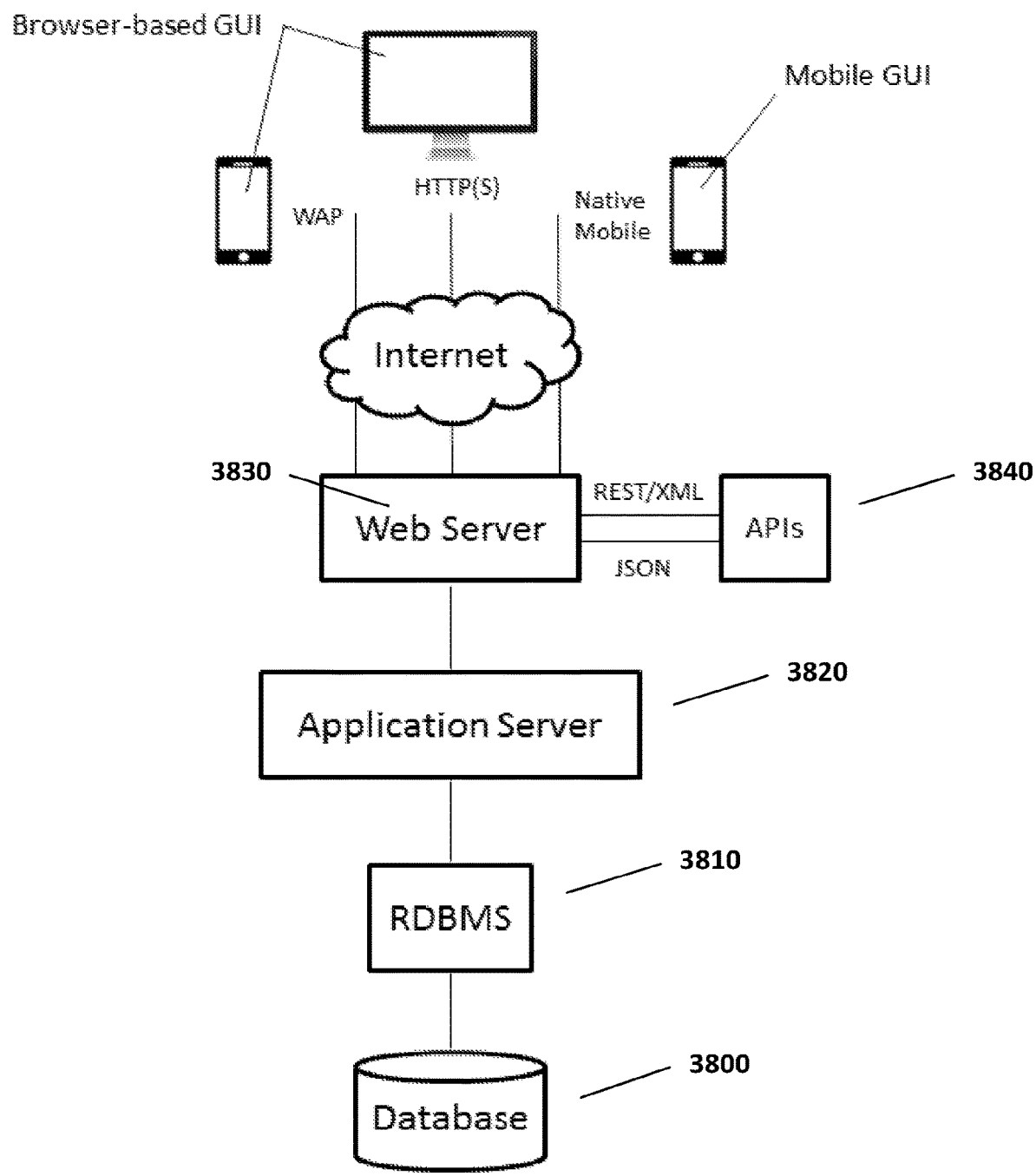
FIG. 38 shows a non-limiting schematic diagram of a web/mobile application provision system; in this case, a system providing browser-based and/or native mobile user interfaces.

Referring to FIG. 38, in a particular embodiment, an application provision system comprises one or more databases 3800 accessed by a relational database management system (RDBMS) 3810. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 3820 (such as Java servers, .NET servers, PHP servers, and the like) and one or more web servers 3830 (such as Apache, IIS, GWS and the like). The web server(s) optionally expose one or more web services via app application programming interfaces (APIs) 3840. Via a network, such as the Internet, the system provides browser-based and/or mobile native user interfaces.

Figure 39:
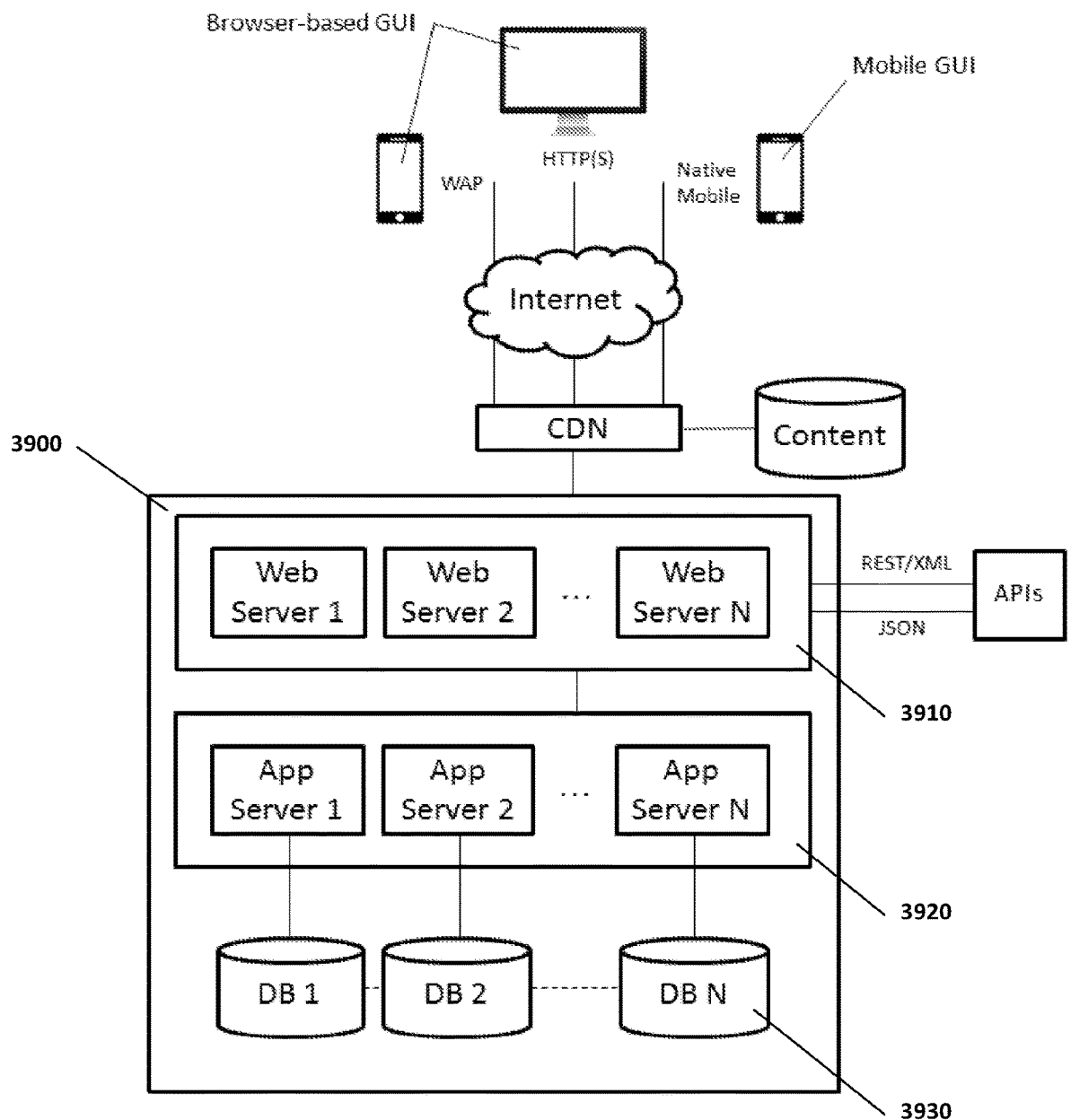
FIG. 39 shows a non-limiting schematic diagram of a cloud-based web/mobile application provision system; in this case, a system comprising an elastically load balanced, auto-scaling web server and application server resources as well synchronously replicated databases.

Referring to FIG. 39, in a particular embodiment, an application provision system alternatively has a distributed, cloud-based architecture 3900 and comprises elastically load balanced, auto-scaling web server resources 3910 and application server resources 3920 as well synchronously replicated databases 3930.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable compiled applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of released items, generative assessment items, patterns, set of rules for encoding responses, etc. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Certain Definitions

Unless otherwise defined, all technical terms used herein have the same meaning as commonly understood by one of ordinary skill in the art to which this invention belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the term "ASCII" refers to the American Standard Code for Information Interchange, which is a character encoding standard for electronic communication that represent text in computers, telecommunications equipment, and other devices.

EXAMPLES

The following illustrative examples are representative of embodiments of the software applications, systems, and methods described herein and are not meant to be limiting in any way.

Example 1

In addition to developing the generative assessment items from released items and checking against the TEKS, the items also address the more thematic, cross-grade, emphases found in the mathematics blueprints (i.e. the Reporting Categories). The development of core ideas can be investigated and characterized by the repeated use of generative assessment items including some items that 'evolve' over a number of grades by swapping in specific alternative responses while retaining others, as in FIGS. 3, 8, 13, 18, 23, and 29. The across-grade-level use of some items, combined with the increased information associated with the items allow for a more robust and detailed account of the development of student abilities in ways that fit with the thematic emphases of the mathematics blueprints. The repeated items have been developed or selected for their ability to assess both in-grade and across-grade depth of understanding.

Generative assessment items for grade 3 are shown in FIGS. 3-7. Generative assessment items for grade 4 are shown in FIGS. 8-12. Generative assessment items for grade 5 are shown in FIGS. 13-17. Generative assessment items for grade 6 are shown in FIGS. 18-22. Generative assessment items for grade 7 are shown in FIGS. 23-28. Generative assessment items for grade 8 are shown in FIGS. 29-36.

Example 2

Third grade student Sam is looking at an exam providing a non-dichotomous generative assessment item in the form of Multiple Choice Question No. 1. Question No. 1, which is displayed on a computer screen graphical user interface, asks "What is the same as ½?" Question No. 1 further offers six possible options: A being ½; B being ⅜; C being 100/200; D being 2/1; E being ¼; and F being 0.01/0.02. After reviewing the question, Sam selects with his mouse A, B, C, and D while leaving E and F unselected.

Instructor Ivan uses a traditional system that detects that Sam selected A, B, C, and D. The traditional system compares Sam's select to the correct combination: A, B, C, and F. Because Sam's selection is not a perfect match to the correct answer, Sam's response to Question No. 1 is scored as a "0" and Sam's original response of A, B, C, and D is discarded, forever lost. Only the scored "0" to Question No. 1 is saved.

Alternatively, Instructor Ivan utilizes an embodiment of the claimed non-dichotomous answer processing application. This application detects that Sam selected A, B, C, and D and E and F were not selected. The application continues to convert every one of Sam's selection in Question No. 1 as a "1" and a non-selection as a "0," and concatenates each converted binary to turn Sam's response into "111100." Sam's concatenated response "111100" is saved to later be processed and holds tremendous information density—recording both of Sam's specific selection and non-selection (among a possibility of 64 states) without any information loss. Further, the binary format of Sam's response is compact and provided in a manner that requires only 6 bits to store in contrast to the 24 bits that would have been required to store Sam's A,B,C,D (not including the commas, which would have needed even more bits). This smaller data package that results from the claimed non-dichotomous answer processing application allows the Instructor Ivan's computer to process Sam's response to Question No. 1 more efficiently and effectively than a traditional system.

Example 3

Student Sarah is also taking the same exam as student Sam. In response to Question No. 1, Sarah selects A, B, and C while leaving D, E, and F unselected.

Instructor Ivan wants to not only understand student Sarah's response to Question No. 1, but create a histogram that compares Sarah's response to Question No. 1 with Sam's response to Question No. 1. At first, Instructor Ivan uses the traditional system. But Instructor Ivan runs into a couple of problems. First, the traditional system automatically discarded Sarah's original response of A, B, and C after scoring Sarah's response as a "0." Moreover, when Instructor Ivan tried to concatenate Sam and Sarah's responses together, the result came out to "A,B,C,DA,B,C." The comma placements made computer processing difficult and ambiguous. Moreover, the combined responses required 42 bits for storage (not including the bits to store the commas, which would have required taking up even more data storage).

Instead, Instructor Ivan utilizes another embodiment of the claimed non-dichotomous answer processing application. This application detects that Sarah selected A, B, and C and D, E, and F were not selected. The application continues to convert every one of Sarah's selection to Question No. 1 into a binary format and concatenates them to form "111000." Next, the application further concatenates Sam's concatenated binary response and Sarah's concatenated binary response as "111100111000." This concatenation response across multiple students not only takes up less data storage than the output of the traditional system counterpart, but also provides for more predictable processing.

Example 4

All 50 students in Mr. Barber's Calculus class submit student answer selections to each of 5 answer choices for each of 50 non-dichotomous generative assessment questions. Concatenating the answer selections yields a set of concatenated binary answers 125,000 bits long. Mr. Barber then runs a machine algorithm on the set of concatenated binary answers to identify a probability that each of his 50 students shows signs of autism. Through its training, the machine learning algorithm determines that all students who correctly submitted an answer selection of answer choice C for question 18, but incorrectly submitted an answer non-selection of answer choice D in question 42, have a high probability of being autistic. As such, two of Mr. Barber's 50 students are determined to have a high probability of being autistic based on their answer selections.

Through its training, the machine learning algorithm determines that students who correctly submitted a correct answer selection of answer choice C for question 18, but incorrectly submitted an answer non-selection of answer choice D in question 42, have a higher probability of being autistic. As such, two of Mr. Barber's 50 students who had not been previously identified are determined to have a high probability of being autistic based on their overall answer selections.

While preferred embodiments of the present subject matter have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the subject matter described herein may be employed in practicing the invention.

What is claimed is:

1. A computer-implemented method of identifying a presence of a characteristic, a probability of the presence of the characteristic, or both for each of a plurality of students comprising:
   a) receiving two or more answer selections in a binary format for each of a plurality of non-dichotomous generative assessment items for each of the plurality of students, wherein an answer selection is represented as a first binary number and an answer non-selection is represented as a second binary number;
   b) concatenating the answer selections for each of the plurality of non-dichotomous generative assessment items and for each of the plurality of students to form a set of concatenated answers in a binary format providing a computationally efficient, unambiguous representation of the set of concatenated answers;
   c) creating a first training set comprising a first portion of the set of concatenated answers associated with one or more first students from the plurality of students having an identified characteristic;
   d) training a machine learning algorithm using the first training set;
   e) creating a first test data set comprising a second portion of the set of concatenated answers associated with one or more second students from the plurality of students; and
   f) running the machine learning algorithm on the first test data set to identify the presence of the characteristic, a probability of the presence of the characteristic, or both for each of the one or more second students.

2. The method of claim 1, wherein the characteristic comprises a non-native language, a medical condition, or both.

3. The method of claim 2, wherein the medical condition is a mental disorder, genetic disorder, emotional disorder, behavioral disorder, or any combination thereof.

4. The method of claim 3, wherein the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof.

5. The method of claim 1, wherein the set of concatenated answers are concatenated without a delimiter.

6. The method of claim 1, wherein a size of the concatenated answer is equal to AC bits, wherein AC equals the number of answer choices.

7. The method of claim 1, wherein a size of a multiple item concatenated answer is equal to AC*Q bits, and wherein AC equals a number of answer choices, and wherein Q equals a number of non-dichotomous generative assessment items.

8. A computer-implemented system for identifying a presence of a characteristic, a probability of the presence of the characteristic, or both for each of a plurality of students comprising, the system comprising: a computer-readable storage device coupled to at least one processor and having instructions stored thereon which, when executed by the at least one processor, causes the at least one processor to perform at least the following:
   a) receiving two or more answer selections in a binary format for each of a plurality of non-dichotomous generative assessment items for each of the plurality of students, wherein an answer selection is represented as a first binary number and an answer non-selection is represented as a second binary number;
   b) concatenating the answer selections for each of the plurality of non-dichotomous generative assessment items and for each of the plurality of students to form a set of concatenated answers in a binary format providing a computationally efficient, unambiguous representation of the set of concatenated answers;

c) creating a first training set comprising a first portion of the set of concatenated answers associated with one or more first students from the plurality of students having an identified characteristic, where the first training set comprises, for each set of concatenated answers for each student, a class label attribute in a binary format representing a negative instance or a positive instance of the identified characteristic for said student;

d) training a machine learning algorithm using the first training set;

e) creating a first test data set comprising a second portion of the set of concatenated answers associated with one or more second students from the plurality of students; and f) running the machine learning algorithm on the first test data set to identify the presence of the characteristic, a probability of the presence of the characteristic, or both for each of the one or more second students.

9. The system of claim 8, wherein the characteristic comprises a non-native language, a medical condition, or both.

10. The system of claim 9, wherein the medical condition is a mental disorder, genetic disorder, emotional disorder, behavioral disorder, or any combination thereof.

11. The system of claim 10, wherein the mental disorder comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof.

12. The system of claim 8, wherein the concatenated answers are concatenated without a delimiter.

13. The system of claim 8, wherein a size of the concatenated answer is equal to AC bits, wherein AC equals the number of answer choices.

14. The system of claim 8, wherein a size of multiple item concatenated answer is equal to AC*Q bits, and wherein AC equals a number of answer choices, and wherein Q equals a number of non-dichotomous generative assessment items.

15. A non-transitory computer-readable storage media encoded with a computer program including instructions executable by a processor to create an application to identifying a presence of a characteristic, a probability of the presence of the characteristic, or both for each of a plurality of students, the application performing at least the following:

a) receiving two or more answer selections in a binary format for each of a plurality of non-dichotomous generative assessment items for each of the plurality of students, wherein an answer selection is represented as a first binary number and an answer non-selection is represented as a second binary number;

b) concatenating the answer selections for each of the plurality of non-dichotomous generative assessment items and for each of the plurality of students to form a set of concatenated answers in a binary format providing a computationally efficient, unambiguous representation of the set of concatenated answers;

c) creating a first training set comprising a first portion of the set of concatenated answers associated with one or more first students from the plurality of students having an identified characteristic, where the first training set comprises, for each set of concatenated answers for each student, a class label attribute in a binary format representing a negative instance or a positive instance of the identified characteristic for said student;

d) training a machine learning algorithm using the first training set;

e) creating a first test data set comprising a second portion of the set of concatenated answers associated with one or more second students from the plurality of students having unclassified class label attributes; and f) running the machine learning algorithm on the first test data set to identify the presence of the characteristic, a probability of the presence of the characteristic, or both for each of the one or more second students.

16. The non-transitory computer-readable storage media of claim 15, wherein the characteristic comprises a non-native language, a medical condition, or both, where the medical condition comprises acute stress disorder, amnestic disorder, anosognosia, anxiety disorder, Asperger's syndrome, attention deficit hyperactivity disorder/attention deficit disorder, atypical depression, autism, bipolar disorder, bipolar I disorder, bipolar II disorder, body dysmorphic disorder, borderline intellectual functioning, borderline personality disorder, clinical depression, cognitive disorder, communication disorder, conduct disorder, depression, dyslexia, dyscalculia, generalized anxiety disorder, malingering, minor depressive disorder, obsessive-compulsive disorder (OCD), obsessive-compulsive personality disorder (OCPD), personality disorder, residual schizophrenia, schizophrenia, schizophreniform disorder, or any combination thereof.

17. The non-transitory computer-readable storage media of claim 15, wherein the concatenated answers are concatenated without a delimiter.

18. The non-transitory computer-readable storage of claim 15, wherein an answer selection is stored as a first binary number and an answer non-selection is stored as a second binary number.

19. The non-transitory computer-readable storage media of claim 15, wherein a size of the concatenated answer is equal to AC bits, wherein AC equals the number of answer choices.

20. The non-transitory computer-readable storage media of claim 15, wherein a size of a multiple item concatenated answer is equal to AC*Q bits, and wherein AC equals a number of answer choices, and wherein Q equals a number of non-dichotomous generative assessment items.

* * * * *